United States Patent [19]

deSolms et al.

[11] Patent Number: 6,127,390

[45] Date of Patent: Oct. 3, 2000

[54] INHIBITORS OF PRENYL-PROTEIN TRANSFERASE

[75] Inventors: S. Jane deSolms, Norristown; William C. Lumma, Jr., Pennsburg; Anthony W. Shaw; John T. Sisko, both of Lansdale; Thomas J. Tucker, North Wales, all of Pa.

[73] Assignee: Merck & Co., Inc., Rahway, N.J.

[21] Appl. No.: 09/164,482

[22] Filed: Oct. 1, 1998

Related U.S. Application Data

[60] Provisional application No. 60/060,871, Oct. 2, 1997.

[51] Int. Cl.$^7$ .......................... A61K 31/44; C07D 401/06
[52] U.S. Cl. .................. 514/341; 546/274.1; 546/274.4; 546/275.1
[58] Field of Search ........................ 514/341; 546/274.1, 546/274.4, 275.1

[56] References Cited

U.S. PATENT DOCUMENTS

| | | | |
|---|---|---|---|
| 4,074,051 | 2/1978 | Stevens et al. | 544/140 |
| 4,287,195 | 9/1981 | Heeres et al. | 544/372 |
| 4,329,470 | 5/1982 | Grisar et al. | 546/210 |
| 4,713,387 | 12/1987 | Wantanabe et al. | 514/332 |
| 4,826,835 | 5/1989 | Kuhla et al. | 544/295 |
| 4,914,207 | 4/1990 | Nagel et al. | 546/167 |
| 5,428,164 | 6/1995 | Thurkauf et al. | 544/295 |
| 5,441,970 | 8/1995 | Reitz et al. | 514/340 |
| 5,478,934 | 12/1995 | Yuan et al. | 548/206 |
| 5,491,164 | 2/1996 | DeSolms et al. | 514/423 |
| 5,578,629 | 11/1996 | Ciccarone et al. | 514/397 |
| 5,616,601 | 4/1997 | Khanna et al. | 514/399 |
| 5,627,202 | 5/1997 | deSolms | 514/397 |
| 5,646,280 | 7/1997 | Thurkauf et al. | 544/295 |
| 5,652,257 | 7/1997 | Anthony et al. | 514/399 |
| 5,656,762 | 8/1997 | Thurkauf et al. | 546/210 |
| 5,710,171 | 1/1998 | Dinsmore et al. | 514/396 |

FOREIGN PATENT DOCUMENTS

| | | |
|---|---|---|
| 0 393 607 A2 | 10/1990 | European Pat. Off. . |
| 0 508 393 A1 | 10/1992 | European Pat. Off. . |
| 0 612 731 A1 | 8/1994 | European Pat. Off. . |
| WO 94/08990 | 4/1994 | WIPO . |
| WO 96/31501 | 10/1996 | WIPO . |
| WO 96/32938 | 10/1996 | WIPO . |
| WO 96/34851 | 11/1996 | WIPO . |
| WO 97/36890 | 10/1997 | WIPO . |
| WO 97/36896 | 10/1997 | WIPO . |
| WO 97/36897 | 10/1997 | WIPO . |
| WO 97/36898 | 10/1997 | WIPO . |
| WO 97/36901 | 10/1997 | WIPO . |

OTHER PUBLICATIONS

Chem. abstr., vol. 111, No. 21, p. 742, col. 1, No. 194444b, (1989), O. Shimomura, et al.
Chem. abstr., vol. 109, No. 15, p. 106, col. 2, No. 122899q, (1988), A. Patel, et al.
Chem. abstr., vol. 109, No. 13, p. 618, col. 1, No. 110370x, (1988), A.M. Tikdari, et al.
Chem. abstr., vol. 109, No. 10, p. 101, col. 2, No. 79568s, (1988), G. Bettinetti, et al.
Chem. abstr., vol. 110, No. 9, p. 652, col. 1, No. 75494n, (1989), A.H. Robins, Co., Inc.
Chem. abstr., vol. 110, No. 11, p. 740, col. 2, No. 95589a, (1989), U. Holgrabe, et al.
Chem. abstr., vol. 110, No. 13, p. 688, col. 1, No. 114776c, (1989), C.G. Wermuth, et al.
Chem. abstr., vol. 110, No. 13, p. 742, col. 2, No. 115292d, (1989), P.D. Leeson, et al.
Chem. abstr., vol. 110, No. 21, p. 721, col. 1, No. 192538r, (1989), R.L. Tolman et al.
Chem. abstr., vol. 110, No. 23, p. 748, col. 1, No. 212763r, (1989), J.C. Lancelot, et al.
Chem. abstr., vol. 110, No. 25, p. 627, col. 2, No. 231448h, (1989), Y. Nezu, et al.
Chem. abstr., vol. 111, No. 1, p. 702, col. 1, No. 7319e (1989), N.G. Kandile, et al.
Chem. abstr., vol. 112, No. 23, p. 697, col. 2, No. 217449u, (1990), B. Kaskar,, et al.
Chem. abstr., vol. 112, No. 13, p. 286, col. 2, No. 114120a, (1990), K.H. Chung, et al.
Chem. abstr., vol. 112, No. 1, p. 773, col. 1, No. 7857z, (1990), H. Ishitsuka.
Chem. abstr., vol. 111, No. 11, p. 729, col. 1, No.97094e, (1989), T. Hamazaki, et al.
Chem. abstr., vol. 111, No. 9, p. 727, col. 2, No. 77745q, (1989), K.A. Jacobson, et al.
Exp. Opin. Ther. Patents, vol. 6, No. 12, pp. 1295–1304 (1996), by S. Graham, et al.
Exp. Opin. Ther. Patents, vol. 5, No. 12, pp. 1269–1285 (1995), by S. L. Graham.
Cancer Research, vol. 55, pp. 5302–5309 (1995), by L. Sepp–Lorenzino, et al.
Nature Medicine, vol. 1, No. 8, pp. 792–797 (1995), by N. Kohl, et al.
Proc. Natl. Acad. Sci. USA, vol. 91, pp. 9141–9145 (1994), by N. Kohl, et al.
Science, vol. 260, pp. 1934–1937 (1993), by N. Kohl, et al.
J. of Biol. Chem., vol. 270, No. 11, pp. 6221–6226 (1995), by G. James, et al.
J. of Biol. Chem., vol. 269, No. 44, pp. 27705–27714 (1994), by G. James, et al.
J. of Biol. Chem., vol. 265, No. 11, pp. 7617–7620 (1993), by J. Gibbs, et al.
Payne, et al., Database Caplus On Stn, DN:126:31349.
Derwent Abst. 90–318321/42 (Takeda) abstract of JP 02229169.
Matsuzaka, et al. CA 99:203546, 1983.

*Primary Examiner*—Jane Fan
*Attorney, Agent, or Firm*—David A. Muthard; Mark R. Daniel

[57] ABSTRACT

The present invention is directed to compounds which inhibit prenyl-protein transferase (FTase) and the prenylation of the oncogene protein Ras. The invention is further directed to chemotherapeutic compositions containing the compounds of this invention and methods for inhibiting prenyl-protein transferase and the prenylation of the oncogene protein Ras.

18 Claims, No Drawings

INHIBITORS OF PRENYL-PROTEIN TRANSFERASE

RELATED APPLICATION

The present patent application is a non-provisional application claiming priority from copending povisional application Ser. No. 60/060,871, filed Oct. 2, 1997.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in four general classes (S. Graham, *Expert Opinion Ther. Patents*, (1995) 5:1269–1285). The first are analogs of farnesyl diphosphate (FPP), while a second class of inhibitors is related to the protein substrates (e.g., Ras) for the enzyme. Bisubstrate inhibitors and inhibitors of farnesyl-protein transferase that are non-competitive with the substrates have also been described. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

Recently, certain tricyclic compounds which optionally incorporate a piperidine moiety have been disclosed to be inhibitors of FPTase (WO 95/10514, WO 95/10515 and WO 95/10516). Imidazole-containing compounds which are claimed to be inhibitors of farnesyl protein transferase have also been disclosed (WO 95/09001 and EP 0 675 112 A1). WO 95/09001 discloses imidazolyl containing compounds that are inhibitors of farnesyl protein transferase.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It is, therefore, an object of this invention to develop low molecular weight compounds that will inhibit a prenyl-protein transferase and thus, the post-translational prenylation of proteins. It is a further object of this invention to develop chemotherapeutic compositions containing the compounds of this invention and methods for producing the compounds of this invention.

SUMMARY OF THE INVENTION

The present invention comprises bicyclic compounds which inhibit a prenyl-protein transferase. Further contained in this invention are chemotherapeutic compositions containing these prenyl transferase inhibitors and methods for their production.

The compounds of this invention are illustrated by the formula A:

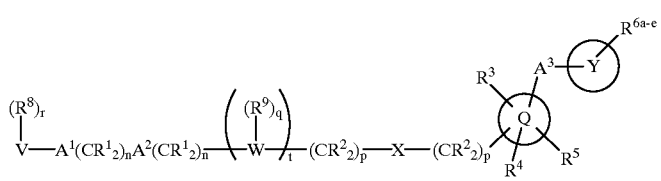

DETAILED DESCRIPTION OF THE INVENTION

The compounds of this invention are useful in the inhibition of prenyl-protein transferases and the prenylation of the oncogene protein Ras. In a first embodiment of this invention, the inhibitors of prenyl-protein transferase are illustrated by the formula A:

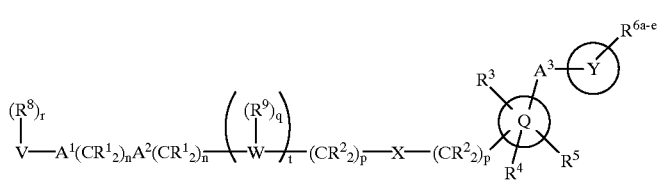

wherein:
Q is a 6-membered heterocyclic ring which comprises a nitrogen atom and 0–2 additional nitrogen atoms and having the remaining atoms being carbon atoms, and which also optionally comprises a carbonyl, thiocarbonyl, $-C(=NR^{13})-$ or sulfonyl moiety adjacent to a nitrogen atom, provided that Q is not piperazine, piperazinone, diketopiperazine, piperidine, piperidinone, diketopiperidine or triketopiperidine;
Y is a 5, 6 or 7 membered carbocyclic ring wherein from 0 to 3 carbon atoms are replaced by a heteroatom selected from N, S and O, and wherein Y is attached to $A^3$ through a carbon atom;
$R^1$ and $R^2$ are independently selected from:
  a) hydrogen,
  b) aryl, heterocycle, $C_3$–$C_{10}$ cycloalkyl, $C_2$–$C_6$ alkenyl, $C_2$–$C_6$ alkynyl, $R^{10}O-$, $R^{11}S(O)_m-$, $R^{10}C(O)NR^{10}-$, $R^{11}C(O)O-$, $(R^{10})_2NC(O)-$, $R^{10}_2N-C(NR^{10})-$, CN, $NO_2$, $R^{10}C(O)-$, $N_3$, $-N(R^{10})_2$, or $R^{11}OC(O)NR^{10}-$,
  c) unsubstituted or substituted $C_1$–$C_6$ alkyl wherein the substituent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O-$, $R^{11}S(O)_m-$, $R^{10}C(O)NR^{10}-$, $(R^{10})_2NC(O)-$, $R^{10}_2N-C(NR^{10})-$, CN, $R^{10}C(O)-$, $N_3$, $-N(R^{10})_2$, and $R^{11}OC(O)-NR^{10}-$;
$R^3$, $R^4$ and $R^5$ are independently selected from:
  a) hydrogen,
  b) unsubstituted or substituted aryl or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O-$, $R^{11}S(O)_m-$, $R^{10}C(O)NR^{10}-$, $(R^{10})_2NC(O)-$, $R^{11}C(O)O-$, $R^{10}_2N-C(NR^{10})-$, CN, $NO_2$, $R^{10}C(O)-$, $N_3$, $-N(R^{10})_2$, or $R^{11}OC(O)NR^{10}-$,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O-$, $R^{11}S(O)_m-$, $R^{10}C(O)NR^{10}-$, $(R^{10})_2NC(O)-$, $R^{10}_2N-C(NR^{10})-$, CN, $R^{10}C(O)-$, $N_3$, $-N(R_{10})_2$, and $R^{11}OC(O)-NR^{10}-$;
$R^{6a}$, $R^{6b}$, $R^{6c}$, $R^{6d}$ and $R^{6e}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O-$, $R^{11}S(O)_m-$, $R^{10}C(O)NR^{10}-$, $(R^{10})_2NC(O)-$, $R^{11}C(O)O-$, $R^{10}_2N-C(NR^{10})-$, CN, $NO_2$, $R^{10}C(O)-$, $(R^{10})_2NS(O)_2-$, $R^{11}S(O)_mNR^{10}-$, $N_3$, $-N(R^{10})_2$, or $R^{11}OC(O)NR^{10}-$,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O-$, $R^{11}S(O)_m-$, $R^{10}C(O)NR^{10}-$, $(R^{10})_2NC(O)-$, $(R^{10})_2NS(O)_2-$, $R^{11}S(O)_mNR^{10}-$, $R^{10}_2N-C(NR^{10})-$, CN, $R^{10}C(O)-$, $N_3$, $-N(R^{10})_2$, and $R^{11}OC(O)-NR^{10}-$; or
any two of $R^{6a}$, $R^{6b}$, $R^{6c}$, $R^{6d}$ and $R^{6e}$ on adjacent carbon atoms are combined to form a diradical selected from $-CH=CH-CH=CH-$, $-CH=CH-CH_2-$, $-(CH_2)_4-$ and $-(CH_2)_3-$;
$R^7$ is selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
  a) $C_{1-4}$ alkoxy, b) aryl or heterocycle,

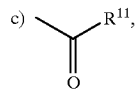

d) —SO$_2$R$^{11}$
e) N(R$^{10}$)$_2$ or
f) C$_{1-4}$ perfluoroalkyl;

R$^8$ is independently selected from:
a) hydrogen,
b) aryl, substituted aryl, heterocycle, substituted heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, (R$^{10}$)$_2$NS(O)$_2$—, R$^{11}$S(O)$_m$NR$^{10}$—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by aryl, cyanophenyl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, (R$^{10}$)$_2$NC(O)—, (R$^{10}$)$_2$NS(O)$_2$—, R$^{11}$S(O)$_m$NR$^{10}$—, R$^{10}$$_2$N—C(NR$^{10}$)—, CN, R$^{10}$C(O)—, N$_3$, —N(R$^{10}$)$_2$, or R$^{10}$OC(O)NH—;

R$^9$ is independently selected from:
a) hydrogen,
b) alkenyl, alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{11}$OC(O)NR$^{10}$—;

R$^{10}$ is independently selected from hydrogen, C$_1$–C$_6$ alkyl, benzyl, 2,2,2-trifluoroethyl and aryl;

R$^{11}$ is independently selected from C$_1$–C$_6$ alkyl and aryl;

R$^{12}$ is independently selected from hydrogen, C$_1$–C$_6$ alkyl, C$_1$–C$_6$ aralkyl, C$_1$–C$_6$ substituted aralkyl, C$_1$–C$_6$ heteroaralkyl, C$_1$–C$_6$ substituted heteroaralkyl, aryl, substituted aryl, heteroaryl, substituted heteraryl, C$_1$–C$_6$ perfluoroalkyl, 2-aminoethyl and 2,2,2-trifluoroethyl;

R$^{13}$ is selected from hydrogen, C$_1$–C$_6$ alkyl, cyano, C$_1$–C$_6$ alkylsulfonyl and C$_1$–C$_6$ acyl;

A$^1$ and A$^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

A$^3$ is selected from: —CH$_2$—, —CH$_2$CH$_2$—, —C≡C—, O, —N(R$^{10}$)—, S(O)$_m$, —C(O)NR$^{10}$—, —NR$^{10}$C(O)—, —CH$_2$C(O)NR$^{10}$—, —CH$_2$NR$^{10}$C(O)—, —C(O)NR$^{10}$CH$_2$—, —NR$^{10}$C(O)CH$_2$—, —CH$_2$O—, —CH$_2$N(R$^{10}$)—, —CH$_2$S(O)$_m$—, —OCH$_2$—, —N(R$^{10}$)CH$_2$— and —S(O)$_m$CH$_2$—;

V is selected from:
a) hydrogen,
b) heterocycle,
c) aryl,
d) C$_1$–C$_{20}$ alkyl wherein from 0 to 4 carbon atoms are replaced with a heteroatom selected from O, S, and N, and
e) C$_2$–C$_{20}$ alkenyl, provided that V is not hydrogen if A$^1$ is S(O)m and V is not hydrogen if A$^1$ is a bond, n is 0 and A$^2$ is S(O)$_m$;

W is a heterocycle;

X is a bond, —CH=CH—, O, —C(=O)—, —C(O)NR$^7$—, —NR$^7$C(O)—, —C(O)O—, —OC(O)—, —C(O)NR$^7$C(O)—, —NR$^7$—, —S(O)$_2$N(R$^{10}$)—, —N(R$^{10}$)S(O)$_2$— or —S(=O)$_m$—;

m is 0, 1 or 2;

n is independently 0, 1, 2, 3 or 4;

p is independently 0, 1, 2, 3 or 4;

q is 0, 1, 2 or 3;

r is 0 to 5, provided that r is 0 when V is hydrogen; and t is 0 or 1;

or a pharmaceutically acceptable salt thereof.

In a preferred embodiment of this invention, the inhibitors of prenyl-protein transferase are illustrated by the formula A:

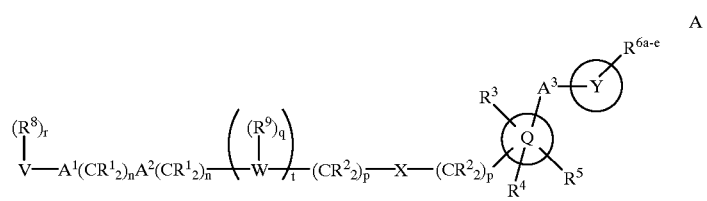

wherein:

Q is a 6-membered heterocyclic ring which comprises a nitrogen atom and 0–2 additional nitrogen atoms and having the remaining atoms being carbon atoms, and which also optionally comprises a carbonyl, thiocarbonyl, —C(=NR$^{13}$)— or sulfonyl moiety adjacent to a nitrogen atom, provided that Q is not piperazine, piperazinone, diketopiperazine, piperidine, piperidinone, diketopiperidine or triketopiperidine;

Y is a 5, 6 or 7 membered carbocyclic ring wherein from 0 to 3 carbon atoms are replaced by a heteroatom selected from N, S and O, and wherein Y is attached to A$^3$ through a carbon atom;

R$^1$ and R$^2$ are independently selected from:
a) hydrogen,
b) aryl, heterocycle, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, R$^{11}$C(O)O—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
c) unsubstituted or substituted C$_1$–C$_6$ alkyl wherein the substituent on the substituted C$_1$–C$_6$ alkyl is selected from unsubstituted or substituted aryl, heterocyclic, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, (R$^{10}$)$_2$NC (O)—, $R^{10}{}_2N$—C($NR^{10}$)—, CN, $R^{10}$C(O)—, $N_3$, —N($R_{10}$)$_2$, and $R^{11}$OC(O)—$NR^{10}$—;

$R^3$, $R^4$ and $R^5$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)$NR^{10}$—, ($R^{10}$)$_2$NC(O)—, $R^{11}$C(O)O—, $R^{10}{}_2$N—C($NR^{10}$)—, CN, $NO_2$, $R^{10}$C(O)—, $N_3$, —N($R^{10}$)$_2$, or $R^{11}$OC(O)$NR^{10}$—,
c) unsubstituted $C_1$–$C_6$ alkyl,
d) substituted $C_1$–$C_6$ alkyl wherein the substituent on the $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)$NR^{10}$—, ($R^{10}$)$_2$NC(O)—, $R^{10}{}_2$N—C($NR^{10}$)—, CN, $R^{10}$C(O)—, $N_3$, —N($R_{10}$)$_2$, and $R^{11}$OC(O)—$NR^{10}$—;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)$NR^{10}$—, ($R^{10}$)$_2$NC(O)—, $R^{11}$C(O)O—, $R^{10}{}_2$N—C($NR^{10}$)—, CN, $NO_2$, $R^{10}$C(O)—, ($R^{10}$)$_2$NS(O)$_2$—, $R^{11}$S(O)$_m$$NR^{10}$—, $N_3$, —N($R^{10}$)$_2$, or $R^{11}$OC(O)$NR^{10}$—,
c) unsubstituted $C_1$–$C_6$ alkyl,
d) substituted $C_1$–$C_6$ alkyl wherein the substituent on the $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$ O—, $R^{11}$S(O)$_m$—, $R^{10}$C(O)$NR^{10}$—, ($R^{10}$)$_2$NC(O)—, ($R^{10}$)$_2$NS(O)$_2$—, $R^{11}$S(O)$_m$$NR^{10}$, $R^{10}{}_2$N—C($NR^{10}$)—, CN, $R^{10}$C(O)—, $N_3$, —N($R^{10}$)$_2$, and $R^{11}$OC(O)—$NR^{10}$—; or any two of $R^{6a}$, $R^{6b}$, $R^{6c}$, $R^{6d}$ and $R^{6e}$ on adjacent carbon atoms are combined to form a diradical selected from —CH═CH—CH═CH—, —CH═CH—$CH_2$—, —($CH_2$)$_4$— and —($CH_2$)$_3$—;

$R^7$ is selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
a) $C_{1-4}$ alkoxy,
b) aryl or heterocycle, c) 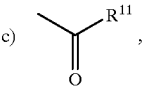

d) —$SO_2R^{11}$
e) N($R^{10}$)$_2$ or
f) $C_{1-4}$ perfluoroalkyl;

$R^8$ is independently selected from:
a) hydrogen,
b) aryl, substituted aryl, heterocycle, substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{10}$O—, $R^{11}$S(O)$_m$—, $R^{10}$C(O)$NR^{10}$—, ($R^{10}$)$_2$NC(O)—, ($R^{10}$)$_2$NS(O)$_2$—, $R^{11}$S(O)$_m$$NR^{10}$—, $R^{10}{}_2$N—C($NR^{10}$)—, CN, $NO_2$, $R^{10}$C(O)—, $N_3$, —N($R^{10}$)$_2$, or $R^{11}$OC(O)$NR^{10}$—, and c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}$O—, $R^{11}$S(O)$_m$—, $R^{10}$C(O)NH—, ($R^{10}$)$_2$NC(O)—, ($R^{10}$)$_2$NS(O)$_2$—, $R^{11}$S(O)$_m$$NR^{10}$—, $R^{10}{}_2$N—C($NR^{10}$)—, CN, $R^{10}$C(O)—, $N_3$, —N($R^{10}$)$_2$, or $R^{10}$OC(O)NH—;

$R^9$ is independently selected from:
a) hydrogen,
b) alkenyl, alkynyl, perfluoroalkyl, F, Cl, Br, $R^{10}$O—, $R^{11}$S(O)$_m$—, $R^{10}$C(O)$NR^{10}$—, ($R^{10}$)$_2$NC(O)—, $R^{10}{}_2$N—C($NR^{10}$)—, CN, $NO_2$, $R^{10}$C(O)—, $N_3$, —N($R^{10}$)$_2$, or $R^{11}$OC(O)$NR^{10}$—, and
c) $C_1$–$C_6$ alkyl unsubstituted or substituted by perfluoroalkyl, F, Cl, Br, $R^{10}$O—, $R^{11}$S(O)$_m$—, $R^{10}$C(O)$NR^{10}$—, ($R^{10}$)$_2$NC(O)—, $R^{10}{}_2$N—C($NR^{10}$)—, CN, $R^{10}$C(O)—, $N_3$, —N($R^{10}$)$_2$, or $R^{11}$OC(O)$NR^{10}$—;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted hetaryl, $C_1$–$C_6$ perfluoroalkyl, 2-aminoethyl and 2,2,2-trifluoroethyl;

$R^{13}$ is selected from hydrogen, $C_1$–$C_6$ alkyl, cyano, $C_1$–$C_6$ alkylsulfonyl and $C_1$–$C_6$ acyl;

$A^1$ and $A^2$ are independently selected from: a bond, —CH═CH—, —C≡C—, —C(O)—, —C(O)$NR^{10}$—, —$NR^{10}$C(O)—, O, —N($R^{10}$)—, —S(O))$_2$N($R^{10}$)—, —N($R^{10}$)S(O))$_2$—, or S(O)$_m$;

$A^3$ is selected from: —$CH_2$—, O, —N($R^{10}$)—, S(O)$_m$, —C(O)$NR^{10}$—, —$NR^{10}$C(O)—, —$CH_2$C(O)$NR^{10}$—, —$CH_2NR^{10}$C(O)—, —C(O)$NR^{10}$$CH_2$—, —$NR^{10}$C(O)$CH_2$—, —$CH_2$O—, —$CH_2$N($R^{10}$)—, $CH_2$S(O)$_m$—, —O$CH_2$—, —N($R^{10}$)$CH_2$— and —S(O)$_m$$CH_2$—;

V is selected from:
a) hydrogen,
b) heterocycle,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl,
provided that V is not hydrogen if $A^1$ is S(O)$_m$ and V is not hydrogen if $A^1$ is a bond, n is 0 and $A^2$ is S(O)$_m$;

W is a heterocycle;

X is a bond, —CH═CH—, O, —C(═O)—, —C(O)$NR^7$—, —$NR^7$C(O)—, —C(O)O—, —OC(O)—, —C(O)$NR^7$C(O)—, —$NR^7$—, —S(O))$_2$N($R^{10}$)—, —N($R^{10}$)S(O))$_2$— or —S(═°)$_m$—;

m is 0, 1 or 2;
n is independently 0, 1, 2, 3 or 4;
p is independently 0, 1, 2, 3 or 4;
q is 0, 1, 2 or 3;
r is 0 to 5, provided that r is 0 when V is hydrogen; and
t is 0 or 1;
or a pharmaceutically acceptable salt thereof Another preferred embodiment of the compounds of this invention is illustrated by the following formula A:

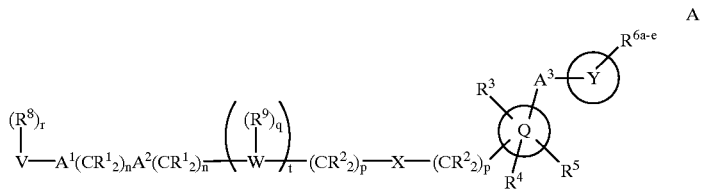

wherein
- Q is a 6-membered heterocyclic ring which comprises a nitrogen atom and 0–2 additional nitrogen atoms and having the remaining atoms being carbon atoms, and which also optionally comprises a carbonyl, thiocarbonyl, —C(=NR$^{13}$)— or sulfonyl moiety adjacent to a nitrogen atom, provided that Q is not piperazine, piperazinone, diketopiperazine, piperidine, piperidinone, diketopiperidine or triketopiperidine;
- Y is selected from: phenyl, cyclohexyl, pyridyl, pyrimidinyl, pyrazinyl, furyl, thiazolyl, isothiazolyl, tetrahydrofuryl, piperdinyl, thiazolidinyl, piperazinyl and tetrahydrothienyl;
- R$^1$ is independently selected from: hydrogen, C$_3$–C$_{10}$ cycloalkyl, R$^{10}$O—, —N(R$^{10}$)$_2$, F or C$_1$–C$_6$ alkyl;
- R$^2$ is independently selected from:
  - a) hydrogen,
  - b) aryl, heterocycle, C$_3$–C$_{10}$ cycloalkyl, R$^{10}$O—, —N(R$^{10}$)$_2$, F or C$_2$–C$_6$ alkenyl,
  - c) unsubstituted or substituted C$_1$–C$_6$ alkyl wherein the substituent on the substituted C$_1$–C$_6$ alkyl is selected from unsubstituted or substituted aryl, heterocycle, C$_3$–C$_{10}$ cycloalkyl, C$_2$–C$_6$ alkenyl, R$^{10}$O— and —N(R$^{10}$)$_2$;
- R$^3$, R$^4$ and R$^5$ are independently selected from:
  - a) hydrogen,
  - b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
  - c) unsubstituted C$_1$–C$_6$ alkyl;
  - d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)—NR$^{10}$—;
- R$^{6a}$, R$^{6b}$, R$^{6c}$, R$^{6d}$ and R$^{6e}$ are independently selected from:
  - a) hydrogen,
  - b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, (R$^{10}$)$_2$NS(O)$_2$—, R$^{11}$S(O)$_m$NR$^{10}$—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
  - c) unsubstituted C$_1$–C$_6$ alkyl;
  - d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, (R$^{10}$)$_2$NS(O)$_2$—, R$^{11}$S(O)$_m$NR$^{10}$—, R$^{10}$$_2$N—C(NR$^{10}$)—, CN, R$^{10}$C(O)—, N$_3$, —N(R$^{10}$)$_2$, and R$^{11}$OC(O)—NR$^{10}$—; or
- any two of R$^{6a}$, R$^{6b}$, R$^{6c}$, R$^{6d}$ and R$^{6e}$ on adjacent carbon atoms are combined to form a diradical selected from —CH=CH—CH=CH—, —CH=CH—CH$_2$—, —(CH$_2$)$_4$— and —(CH$_2$)$_3$—;
- R$^7$ is selected from: H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:
  - a) C$_{1-4}$ alkoxy,
  - b) aryl or heterocycle,
  - c) 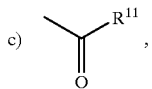
  - d) —SO$_2$R$^{11}$
  - e) N(R$^{10}$)$_2$ or
  - f) C$_{1-4}$ perfluoroalkyl;
- R$^8$ is independently selected from:
  - a) hydrogen,
  - b) aryl, substituted aryl, heterocycle, substituted heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, (R$^{10}$)$_2$NC(O)—, CN, NO$_2$, (R$^{10}$)$_2$N—C(NR$^{10}$)—, R$^{10}$C(O)—, (R$^{10}$)$_2$NS(O)$_2$—, R$^{11}$S(O)$_m$NR$^{10}$—, —N(R$^{10}$)$_2$, or R$^{11}$OC(O)NR$^{10}$—, and
  - c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;
- R$^9$ is selected from:
  - a) hydrogen,
  - b) C$_2$–C$_6$ alkenyl, C$_2$–C$_6$ alkynyl, C$_1$–C$_6$ perfluoroalkyl, F, Cl, R$^{10}$O—, R$^{11}$S(O)$_m$—, R$^{10}$C(O)NR$^{10}$—, (R$^{10}$)$_2$NC(O)—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
  - c) C$_1$–C$_6$ alkyl unsubstituted or substituted by C$_1$–C$_6$ perfluoroalkyl, F, Cl, R$^{10}$O—, R$^{11}$S(O)$_m$—, R$^{10}$C(O)NR$^{10}$—, (R$^{10}$)$_2$NC(O)—, CN, (R$^{10}$)$_2$N—C(NR$^{10}$)—, R$^{10}$C(O)—, —N(R$^{10}$)$_2$, or R$^{11}$OC(O)NR$^{10}$—;
- R$^{10}$ is independently selected from hydrogen, C$_1$–C$_6$ alkyl, benzyl, 2,2,2-trifluoroethyl and aryl;
- R$^{11}$ is independently selected from C$_1$–C$_6$ alkyl and aryl;
- R$^{12}$ is independently selected from hydrogen, C$_1$–C$_6$ alkyl, C$_1$–C$_6$ aralkyl, C$_1$–C$_6$ substituted aralkyl, C$_1$–C$_6$ heteroaralkyl, C$_1$–C$_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

$A^1$ and $A^2$ are independently selected from: a bond, —CH=CH—, —C≡C—, —C(O)—, —C(O)NR$^{10}$—, O, —N(R$^{10}$)—, or S(O)$_m$;

$A^3$ is selected from: —CH$_2$—, O, —N(R$^{10}$)—, S(O)$_m$, —C(O)NR$^{10}$—, —NR$^{10}$C(O)—, —CH$_2$C(O)NR$^{10}$—, —CH$_2$N$^{10}$C(O)—, —C(O)NR$^{10}$CH$_2$—, —NR$^{10}$C(O)CH$_2$—, —CH$_2$O—, —CH$_2$N(R$^{10}$)—, —CH$_2$S(O)$_m$—, —OCH$_2$—, —N(R$^{10}$)CH$_2$— and —S(O)$_m$CH$_2$—;

V is selected from:
a) hydrogen,
b) heterocycle selected from pyrrolidinyl, imidazolyl, imidazolinyl, pyridinyl, thiazolyl, pyridonyl, 2-oxopiperidinyl, oxazolyl, indolyl, quinolinyl, isoquinolinyl, triazolyl and thienyl,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, and provided that V is not hydrogen if $A^1$ is S(O)$_m$ and V is not hydrogen if $A^1$ is a bond, n is 0 and $A^2$ is S(O)$_m$;

W is a heterocycle selected from pyrrolidinyl, imidazolyl, imidazolinyl, pyridinyl, thiazolyl, pyridonyl, 2-oxopiperidinyl, oxazolyl, indolyl, quinolinyl, triazolyl or isoquinolinyl;

X is a bond, O, —C(=O)—, —CH=CH—, —C(O)NR$^7$—, —NR$^7$C(O)—, —NR$^7$—, —S(O))$_2$N(R$^{10}$)—, —N(R$^{10}$)S(O))$_2$— or —S(=O)$_m$—;

m is 0, 1 or 2;

n is independently 0, 1, 2, 3 or 4;

p is independently 0, 1, 2, 3 or 4;

q is 0, 1, 2 or 3;

r is 0 to 5, provided that r is 0 when V is hydrogen; and t is 0 or 1;

or a pharmaceutically acceptable salt thereof.

A preferred embodiment of the compounds of this invention are illustrated by the formula B:

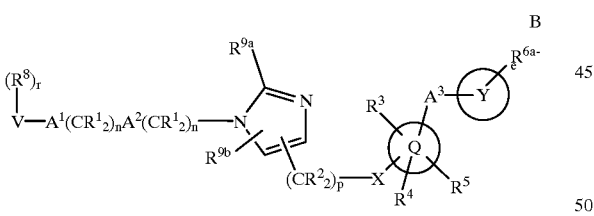

B wherein:

Q is a 6-membered heterocyclic ring which comprises a nitrogen atom and 0–2 additional nitrogen atoms and having the remaining atoms being carbon atoms, and which also optionally comprises a carbonyl, thiocarbonyl, —C(=NR$^{13}$)— or sulfonyl moiety adjacent to a nitrogen atom, provided that Q is not piperazine, piperazinone, diketopiperazine, piperidine, piperidinone, diketopiperidine or triketopiperidine;

Y is selected from: phenyl, cyclohexyl and pyridyl;

$R^1$ is selected from: hydrogen, $C_3$–$C_{10}$ cycloalkyl, R$^{10}$O—, —N(R$^{10}$)$_2$, F or $C_1$–$C_6$ alkyl;

$R^2$ is independently selected from:
a) hydrogen,
b) aryl, heterocycle, $C_3$–$C_{10}$ cycloalkyl, R$^{10}$O—, —N(R$^{10}$)$_2$, F or $C_2$–$C_6$ alkenyl,
c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, R$^{10}$O— and —N(R$^{10}$)$_2$;

$R^3$ and $R^4$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
c) unsubstituted $C_1$–$C_6$ alkyl, d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)—NR$^{10}$—;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, R$^{12}$O—, R$^{11}$S(O)$_m$—, R$^{10}$C(O)NR$^{10}$—, (R$^{10}$)$_2$NC(O)—, (R$^{10}$)$_2$NS(O)$_2$—, R$^{11}$S(O)$_m$NR$^{10}$—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, R$^{12}$O—, R$^{11}$S(O)$_m$—, R$^{10}$C(O)NR$^{10}$—, (R$^{10}$)$_2$NC(O)—, (R$^{10}$)$_2$NS(O)$_2$—, R$^{11}$S(O)$_m$NR$^{10}$—, R$^{10}$$_2$N—C(NR$^{10}$)—, CN, R$^{10}$C(O)—, N$_3$, —N(R$^{10}$)$_2$, and R$^{11}$OC(O)—NR$^{10}$—; or
any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

$R^8$ is independently selected from:
a) hydrogen,
b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, R$^{10}$O—, R$^{10}$C(O)NR$^{10}$—, (R$^{10}$)$_2$NC(O)—, (R$^{10}$)$_2$NS(O)$_2$—, R$^{11}$S(O)$_m$NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) $C_1$–$C_6$ alkyl substituted by $C_1$–$C_6$ perfluoroalkyl, R$^{10}$O—, R$^{10}$C(O)NR$^{10}$—, (R$^{10}$)$_2$N—C(NR$^{10}$)—, (R$^{10}$)$_2$NS(O)$_2$—, R$^{11}$S(O)$_m$NR$^{10}$—, R$^{10}$C(O)—, —N(R$_{10}$)$_2$, or R$^{11}$OC(O)NR$^{10}$—;

$R^{9a}$ and $R^{9b}$ are independently hydrogen, $C_1$–$C_6$ alkyl, trifluoromethyl and halogen;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

$A^1$ and $A^2$ are independently selected from: a bond, —CH=CH—, —C≡C—, —C(O)—, —C(O)NR$^{10}$—, O, —N(R$^{10}$)—, or S(O)$_m$;

$A^3$ is selected from: —CH$_2$—, O, —N(R$^{10}$)—, —C(O)NR$^{10}$—, —C(O)NR$^{10}$CH$_2$—, —CH$_2$C(O)NR$^{10}$—, —CH$_2$O—, —OCH$_2$— or S(O)$_m$;

V is selected from:
  a) hydrogen,
  b) heterocycle selected from pyrrolidinyl, imidazolyl, imidazolinyl, pyridinyl, thiazolyl, pyridonyl, 2-oxopiperidinyl, oxazolyl, indolyl, quinolinyl, isoquinolinyl, triazolyl and thienyl,
  c) aryl,
  d) $C_1$–$C_{20}$ alkyl wherein from 0 to 4 carbon atoms are replaced with a heteroatom selected from O, S, and N, and
  e) $C_2$–$C_{20}$ alkenyl, and
provided that V is not hydrogen if $A^1$ is S(O)m and V is not hydrogen if $A^1$ is a bond, n is 0 and $A^2$ is S(O)$_m$;

X is a bond, —CH=CH—, —C(O)NR$^{10}$—, —NR$^{10}$C(O)—, —NR$^{10}$—, O or —C(=O)—;

m is 0, 1 or 2;

n is independently 0, 1, 2, 3 or 4;

p is 0, 1, 2, 3 or 4; and r is 0 to 5, provided that r is 0 when V is hydrogen; or a pharmaceutically acceptable salt thereof.

Another preferred embodiment of the compounds of this invention are illustrated by the formula C:

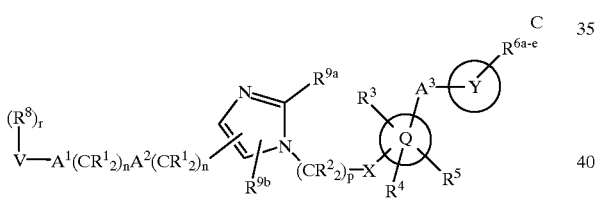

C wherein:

Q is a 6-membered heterocyclic ring which comprises a nitrogen atom and 0–2 additional nitrogen atoms and having the remaining atoms being carbon atoms, and which also optionally comprises a carbonyl, thiocarbonyl, —C(=NR$^{13}$)— or sulfonyl moiety adjacent to a nitrogen atom, provided that Q is not piperazine, piperazinone, diketopiperazine, piperidine, piperidinone, diketopiperidine or triketopiperidine;

Y is selected from: phenyl, cyclohexyl, pyridyl, pyrimidinyl, pyrazinyl, furyl, thiazolyl, isothiazolyl, tetrahydrofuryl, piperdinyl, thiazolidinyl, piperazinyl and tetrahydrothiophenyl;

$R^1$ is selected from: hydrogen, $C_3$–$C_{10}$ cycloalkyl, $R^{10}$O—, —N(R$^{10}$)$_2$, F or $C_1$–$C_6$ alkyl;

$R^2$ is independently selected from:
  a) hydrogen,
  b) aryl, heterocycle, $C_3$–$C_{10}$ cycloalkyl, $R^{10}$O—, —N(R$^{10}$)$_2$, F or $C_2$–$C_6$ alkenyl,
  c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^{10}$O— and —N(R$^{10}$)$_2$;

$R^3$ and $R^4$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, CN(R$^{10}$)$_2$NC(O)—, $R^{10}{}_2$N—C(NR$^{10}$)—, CN, NO$_2$, $R^{10}$C(O)—, N$_3$, —N(R$_{10}$)$_2$, or $R^{11}$OC(O)NR$^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, (R$^{10}$)$_2$NC(O)—, $R^{10}{}_2$N—C(NR$^{10}$)—, CN, $R^{10}$C(O)—, N$_3$, —N(R$^{10}$)$_2$, and $R^{11}$OC(O)—NR$^{10}$—;

$R^{6a}$, $R^{6b}$, $R^{6c}$, $R^{6d}$ and $R^{6e}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, RlOC(O)NR$^{10}$—, (R$^{10}$)$_2$NC(O)—, $R^{11}$S(O)$_2$NR$^{10}$—, (R$^{10}$)$_2$NS(O)$_2$—, $R^{10}{}_2$N—C(NR$^{10}$)—, CN, NO$_2$, $R^{10}$C(O)—, N$_3$, —N(R$^{10}$)$_2$, or $R^{11}$OC(O)NR$^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, (R$^{10}$)$_2$NC(O)—, $R^{11}$S(O)$_2$NR$^{10}$—, (R$^{10}$)$_2$NS(O)$_2$—, $R^{10}{}_2$N—C(NR$^{10}$)—, CN, $R^{10}$C(O)—, N$_3$, —N(R$^{10}$)$_2$, and $R^{11}$OC(O)—NR$^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

$R^8$ is independently selected from:
  a) hydrogen,
  b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}$O—, $R^{10}$C(O)NR$^{10}$—, (R$^{10}$)$_2$NC(O)—, $R^{11}$S(O)$_2$NR$^{10}$—, (R$^{10}$)$_2$NS(O)$_2$—, CN, NO$_2$, (R$^{10}$)$_2$N—C(NR$^{10}$)—, $R^{10}$C(O)—, —N(R$^{10}$)$_2$, or $R^{11}$ OC(O)NR$^{10}$—, and
  c) $C_1$–$C_6$ alkyl substituted by $C_1$–$C_6$ perfluoroalkyl, $R^{10}$O—, $R^{10}$C(O)NR$^{10}$—, (R$^{10}$)$_2$NC(O)—, $R^{11}$S(O))$_2$NR$^{10}$—, (R$^{10}$)$_2$NS(O))$_2$—, (R$^{10}$)$_2$N—C(NR$^{10}$)—, $R^{10}$C(O)—, —N(R$^{10}$)$_2$, or $R^{11}$OC(O)NR$^{10}$—;

$R^{9a}$ and $R^{9b}$ are independently hydrogen, $C_1$–$C_6$ alkyl, trifluoromethyl and halogen;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

$A^1$ and $A^2$ are independently selected from: a bond, —CH=CH—, —C≡C—, —C(O)—, —C(O)NR$^{10}$—, O, —N(R$^{10}$)—, or S(O)$_m$;

$A^3$ is selected from: —$CH_2$—, O, —$N(R^{10})$— or $S(O)_m$;
V is selected from:
a) hydrogen,
b) heterocycle selected from pyrrolidinyl, imidazolyl, imidazolinyl, pyridinyl, thiazolyl, pyridonyl, 2-oxopiperidinyl, oxazolyl, indolyl, quinolinyl, isoquinolinyl, triazolyl and thienyl,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, and
provided that V is not hydrogen if $A^1$ is $S(O)_m$ and V is not hydrogen if $A^1$ is a bond, n is 0 and $A^2$ is $S(O)_m$;
X is a bond, —CH=CH—, —$C(O)NR^{10}$—, —$NR^{10}C(O)$—, —$NR^{10}$—, O or —C(=O)—;
m is 0, 1 or 2;
n is independently 0, 1, 2, 3 or 4;
p is 0, 1, 2, 3 or 4, provided that p is not 0 if X is a bond or O; and
r is 0 to 5, provided that r is 0 when V is hydrogen;
or a pharmaceutically acceptable salt thereof.

In a more preferred embodiment of this invention, the inhibitors of prenyl-protein transferase are illustrated by the formula D:

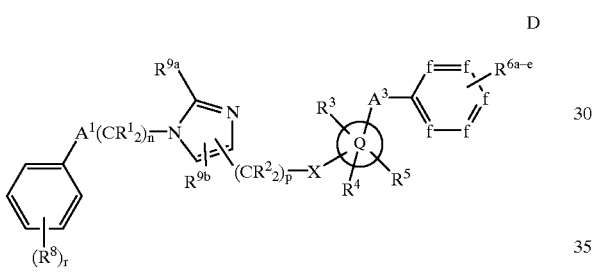

D wherein:
Q is selected from

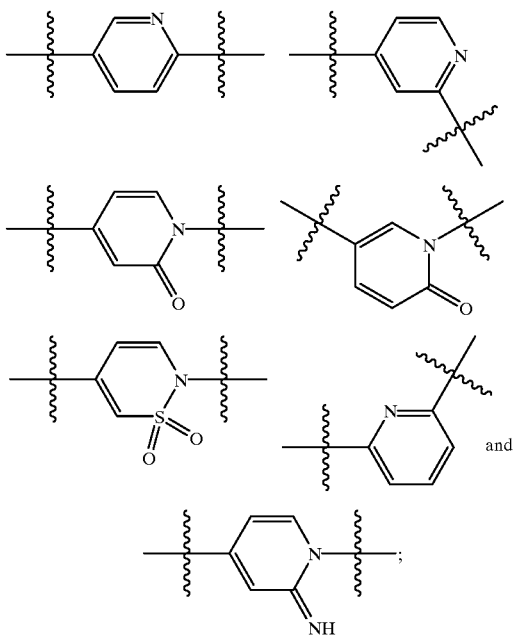

and from 0–1 of f(s) are independently N, and the remaining f's are independently CH;

$R^1$ is selected from: hydrogen, $C_3$–$C_{10}$ cycloalkyl or $C_1$–$C_6$ alkyl;

$R^2$ is independently selected from:
a) hydrogen,
b) aryl, heterocycle, $C_3$–$C_{10}$ cycloalkyl, $R^{10}O$—, —$N(R^{10})_2$, F or $C_2$–$C_6$ alkenyl,
c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;

$R^3$ is selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)NR^{10}$—;

$R^4$ is selected from H, halogen, $C_1$–$C_6$ alkyl and $CF_3$;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

$R^8$ is independently selected from:
a) hydrogen,
b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, $(R^{10})_2NC(O)$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2NC(O)$—, $(R^{10})_2N$—$C(NR^{10})$—, $R^{10}C(O)$—, —$N(R^{10})_2$, or $R^{11}OC(O)NR^{10}$—;

$R^{9a}$ and $R^{9b}$ are independently hydrogen, ethyl, cyclopropyl or methyl;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1-C_6$ alkyl, $C_1-C_6$ aralkyl, $C_1-C_6$ substituted aralkyl, $C_1-C_6$ heteroaralkyl, $C_1-C_6$ substituted heteroaralkyl, aryl, substituted aryl, heteroaryl, substituted hetaryl, $C_1-C_6$ perfluoroalkyl, 2-aminoethyl and 2,2,2-trifluoroethyl;

$A^1$ is selected from: a bond, —C(O)—, O, —N($R^{10}$)—, or $S(O)_m$;

$A^3$ is selected from: —$CH_2$—, O, —N($R^{10}$)— or $S(O)_m$;

X is a bond, —CH═CH—, —C(O)N$R^{10}$—, —N$R^{10}$C(O)—, —N$R^{10}$—, O or —C(═O)—, n is 0 or 1; provided that n is not 0 if $A^1$ is a bond, O, —N($R^{10}$)— or $S(O)_m$;

m is 0, 1 or 2;

p is 0, 1, 2, 3 or 4; and r is 0, 1 or 2;

or a pharmaceutically acceptable salt thereof.

In another more preferred embodiment of this invention, the inhibitors of prenyl-protein transferase are illustrated by the formula E:

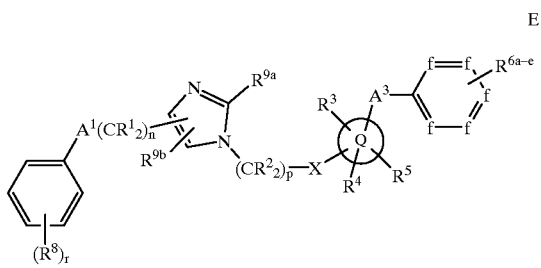

E wherein:
Q is selected from

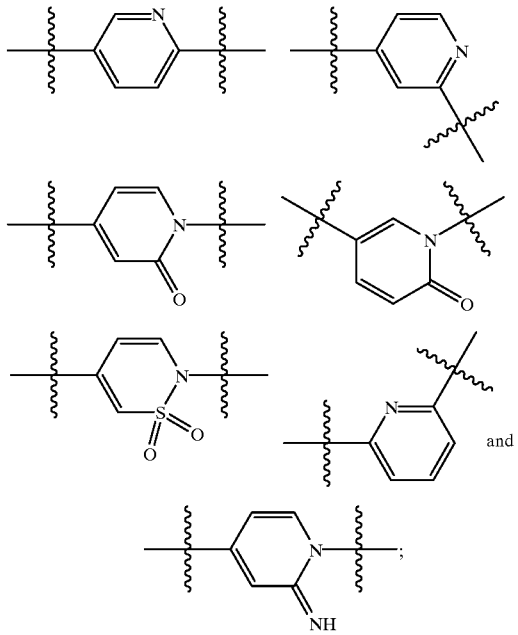

from 0–1 of f(s) are independently N, and the remaining f's are independently CH;

$R^1$ is selected from: hydrogen, $C_3-C_{10}$ cycloalkyl, $R^{10}O$—, —N($R^{10}$)$_2$, F or $C_1-C_6$ alkyl;

$R^2$ is independently selected from:
a) hydrogen,
b) aryl, heterocycle, $C_3-C_{10}$ cycloalkyl, $R^{10}O$—, —N($R^{10}$)$_2$, F or $C_2-C_6$ alkenyl,
c) $C_1-C_6$ alkyl unsubstituted or substituted by aryl, heterocycle, $C_3-C_{10}$ cycloalkyl, $C_2-C_6$ alkenyl, $R^{10}O$—, or —N($R^{10}$)$_2$;

$R^3$ is selected from:
a) hydrogen,
b) unsubstituted or substituted aryl, unsubstituted or substituted heterocycle, $C_3-C_{10}$ cycloalkyl, $C_2-C_6$ alkenyl, $C_2-C_6$ alkynyl, halogen, $C_1-C_6$ perfluoroalkyl, $R^{12}O$—, $R^{11}S(O)_m$—, $R^{10}C(O)NR^{10}$—, $(R^{10})_2NC(O)$—, $R^{10}{}_2N-C(NR^{10})$—, CN, NO$_2$, $R^{10}C(O)$—, N$_3$, —N($R_{10}$)$_2$, or $R^{11}OC(O)NR^{10}$—,
c) unsubstituted $C_1-C_6$ alkyl,
d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, $R^{12}O$—, $R^{11}S(O)_m$—, $R^{10}C(O)NR^{10}$—, $(R^{10})_2NC(O)$—, $R^{10}{}_2N-C(NR^{10})$—, CN, $R^{10}C(O)$—, N$_3$, —N($R_{10}$)$_2$, and $R^{11}OC(O)NR^{10}$—;

$R^4$ is selected from H, halogen, $C_1-C_6$ alkyl and $CF_3$;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3-C_{10}$ cycloalkyl, $C_2-C_6$ alkenyl, $C_2-C_6$ alkynyl, halogen, $C_1-C_6$ perfluoroalkyl, $R^{12}O$—, $R^{11}S(O)_m$—, $R^{10}C(O)NR^{10}$—, $(R^{10})_2NC(O)$—, $R^{10}{}_2N-C(NR^{10})$—, CN, NO$_2$, $R^{10}C(O)$—, N$_3$, —N($R^{10}$)$_2$, or $R^{11}OC(O)NR^{10}$—,
c) unsubstituted $C_1-C_6$ alkyl,
d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, $R^{12}O$—, $R^{11}S(O)_m$—, $R^{10}C(O)NR^{10}$—, $(R^{10})_2NC(O)$—, $R^{10}{}_2N-C(NR^{10})$—, CN, $R^{10}C(O)$—, N$_3$, —N($R^{10}$)$_2$, and $R^{11}OC(O)NR^{10}$—; or
any two of $R^{6a}$, $R^{6b}$, $R^{6c}$, $R^{6d}$ and $R^{6e}$ on adjacent carbon atoms are combined to form a diradical selected from —CH═CH—CH═CH—, —CH═CH—$CH_2$—, —(CH$_2$)$_4$— and —(CH$_2$)$_3$—;

$R^8$ is independently selected from:
a) hydrogen,
b) aryl, substituted aryl, heterocycle, substituted heterocycle, $C_1-C_6$ alkyl, $C_2-C_6$ alkenyl, $C_2-C_6$ alkynyl, $C_1-C_6$ perfluoroalkyl, F, Cl, $R^{10}O$—, $R^{10}C(O)NR^{10}$—, $(R^{10})_2NC(O)$—, CN, NO$_2$, $(R^{10})_2N-C(NR^{10})$—, $R^{10}C(O)$—, —N($R^{10}$)$_2$, or $R^{11}OC(O)NR^{10}$—, and
c) $C_1-C_6$ alkyl substituted by $C_1-C_6$ perfluoroalkyl, $R^{10}O$—, $R^{10}C(O)NR^{10}$—, $(R^{10})_2NC(O)$—, $(R^{10})_2N-C(NR^{10})$—, $R^{10}C(O)$—, —N($R^{10}$)$_2$, or $R^{11}OC(O)NR^{10}$—;

$R^{9a}$ and $R^{9b}$ are independently hydrogen, ethyl, cyclopropyl or methyl;

$R^{10}$ is independently selected from hydrogen, $C_1-C_6$ alkyl, benzyl, 2,2,2-trifluoroethyl and aryl;

$R^{11}$ is independently selected from $C_1-C_6$ alkyl and aryl;

$R^{12}$ is independently selected from hydrogen, $C_1-C_6$ alkyl, $C_1-C_6$ aralkyl, $C_1-C_6$ substituted aralkyl, $C_1-C_6$ heteroaralkyl, $C_1$–$C_6$ substituted heteroaralkyl, aryl, substituted aryl, heteroaryl, substituted hetaryl, $C_1$–$C_6$ perfluoroalkyl, 2-aminoethyl and 2,2,2-trifluoroethyl;

$A^1$ is selected from: a bond, —C(O)—, O, —N($R^{10}$)—, or S(O)$_m$;

$A^3$ is selected from: —CH$_2$—, O, —N($R^{10}$)— or S(O)$_m$;

X is a bond, —CH=CH—, —C(O)N$R^{10}$—, —N$R^{10}$C(O)—, —N$R^{10}$—, O or —C(=O)—;

n is 0 or 1;

m is 0, 1 or 2;

p is 0, 1, 2, 3 or 4, provided that p is not 0 if X is a bond or O; and r is 0, 1 or 2;

or a pharmaceutically acceptable salt thereof.

In a further embodiment of this invention, the inhibitors of prenyl-protein transferase are illustrated by the formula F:

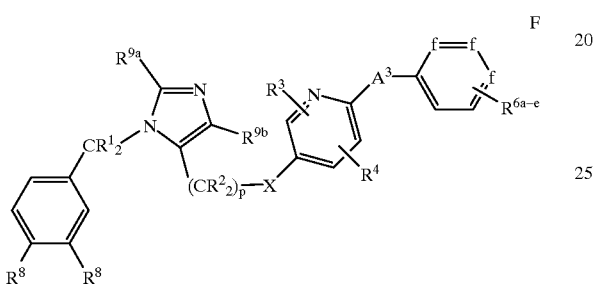

F wherein:
from 0–1 of f(s) are independently N, and the remaining f's are independently CH;

$R^1$ is selected from: hydrogen, $C_3$–$C_{10}$ cycloalkyl or $C_1$–$C_6$ alkyl;

$R^2$ is independently selected from:
  a) hydrogen,
  b) aryl, heterocycle, $C_3$–$C_{10}$ cycloalkyl, $R^{10}$O—, —N($R^{10}$)$_2$ or F,
  c) $C_1$–$C_6$ alkyl unsubstituted or substituted by aryl, heterocycle, $C_3$–$C_{10}$ cycloalkyl, $R^{10}$O—, or —N($R^{10}$)$_2$;

$R^3$ is selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{10}$S(O)$_m$—, $R^{10}$C(O)N$R^{10}$—, ($R^{10}$)$_2$NC(O)—, $R^{10}{}_2$N—C(N$R^{10}$)—, CN, NO$_2$, $R^{10}$C(O)—, N$_3$, —N($R^{10}$)$_2$, or $R^{11}$OC(O)N$R^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)N$R^{10}$—, ($R^{10}$)$_2$NC(O)—, $R^{10}{}_2$N—C(N$R^{10}$)—, CN, $R^{10}$C(O)—, N$_3$, —N($R^{10}$)$_2$, and $R^{11}$OC(O)N$R^{10}$—;

$R^4$ is selected from H, halogen, CH$_3$ and CF$_3$;

$R^{6a}$, $R^{6b}$, $R^{6c}$, $R^{6d}$ and $R^{6e}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)N$R^{10}$—, ($R^{10}$)$_2$NC(O)—, $R^{10}{}_2$N—C(N$R^{10}$)—, CN, NO$_2$, $R^{10}$C(O)—, N$_3$, —N($R^{10}$)$_2$, or $R^{11}$OC(O)N$R^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)(O)N$R^{10}$, ($R^{10}$)$_2$NC(O)—, $R^{10}{}_2$N—C(N$R^{10}$) —, CN, $R^{10}$C(O)—, N$_3$, —N($R^{10}$)$_2$, and $R^{11}$OC(O)—N$R^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

$R^8$ is independently selected from: —CN, Cl, —NO$_2$, $C_1$–$C_6$ alkoxy, and 2,2,2-trifluoroethoxy;

$R^{9a}$ and $R^{9b}$ are independently hydrogen, ethyl, cyclopropyl or methyl;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted hetaryl, $C_1$–$C_6$ perfluoroalkyl, 2-aminoethyl and 2,2,2-trifluoroethyl;

$A^3$ is selected from: —CH$_2$—, O, —N($R^{10}$)— or S(O)$_m$;

X is a bond, —CH=CH—, —C(O)N$R^{10}$—, —N$R^{10}$C(O)—, —N$R^{10}$—, O or —C(=O)—;

m is 0, 1 or 2; and p is 0, 1, 2, 3 or 4;

or a pharmaceutically acceptable salt thereof.

In a further embodiment of this invention, the inhibitors of prenyl-protein transferase are illustrated by the formula G:

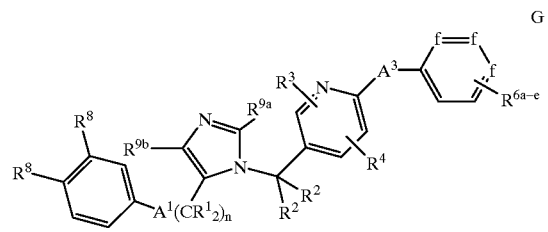

G wherein:
from 0–1 of f(s) are independently N, and the remaining f's are independently CH;

$R^1$ is selected from: hydrogen, $C_3$–$C_{10}$ cycloalkyl, $R^{10}$O—, —N($R^{10}$)$_2$, F or $C_1$–$C_6$ alkyl;

$R^2$ is independently selected from:
  a) hydrogen,
  b) aryl, heterocycle or $C_3$–$C_{10}$ cycloalkyl,
  c) $C_1$–$C_6$ alkyl unsubstituted or substituted by aryl, heterocycle, $C_3$–$C_{10}$ cycloalkyl, $C_2$–$C_6$ alkenyl, $R^{10}$O—, or —N($R^{10}$)$_2$;

$R^3$ is selected from:
  a) hydrogen, b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R_{10})_2$, or $R^{11}OC(O)NR^{10}$—, c) unsubstituted $C_1$–$C_6$ alkyl, d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^4$ is selected from H, halogen, $CH_3$ and $CF_3$;

$R^{6a}$, $R^{6b}$, $R^{6c}$, $R^{6d}$ and $R^{6e}$ are independently selected from:

a) hydrogen, b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—, c) unsubstituted $C_1$–$C_6$ alkyl, d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R_{10})_2$, and $R^{11}OC(O)$—$NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

$R^8$ is independently selected from: —CN, Cl, —$NO_2$, $C_1$–$C_6$ alkoxy, and 2,2,2-trifluoroethoxy;

$R^{9a}$ and $R^{9b}$ are independently hydrogen, ethyl, cyclopropyl or methyl;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted hetaryl, $C_1$–$C_6$ perfluoroalkyl, 2-aminoethyl and 2,2,2-trifluoroethyl;

$A^1$ is selected from: a bond, —C(O)—, O, —$N(R^{10})$—, or $S(O)_m$;

$A^3$ is selected from: —$CH_2$—, O, —$N(R^{10})$— or $S(O)_m$;

m is 0, 1 or 2; and n is 0 or 1;

or a pharmaceutically acceptable salt thereof.

Specific examples of the compounds of the invention are:

5-(4'-Cyanobenzyl)-1-[2-(3"-methylphenylthio)pyrid-5-ylmethyl)imidazole 5-(4'-Cyanobenzyl)-1-[2-(3"-methylphenylphenoxy) pyrid-5-ylmethyl)imidazole 5-(4'-Cyanobenzyl)-1-[2-(3"-chlorophenylthio) pyrid-5-ylmethyl)]imidazole 5-(4'-Cyanobenzyl)-1-[2-(cyclohexylthio)pyrid-5-ylmethyl] imidazole 5-(4'-Cyanobenzyl)-1-[2-(3"-methylphenylthio)pyrid-4-ylmethyl)]imidazole 5-(4'-Cyanobenzyl)-1-[2-(cyclohexylamino)pyrid-5-ylmethyl)]imidazole 5-(4'-Cyanobenzyl)-1-[2-(3 "-chlorophenylthio)pyrid-5-ylmethyl]imidazole -S-oxide 2-[N-(1-(4'-Cyanobenzyl)-1H-imidazol-5-ylethyl) carbamoyl]-6-(3-trifluoromethylphenoxy)pyridine 3-[N-(1-(4'-Cyanobenzyl)-1H-imidazol-5-ylethyl) carbamoyl]-6-(3-trifluoromethylphenoxy)pyridine 3-[N-(1-(4'-Cyanobenzyl)-1H-imidazol-5-ylethyl) carbamoyl]-5-(3-trifluoromethylphenoxy)pyridine 3-[N-(1-(4'-Cyanobenzyl)-1H-imidazol-5-ylethyl) carbamoyl]-5-(3-trifluoromethylbenzyloxy)pyridine 5-chloro-1-(3-chlorobenzyl)-2-oxo-1,2-dihydro-pyridine-3-carboxylic acid {2-[3-(4-cyanobenzyl)-3H-imidazol-4-yl]-ethyl}-amide 1-(3-Chlorobenzyl)-2-oxo-1,2-dihydro-pyridine-3-carboxylic acid {2-[3-(4-cyanobenzyl)-3H-imidazol-4-yl]-ethyl}-amide 1-(3-Trifluoromethylbenzyl)-2-oxo-1,2-dihydro-pyridine-5-carboxylic acid {2-[3-(4-cyanobenzyl)-3H-imidazol-4-yl]-ethyl}-amide 1-(3-Chlorobenzyl)-2-oxo-1,2-dihydro-pyridine-5-carboxylic acid{2-[3-(4-cyanobenzyl)-3H-imidazol-4-yl]-ethyl}-amide 5-Chloro-1-(3-chlorobenzyl)-2-oxo-1,2-dihydro-pyridine-5-carboxylic acid {2-[3-(4-cyanobenzyl)-3H-imidazol-4-yl]-ethyl}-amide 6-[N-(3-Chlorobenzyl) carbamoyl]-4-ethoxy-pyridine-2-carboxylic acid {2-[3-(4-cyanobenzyl)-3H-imidazol-4-yl]-ethyl}-amide 6-[N-(3-Chlorophenyl) carbamoyl]-4-ethoxy-pyridine-2-carboxylic acid {2-[3-(4-cyanobenzyl)-3H-imidazol-4-yl]-ethyl}-amide 4-(3-Chlorobenzyloxy)-6-methoxycarbonyl- pyridine-2-carboxylic acid {2-[3-(4-cyanobenzyl)-3H-imidazol-4-yl]-ethyl}-amide 4-(5-{[6-(3-chloro-phenoxy)-pyridin-2-ylamino]-methyl}-imidazol-1-ylmethyl)-benzonitrile 4-(5-{[6-(phenylethynyl)-pyridin-2-ylamino]-methyl}-imidazol-1ylmethyl)-benzonitrile 4-(5-{[6-(1,2,3,4-tetrahydronaphth-6-yloxy)-pyridin-2-ylamino]methyl}-imidazol-1-ylmethyl)-benzonitrile and 4-(5- {[6-(2-phenylethyl)-pyridin-2-ylamino]-methyl}-imidazol-1-ylmethyl)-benzonitrile or the pharmaceutically acceptable salts thereof.

Particular examples of the compounds of the instant invention are:

5-(4'-Cyanobenzyl)-1-[2-(3"-chlorophenylthio) pyrid-5-ylmethyl)]imidazole

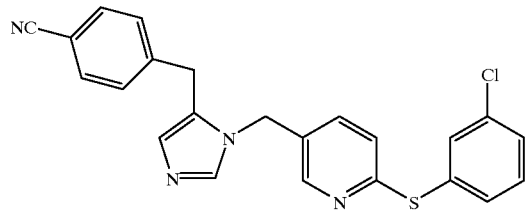

5-(4'-Cyanobenzyl)-1-[2-(3"-methylphenylphenoxy) pyrid-5-ylmethyl)imidazole

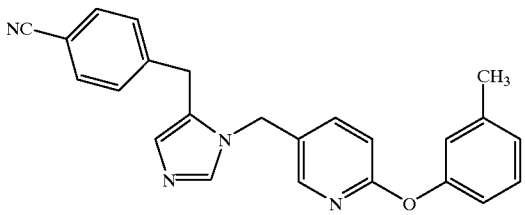

5-chloro-1-(3-chlorobenzyl)-2-oxo-1,2-dihydro-pyridine-3-carboxylic acid {2-[3-(4-cyanobenzyl)-3H-imidazol-4-yl]-ethyl}-amide

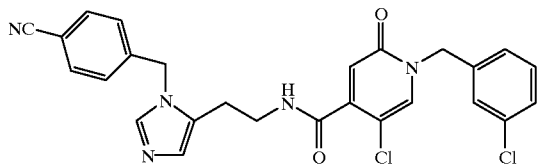

4-(3-Chlorobenzyloxy)-6-methoxycarbonyl-pyridine-2-carboxylic acid {2-[3-(4-cyanobenzyl)-3H-imidazol-4-yl]-ethyl}-amide

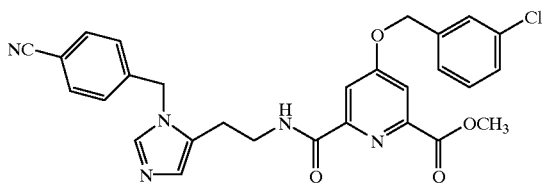

or the pharmaceutically acceptable salts thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^1$, $R^2$ etc.) occurs more than one time in any constituent, its definition on each occurence is independent at every other occurence. Also, combinations of substituents/or variables are permissible only if such combinations result in stable compounds.

As used herein, "alkyl" and the alkyl portion of aralkyl and similar terms, is intended to include both branched and straight-chain saturated aliphatic hydrocarbon groups having the specified number of carbon atoms; "alkoxy" represents an alkyl group of indicated number of carbon atoms attached through an oxygen bridge.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

"Alkynyl" groups include those groups having the specified number of carbon atoms and having one triple bond. Examples of alkynyl groups include acetylene, 2-butynyl, 2-pentynyl, 3-pentynyl and the like.

"Halogen" or "halo" as used herein means fluoro, chloro, bromo and iodo.

As used herein, "carbocyclic ring" is intended to mean any stable monocyclic carbon ring of the designated ring atoms, which can either be aromatic or non-aromatic.

As used herein, "aryl," and the aryl portion of aroyl and aralkyl, is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanvl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein in the definition of $R^3$, $R^4$, $R^5$ and $R^{6a-e}$, the term "the substituted group" is intended to mean a substituted $C_{1-8}$ alkyl, substituted $C_{2-8}$ alkenyl, substituted $C_{2-8}$ alkynyl, substituted aryl or substituted heterocycle from which the substituent(s) $R^3$, $R^4$, $R^5$ and $R^{6a-e}$ are selected.

As used herein in the definition of $R^7$, the substituted $C_{1-8}$ alkyl, substituted $C_{3-6}$ cycloalkyl, substituted aroyl, substituted aryl, substituted heteroaroyl, substituted arylsulfonyl, substituted heteroarylsulfonyl and substituted heterocycle include moieties containing from 1 to 3 substituents in addition to the point of attachment to the rest of the compound.

Lines drawn into the ring systems from substituents (such as from $R^3$, $R^4$, Q etc.) means that the indicated bond may be attached to any of the substitutable ring carbon or nitrogen atoms.

The substituent illustrated by the structure

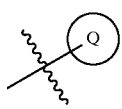

represents a 6-membered heterocyclic ring which comprises a nitrogen atom and 0–2 additional heteroatoms selected from N, S and O, and which optionally comprises a carbonyl, thiocarbonyl, —C(=NR$^{13}$)— or sulfonyl moiety adjacent to the nitrogen atom and includes the following ring systems:

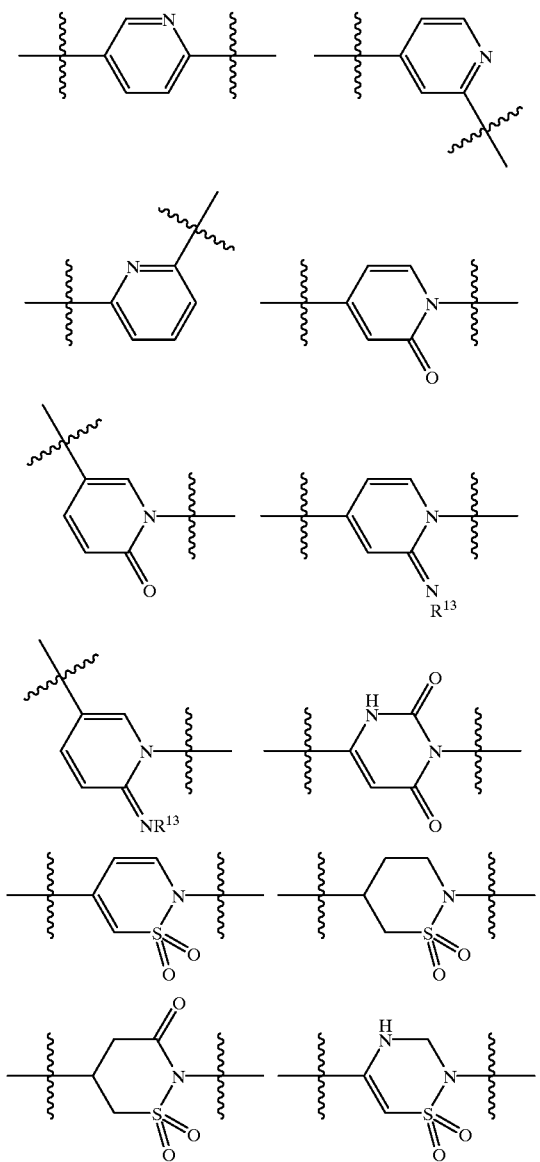

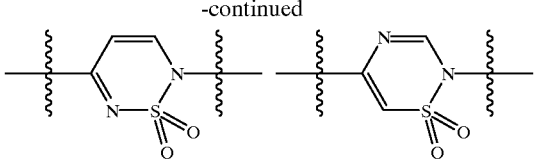

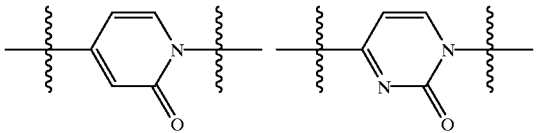

Preferably, the structure 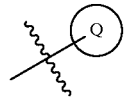 is selected from:

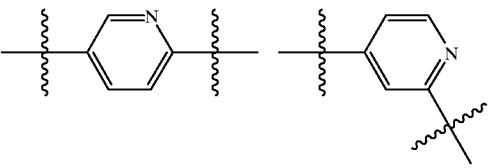

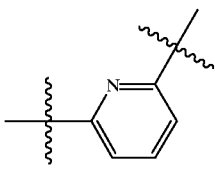

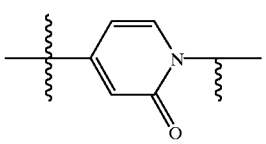

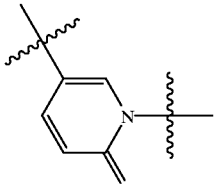

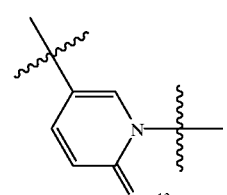

Most preferably, Q is 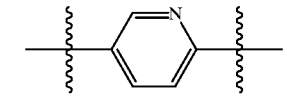

It is understood that such rings may be substituted by $R^3$, $R^4$ and/or $R^5$ as defined hereinabove.

The substituent illustrated by the structure

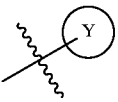

represents a 5, 6 or 7 membered carbocyclic ring wherein from 0 to 3 carbon atoms are replaced by a heteroatom selected from N, S and O, and wherein Y is attached to $A^3$ through a carbon atom and includes the following ring systems:

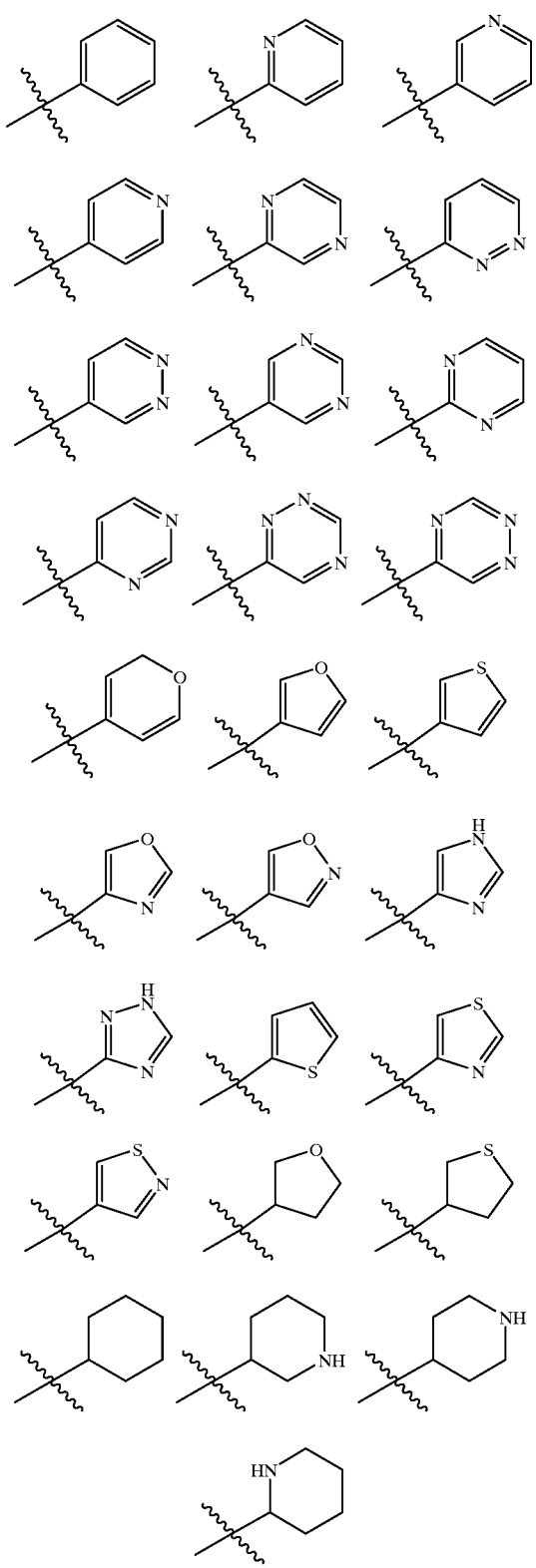

Preferably Y is the moiety designated by the following structure

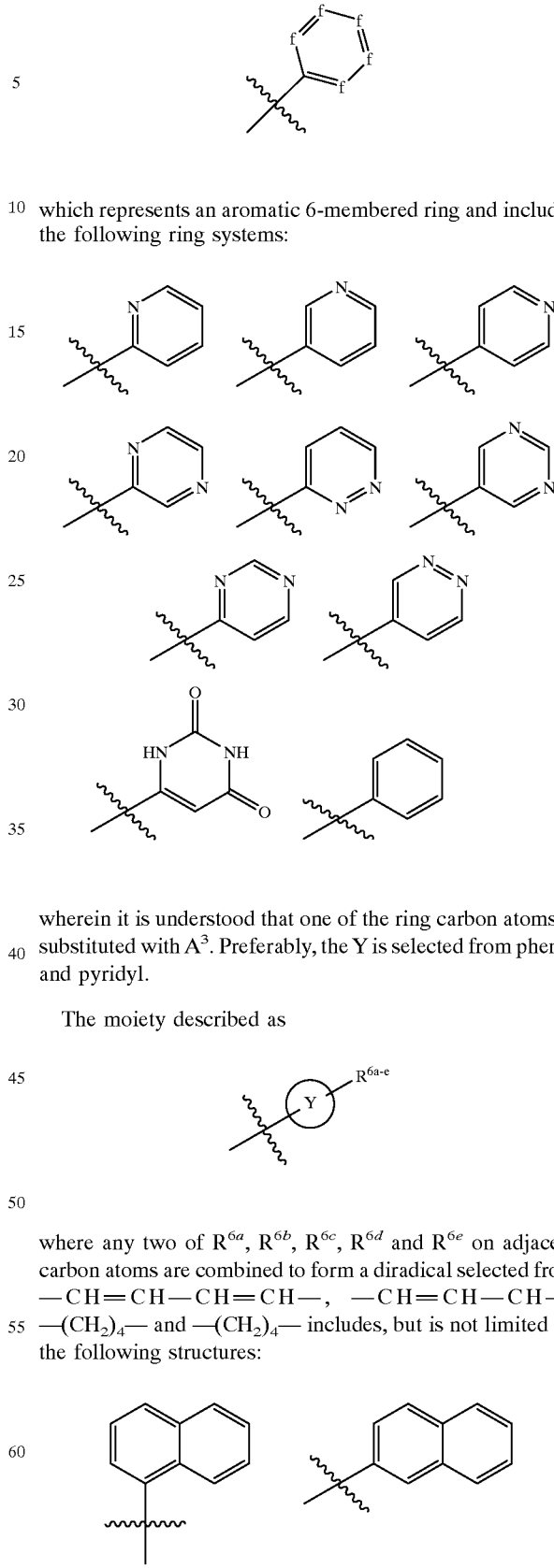

which represents an aromatic 6-membered ring and includes the following ring systems:

wherein it is understood that one of the ring carbon atoms is substituted with $A^3$. Preferably, the Y is selected from phenyl and pyridyl.

The moiety described as where any two of $R^{6a}$, $R^{6b}$, $R^{6c}$, $R^{6d}$ and $R^{6e}$ on adjacent carbon atoms are combined to form a diradical selected from —CH═CH—CH═CH—, —CH═CH—CH—, —(CH$_2$)$_4$— and —(CH$_2$)$_4$— includes, but is not limited to, the following structures:

-continued

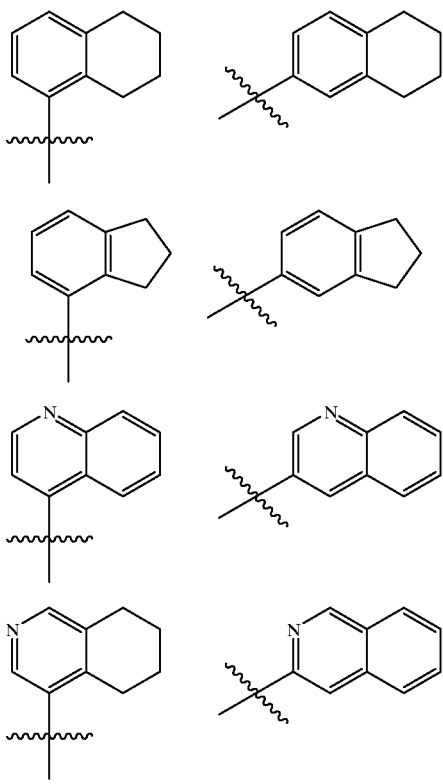

It is understood that such fused ring moieties may be further substituted by the remaining $R^{6a}$, $R^{6b}$, $R^{6c}$, $R^{6d}$ and/or $R^{6e}$ as defined hereinabove.

Preferably, $R^1$ and $R^2$ are independently selected from: hydrogen, $R^{11}C(O)O—$, $—N(R^{10})_2$, $R^{10}C(O)NR^{10}—$, $R^{10}O—$ or unsubstituted or substituted $C_1$–$C_6$ alkyl wherein the substituent on the substituted $C_1$–$C_6$ alkyl is selected from unsubstituted or substituted phenyl, $—N(R^{10})_2$, $R^{10}O—$ and $R^{10}C(O)NR^{10}—$.

Preferably, $R^3$ is selected from:
a) hydrogen,
b) $C_3$–$C_{10}$ cycloalkyl, halogen, $C_1$–$C_6$ perfluoroalkyl, $R^{12}O—$, CN, $NO_2$, $R^{10}C(O)—$ or $—N(R^{10})_2$,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O—$, $R^{11}S(O)_m—$, $R^{10}C(O)NR^{10}—$, $(R^{10})_2$ NC(O)—, $R^{10}{}_2N—C(NR^{10})—$, CN, $R^{10}C(O)—$, $N_3$, $—N(R_{10})_2$, and $R^{11}OC(O)—NR^{10}—$.

Preferably, $R^4$ is selected from: hydrogen, halogen, trifluoromethyl, trifluoromethoxy and $C_1$–$C_6$ alkyl.

Preferably, $R^5$ is hydrogen.

Preferably, $R^{6a}$, $R^{6b}$, $R^{6c}$, $R^{6d}$ and $R^{6e}$ are independently selected from:
a) hydrogen,
b) $C_3$–$C_{10}$ cycloalkyl, halogen, $C_1$–$C_6$ perfluoroalkyl, $R^{12}O—$, $R^{11}S(O)_m—$, CN, $NO_2$, $R^{10}C(O)—$ or $—N(R^{10})_2$,
c) unsubstituted $C_1$–$C_6$ alkyl; and
d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $R^{12}O—$, $R^{11}S(O)_m—$, $R^{10}C(O)—$ or $—N(R_{10})_2$.

Preferably, $R^8$ is independently selected from:
a) hydrogen, and
b) aryl, substituted aryl, heterocycle, substituted heterocycle, $C_1$–$C_6$ perfluoroalkyl, $C_1$–$C_6$ alkoxy, $C_1$–$C_6$ perfluoroalkoxy, 2,2,2-trifluoroethoxy, $—CH_2NHC(O)CH_3$, $—NHC(O)CH_3$ or CN.

Preferably, $R^9$ is hydrogen, halogen or methyl.

Preferably, $R^{10}$ is selected from H, $C_1$–$C_6$ alkyl and benzyl.

Preferably, $A^1$ and $A^2$ are independently selected from: a bond, $—C(O)NR^{10}—$, $—NR^{10}C(O)—$, O, $—N(R^{10})—$, $—S(O))_2N(R^{10})—$ and $—N(R^{10})S(O))_2—$.

Preferably, $A^3$ is selected from $—CH_2—$, O, $—N(R^{10})—$, $—C(O)NR^{10}—$, $—C(O)NR^{10}CH_2—$, $—CH_2C(O)NR^{10}—$, $—CH_2O—$, $—OCH_2—$ or $S(O)_m$. Most preferably, $A^3$ is selected from: $—C(O)NR^{10}—$, $—C(O)NR^{10}CH_2—$, $—OCH_2—$, O or $S(O)_m$.

Preferably, V is selected from hydrogen, heterocycle and aryl. More preferably, V is phenyl.

Preferably, W is selected from imidazolinyl, imidazolyl, oxazolyl, pyrazolyl, pyyrolidinyl, thiazolyl and pyridyl. More preferably, W is selected from imidazolyl and pyridyl.

Preferably, n and r are independently 0, 1, or 2.

Preferably s is 0.

Preferably t is 1.

Preferably, the moiety

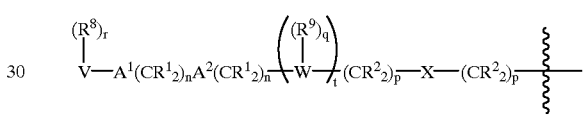

is selected from:

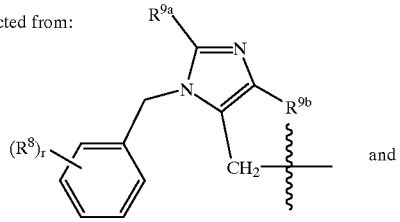

It is intended that the definition of any substituent or variable (e.g., $R^1$, $R^2$, $R^9$, n, etc.) at a particular location in a molecule be independent of its definitions elsewhere in that molecule. Thus, $—N(R^{10})_2$ represents $—NHH$, $—NHCH_3$, $—NHC_2H_5$, etc. It is understood that substituents and substitution patterns on the compounds of the instant invention can be selected by one of ordinary skill in the art to provide compounds that are chemically stable and that can be synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, palmoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–19, in addition to other standard manipulations such as ester hydrolysis, cleavage of protecting groups, etc., as may be known in the literature or exemplified in the experimental procedures. Substituents $R^3$, $R^6$ and $R^8$, as shown in the Schemes, represent the substituents $R^3$, $R^4$, $R^5$, $R^{6a}$, $R^{6b}$, $R^{6c}$, $R^{6d}$, $R^{6e}$ and $R^8$; although only one such $R^3$, $R^6$ or $R^8$ is present in the intermediates and products of the schemes, it is understood that the reactions shown are also applicable when such aryl or heterocyclic moieties contain multiple substituents.

These reactions may be employed in a linear sequence to provide the compounds of the invention or they may be used to synthesize fragments which are subsequently joined by the alkylation reactions described in the Schemes. The reactions described in the Schemes are illustrative only and are not meant to be limiting. Other reactions useful in the preparation of heteroaryl moieties are described in "Comprehensive Organic Chemistry, Volume 4: Heterocyclic Compounds" ed. P. G. Sammes, Oxford (1979) and references therein.

Synopsis of Schemes 1–19:

The requisite intermediates are in some cases commercially available, or can be prepared according to literature procedures. Schemes 1–9 illustrate synthesis of the instant bicyclic compounds which incorporate a preferred benzylimidazolyl sidechain. Thus, in Scheme 1, for example, a bicyclic intermediate that is not commercially available may be synthesized by methods known in the art. Thus, a suitably substituted halogenated picoline 1 may be converted to the dibromo intermediate 2. The dibromide 2 may be coupled to a suitably substituted benzylimidazolyl 3 to provide, after deprotection, the intermediate 4. This intermediate 4 may then be coupled under vigorous conditions to a carbocyclic/heterocyclic ring having a nucleophilic heteroatom to provide a compound of the instant invention 5.

Scheme 2 illustrates an analogous synthesis of an isomeric intermediate 8 starting from a suitably substituted picoline 6.

Synthesis of the instant compounds wherein ring Q is a pyridinone moiety is illustrated in Scheme 3. Thus, a suitably substituted pyridinonyl alcohol 10 may be synthesized starting from the corresponding isonicotinate 9 according to procedures described by Boekelhiede and Lehn (*J. Org. Chem.*, 26:428–430 (1961)). The alcohol is then protected and alkylated with a suitably substituted benzyl halide, to provide the intermediate bicyclic alcohol. The intermediate alcohol 3 may converted to the corresponding bromide 11. The bromide 11 may be coupled to a suitably substituted benzylimidazolyl 3 to provide, after deprotection, the instant compound 12.

Scheme 4 illustrates synthesis of an instant compound wherein a non-hydrogen $R^{9b}$ is incorporated in the instant compound. Thus, a readily available 4-substituted imidazole 13 may be selectively iodinated to provide the 5-iodoimidazole. That imidazole may then be protected and coupled to a suitably substituted benzyl moiety to provide intermediate 14. Intermediate 14 can then undergo the alkylation reactions that were described hereinabove.

Scheme 5 illustrates synthesis of instant compounds that incorporate a preferred imidazolyl moiety connected to the biscyclic portion of the instant compounds via an alkyl amino, sulfonamide or amide linker. Thus, the 4-aminoalkylimidazole 15, wherein the primary amine is protected as the phthalimide, is selectively alkylated then deprotected to provide the amine 16. The amine 16 may then react under conditions well known in the art with various activated arylheteroaryl moieties to provide the instant compounds shown.

Compounds of the instant invention wherein the $A^1(CR^1_2)_nA^2(CR^1_2)_n$ linker is oxygen may be synthesized by methods known in the art, for example as shown in Scheme 6. The suitably substituted phenol 17 may be reacted with methyl N-(cyano)methanimidate to provide the 4-phenoxyimidazole 18. After selective protection of one of the imidazolyl nitrogens, the intermediate 19 can undergo alkylation reactions as described for the benzylimidazoles hereinabove.

Compounds of the instant invention wherein the $A^1(CR^1_2)_nA^2(CR^1_2)_n$ linker is a substituted methylene may be synthesized by the methods shown in Scheme 7. Thus, the N-protected imidazolyl iodide 20 is reacted, under Grignard conditions with a suitably protected benzaldehyde to provide the alcohol 21. Acylation, followed by the alkylation and nucleophilic displacement procedures illustrated in the Schemes above (in particular, Scheme 1) provides the instant compound 22. If other $R^1$ substituents are desired, the acetyl moiety can be manipulated as illustrated in the Scheme.

Scheme 8 illustrates incorporation of an acetyl moiety as the $(CR^2_2)_pX(CR^2_2)_p$ linker of the instant compounds. Thus, the suitably substituted acetyl pyridine 23 is brominated to provide intermediate 24. Reaction with the imidazolyl reagent 5 provides, after deprotection and further functionalization, the instant compound 25.

Scheme 9 illustrates a synthetic route to the instant compounds wherein the heterocyclic-linker-cyclic moiety is first formed and then couple to the preferred imidazolyl moiety.

SCHEME 1
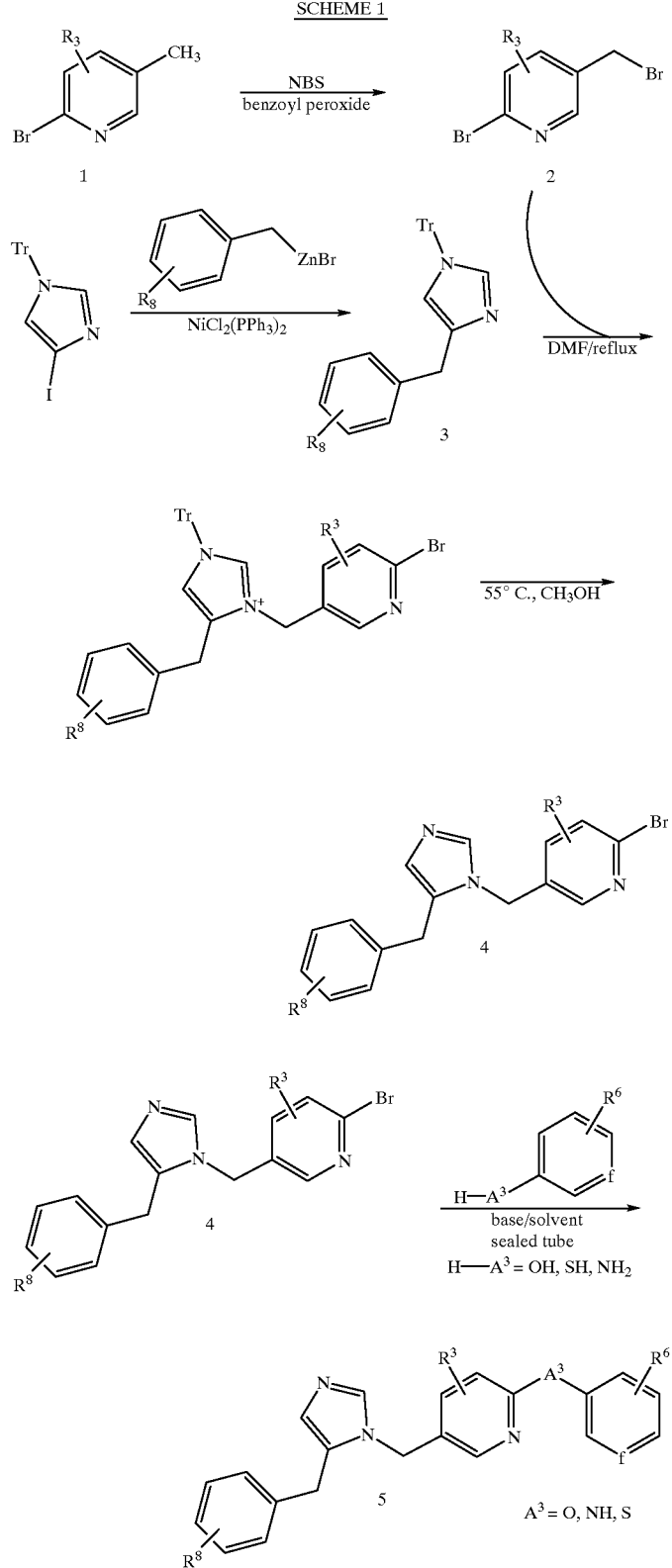

SCHEME 2
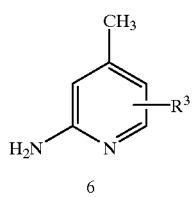
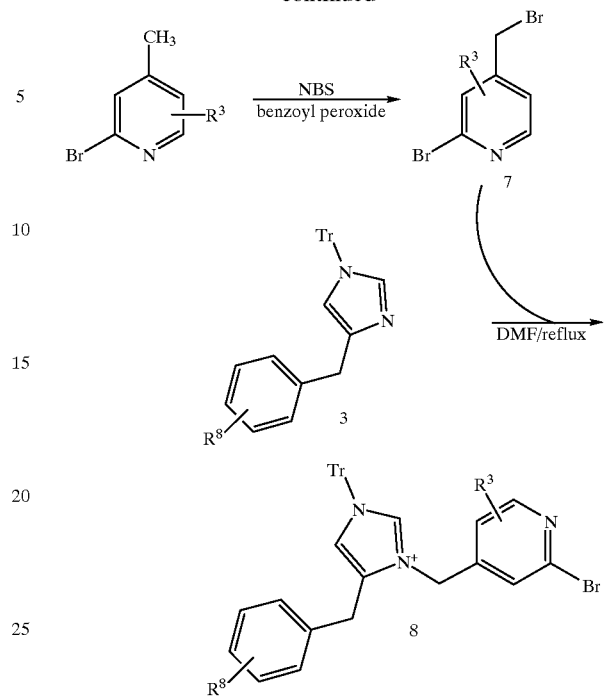
SCHEME 3
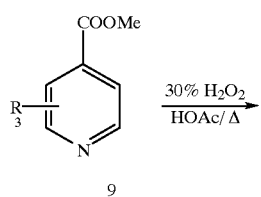
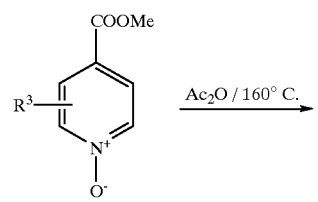
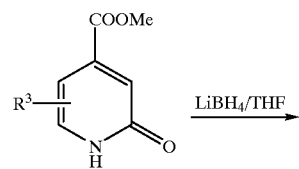
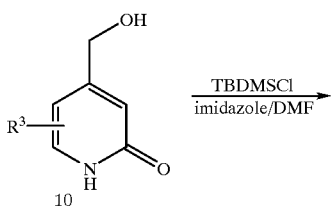

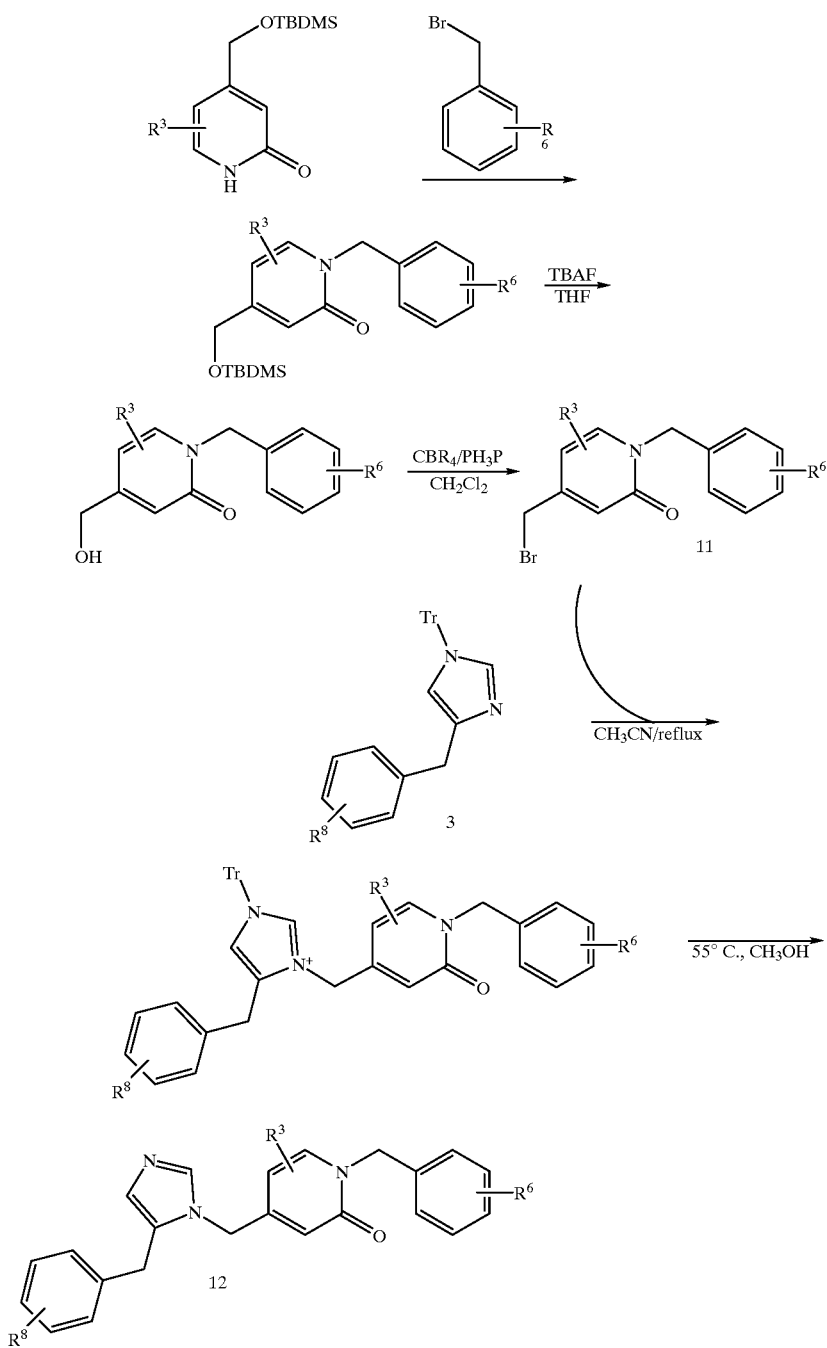
SCHEME 4
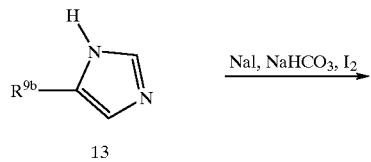

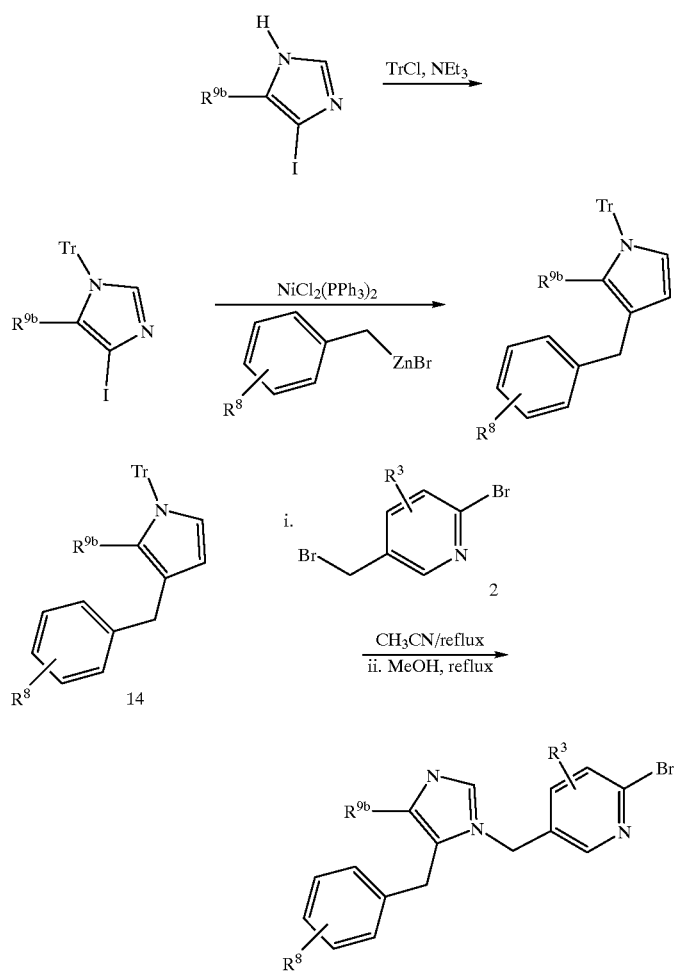
SCHEME 5
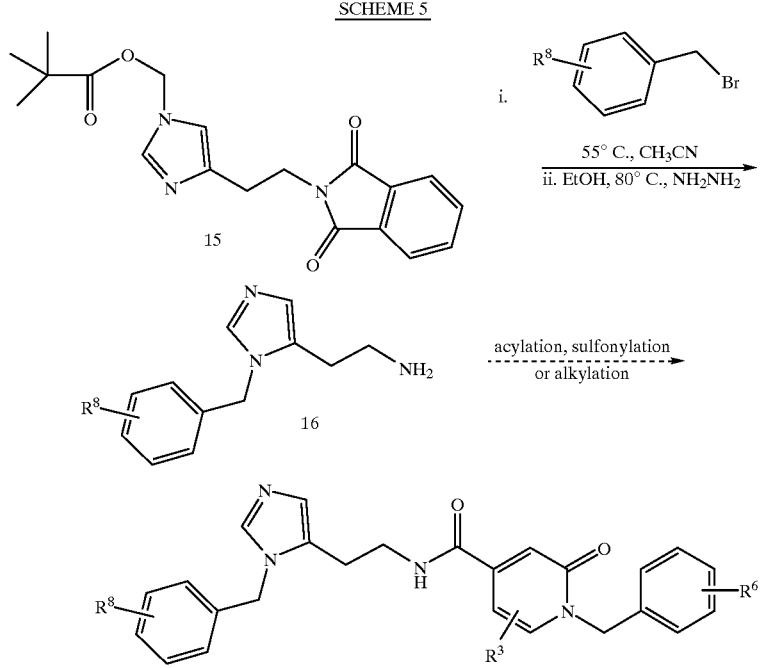

-continued
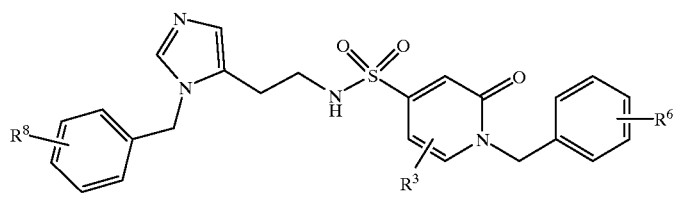
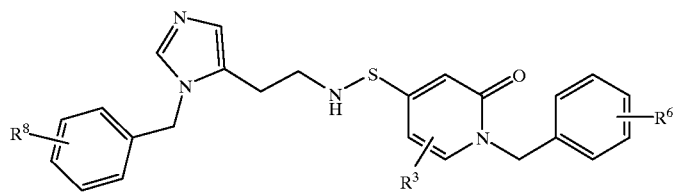
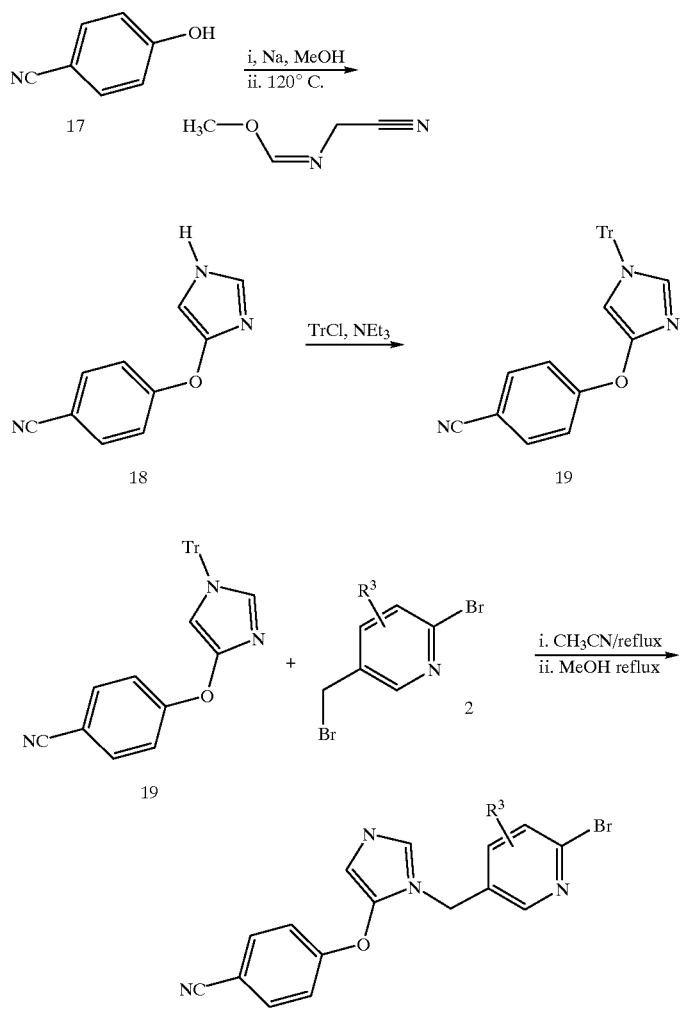

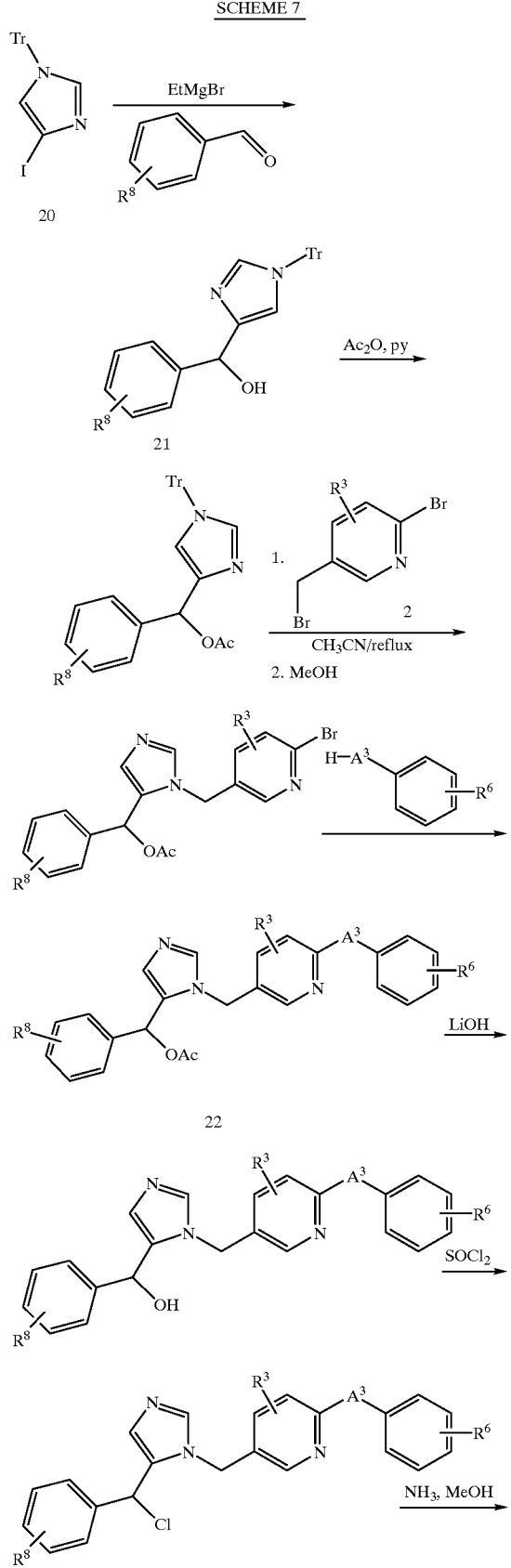
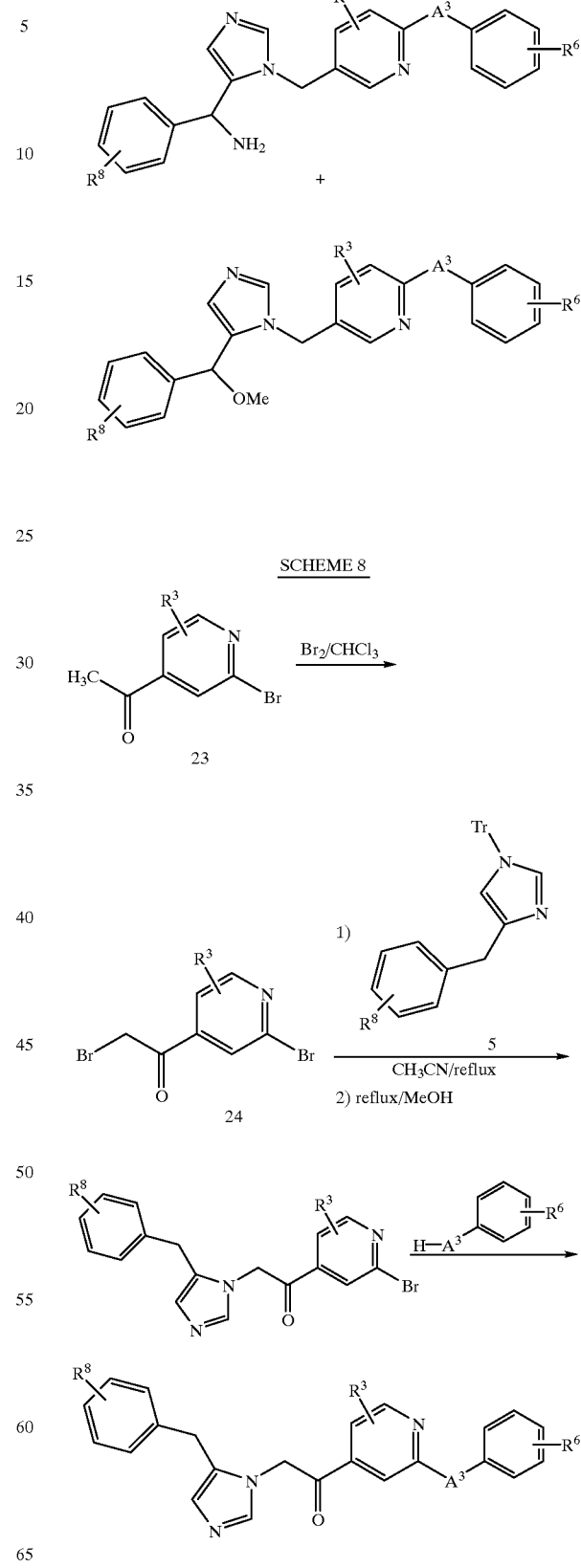

SCHEME 9

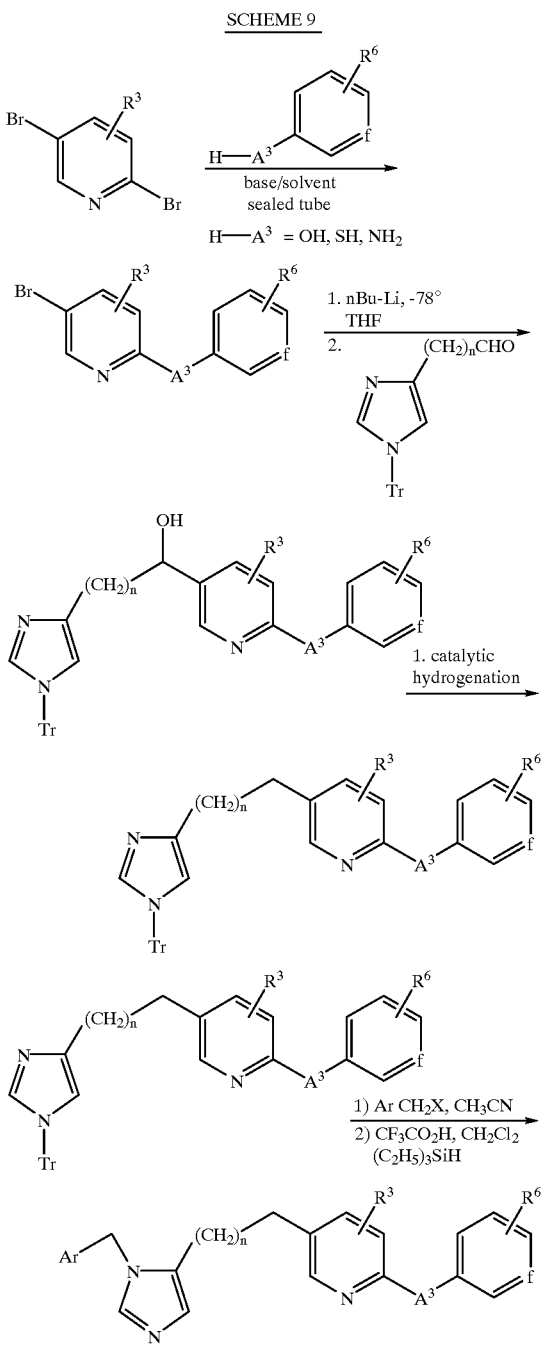

Schemes 10–18 illustrate reactions wherein the moiety

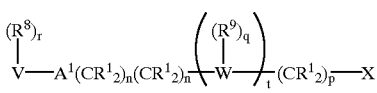

incorporated in the compounds of the instant invention is represented by other than the substituted imidazole-containing group illustrated in the previous Schemes.

Thus, the intermediates whose synthesis are illustrated in the above Schemes, and other pyridinonecarbocyclic and pyridinone-heterocyclic intermediates obtained commercially or readily synthesized, can be coupled with a variety of aldehydes. The aldehydes can be prepared by standard procedures, such as that described by O. P. Goel, U. Krolls, M. Stier and S. Kesten in *Organic Syntheses*, 1988, 67, 69–75, from the appropriate amino acid. Thus, as shown in Scheme 10, a suitably substituted bromopyridine is lithiated and is reacted with an aldehyde to provide the C-alkylated instant compound 27. Compound 27 can be deoxygenated by methods known in the art, such as a catalytic hydrogention, then deprotected with trifluoroacetic acid in methylene chloride to give the final compound 28. The compound 28 may be isolated in the salt form, for example, as a trifluoroacetate, hydrochloride or acetate salt, among others. The product diamine 28 can further be selectively protected to obtain 29, which can subsequently be reductively alkylated with a second aldehyde to obtain compound 30. Removal of the protecting group, and conversion to cyclized products such as the dihydroimidazole 31 can be accomplished by literature procedures.

If the bromopyridine reagent is reacted with an aldehyde which also has a protected hydroxyl group, such as 32 in Scheme 11, the protecting groups can be subsequently removed to unmask the hydroxyl group (Schemes 11, 12). The alcohol can be oxidized under standard conditions to e.g. an aldehyde, which can then be reacted with a variety of organometallic reagents such as alkyl lithium reagents, to obtain secondary alcohols such as 34. In addition, the fully deprotected amino alcohol 35 can be reductively alkylated (under conditions described previously) with a variety of aldehydes to obtain secondary amines, such as 36 (Scheme 12), or tertiary amines.

The Boc protected amino alcohol 33 can also be utilized to synthesize 2-aziridinylmethylarylheteroaryl such as 37 (Scheme 13). Treating 33 with 1,1'-sulfonyldiimidazole and sodium hydride in a solvent such as dimethylformamide led to the formation of aziridine 37. The aziridine is reacted with a nucleophile, such as a thiol, in the presence of base to yield the ring-opened product 38.

In addition, the arylpyridinone reagent can be reacted with aldehydes derived from amino acids such as O-alkylated yrosines, according to standard procedures, to obtain compounds such as 40, as shown in Scheme 14. When R' is an aryl group, 40 can first be hydrogenated to unmask the phenol, and the amine group deprotected with acid to produce 41. Alternatively, the amine protecting group in 40 can be removed, and O-alkylated phenolic amines such as 42 produced.

Schemes 15–18 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

Scheme 19 illustrates preparation of substituted aldehydes which incorporate the benzylimidazolyl sidechain. As set forth in Scheme 19, these aldehydes can be reductively aminated with various amines to give the instant compounds.

SCHEME 10
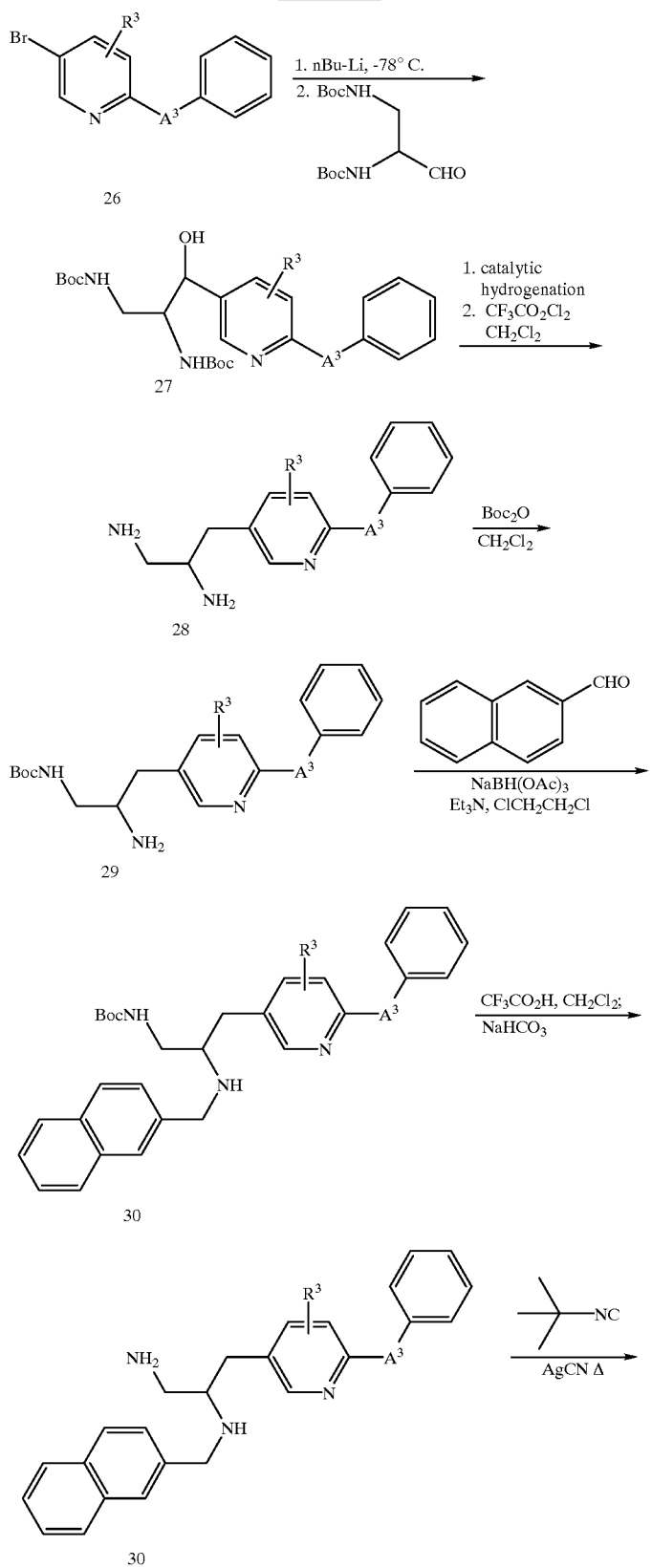

-continued
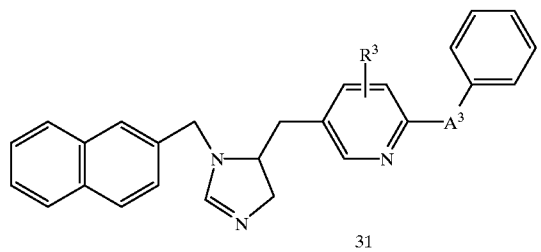
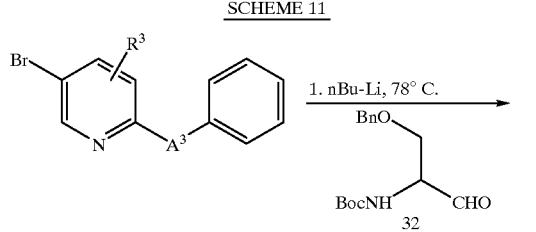
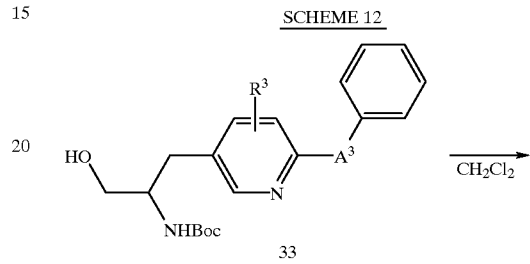
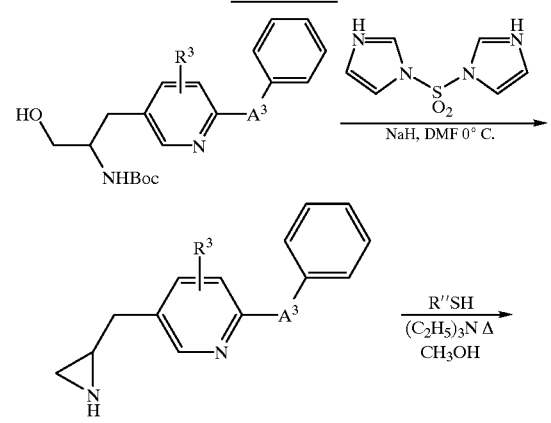

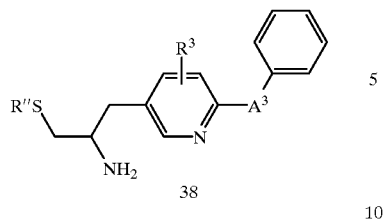
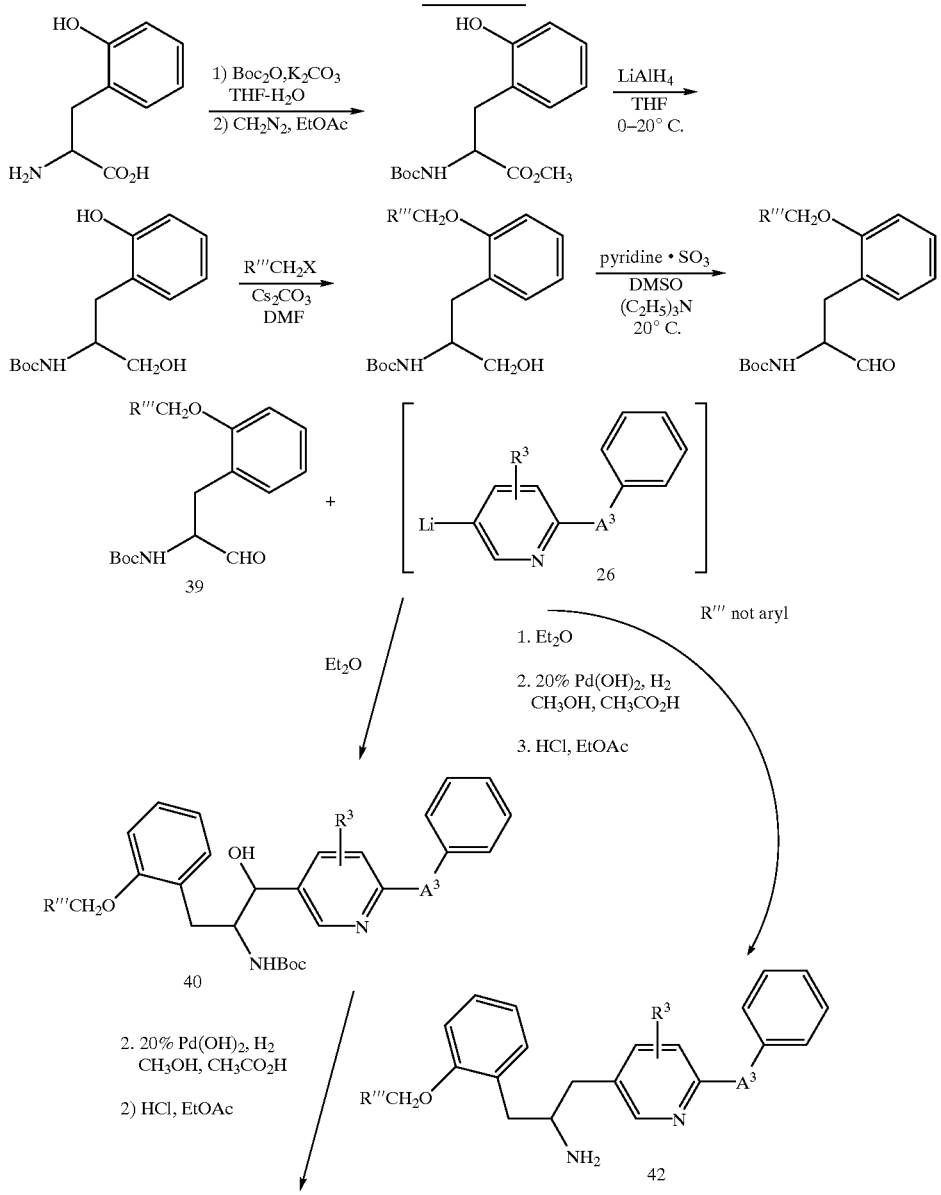
SCHEME 14

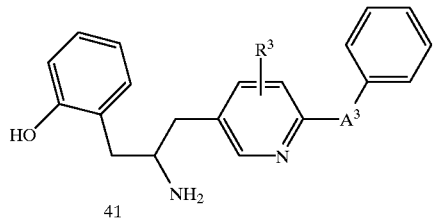
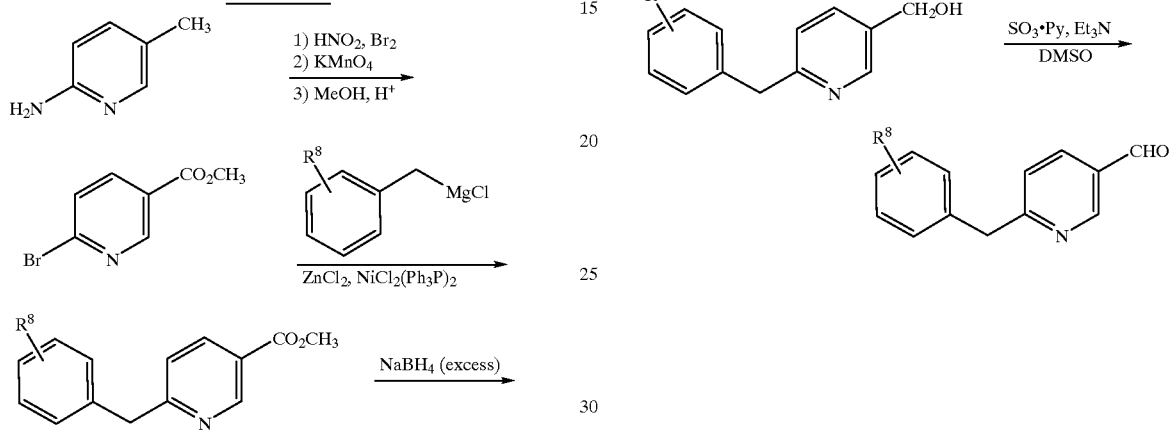
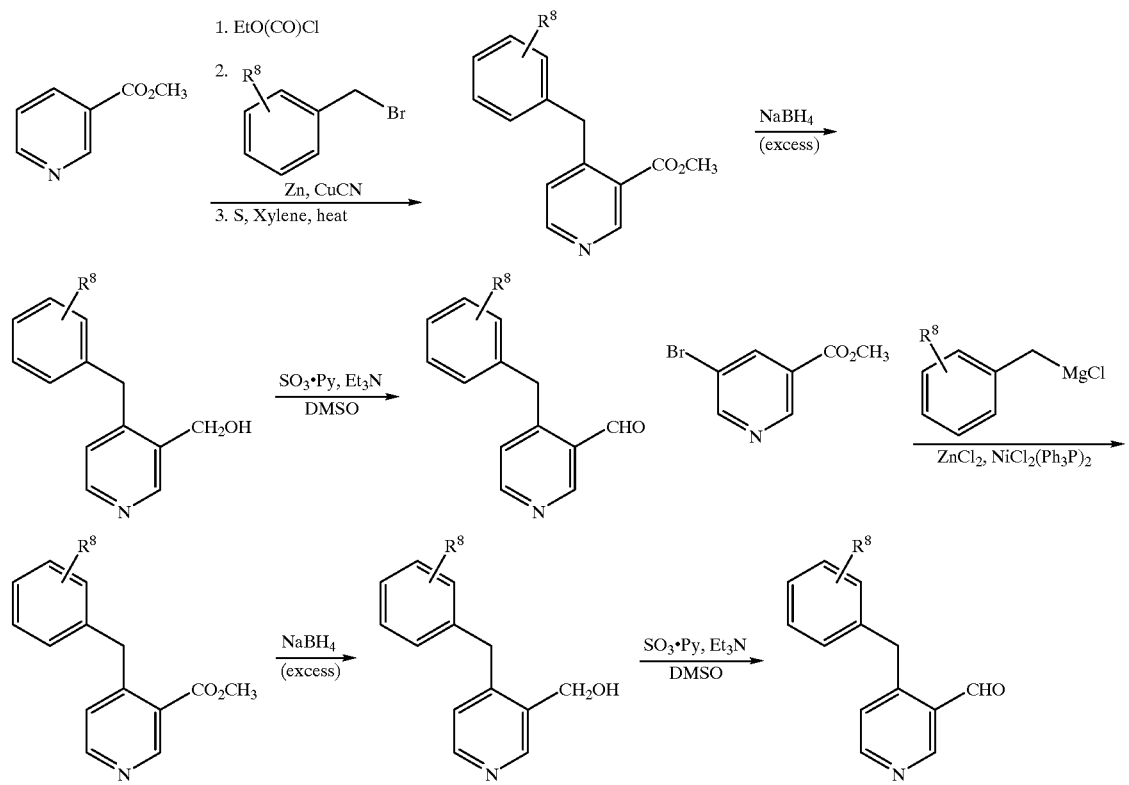

SCHEME 17
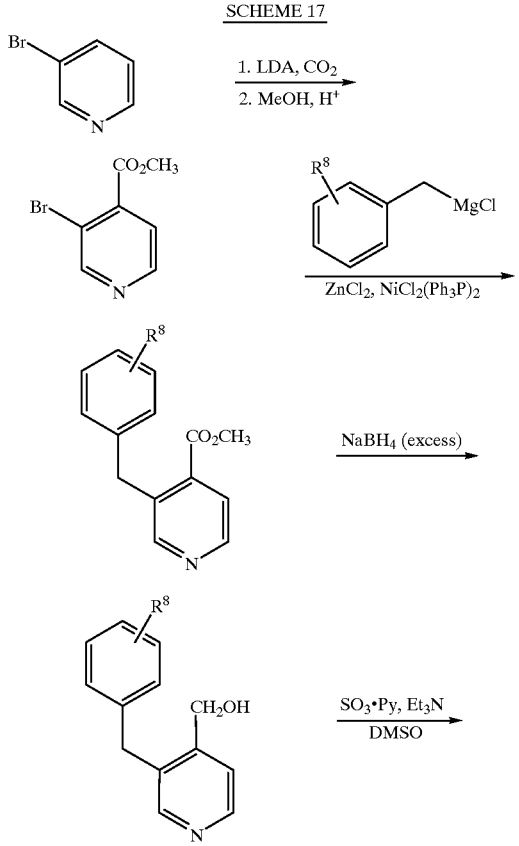
SCHEME 18
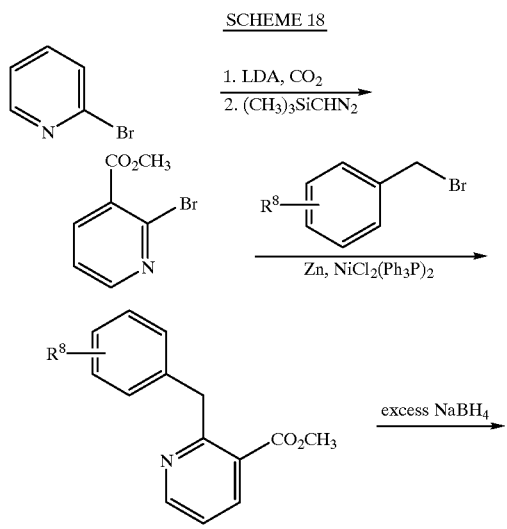
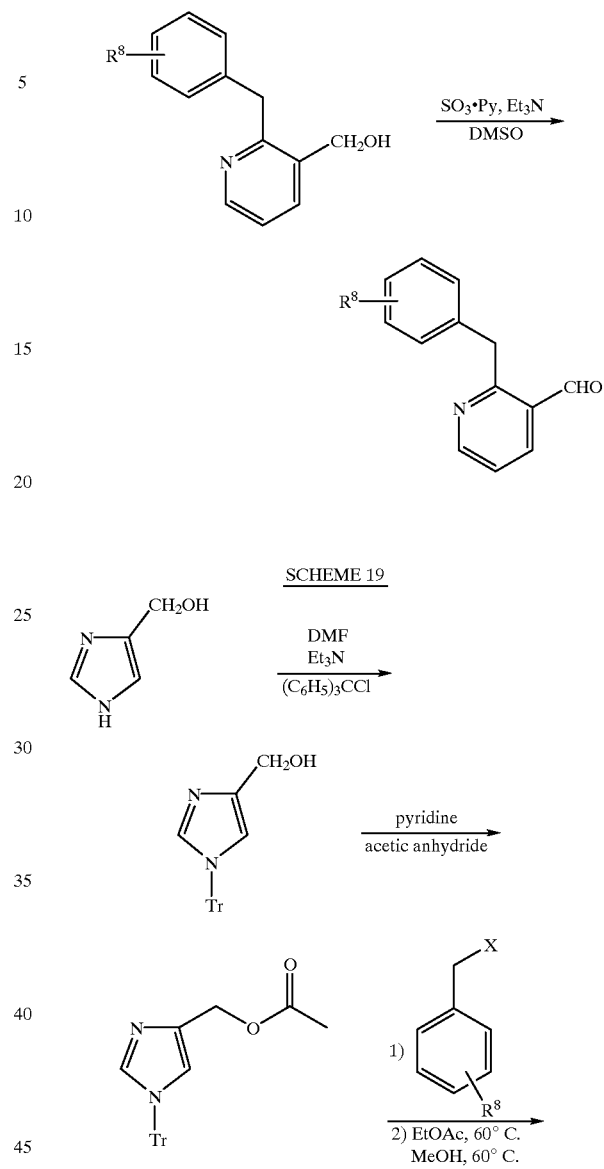
SCHEME 19
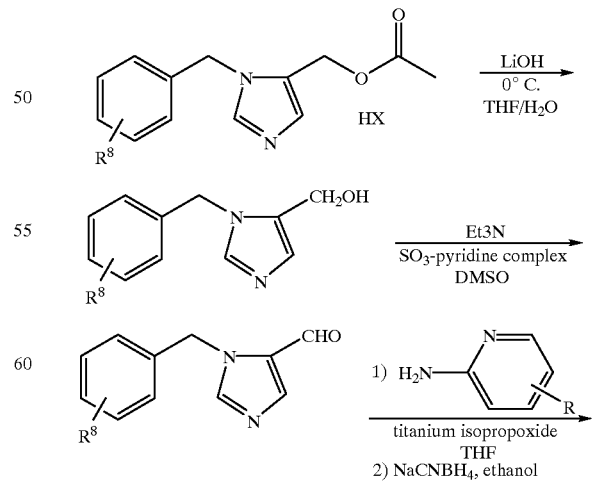

-continued

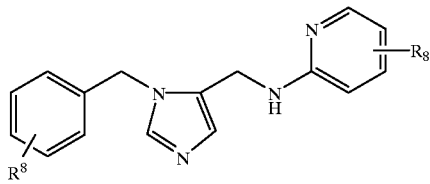

In a preferred embodiment of the instant invention the compounds of the invention are selective inhibitors of farnesyl-protein transferase. A compound is considered a selective inhibitor of farnesyl-protein transferase, for example, when its in vitro farnesyl-protein transferase inhibitory activity, as assessed by the assay described in Example 17, is at least 100 times greater than the in vitro activity of the same compound against geranylgeranyl-protein transferase-type I in the assay described in Example 19. Preferably, a selective compound exhibits at least 1000 times greater activity against one of the enzymatic activities when comparing geranylgeranyl-protein transferase-type I inhibition and farnesyl-protein transferase inhibition.

In another preferred embodiment of the instant invention the compounds of the invention are dual inhibitors of farnesyl-protein transferase and geranylgeranyl-protein transferase type I. Such a dual inhibitor will exhibit certain characteristics when assessed in in vitro assays, which are dependent on the type of assay employed.

In a SEAP assay, such as described in Example 21, it is preferred that the dual inhibitor compound has an in vitro inhibitory activity ($IC_{50}$) that is less than about 12 $\mu$M against K4B-Ras dependent activation of MAP kinases in cells. More preferably, the dual inhibitor compound has an in vitro inhibitory activity ($IC_{50}$) against K4B-Ras dependent activation of MAP kinases in cells which is more than about 5 times lower than the inhibitory activity ($IC_{50}$) against Myr-Ras dependent activation of MAP kinases in cells. Also more preferably, in a SEAP assay, the dual inhibitor compound has an inhibitory activity ($IC_{50}$) that is less than about 10 nM against H-Ras dependent activation of MAP kinases in cells.

In a GGTase plus anion assay, such as described in Example 19, it is preferred that the dual inhibitor compound has an in vitro inhibitory activity ($IC_{50}$) that is less than about 5 $\mu$M against transfer of a geranylgeranyl residue to a protein or peptide substrate comprising a CAAXG motif by geranylgeranyl-protein transferase type I in the presence of a modulating anion. More preferably, the dual inhibitor compound has an in vitro inhibitory activity ($IC_{50}$) that is less than about 1 $\mu$M against transfer of a geranylgeranyl residue to a protein or peptide substrate comprising a $CAAX^G$ motif by geranylgeranyl-protein transferase type I in the presence of a modulating anion. Preferably, the dual inhibitor compound has an in vitro inhibitory activity ($IC_{50}$) in the in vitro assay as described in Example 17 that is less than about 1 $\mu$M against transfer of a farnesyl residue to a protein or peptide substrate, comprising a $CAAX^F$ motif, by farnesyl-protein transferase. More preferably, the dual inhibitor compound has an in vitro inhibitory activity ($IC_{50}$) that is less than about 100 nM against transfer of a farnesyl residue to a protein or peptide substrate, comprising a $CAAX^F$ motif, by farnesyl-protein transferase. Also preferably, the dual inhibitor compound has an in vitro inhibitory activity ($IC_{50}$) in the in vitro assay as described in Example 20, that is less than about 100 nM against the anchorage independent growth of H-ras-transformed mammalian fibroblasts.

The protein or peptide substrate utilized in the instant assay may incorporate any CAAX motif that is geranylgeranylated by GGTase-I. The term "$CAAX^G$" will refer to such motifs that may be geranylgeranylated by GGTase-I. It is understood that some of the "$CAAX^G$" containing protein or peptide substrates may also be farnesylated by farnesyl-protein transferase. In particular such "$CAAX^G$" motifs include (the corresponding human protein is in parentheses): CVIM (K4B-Ras) (SEQ.ID.NO.: 1), CVLL (mutated H-Ras) (SEQ.ID.NO.: 2), CVVM (N-Ras) (SEQ.ID.NO.: 3), CIIM (K4A-Ras) (SEQ.ID.NO.: 4), CLLL (Rap-IA) (SEQ.ID.NO.: 5), CQLL (Rap-IB) (SEQ.ID.NO.: 6), CSIM (SEQ.ID.NO.: 7), CAIM (SEQ.ID.NO.: 8), CKVL (SEQ.ID.NO.: 9) and CLIM (PFX) (SEQ.ID.NO.: 10). Preferably, the CAAX motif is CVIM.

As used herein, the term "$CAAX^F$" is used to designate a protein or peptide substrate that incorporates four amino acid C-terminus motif that is farnesylated by farnesyl-protein transferase. It is understood that certain of the "$CAAX^F$" containing protein or peptide substrates may also be geranylgeranylated by GGTase-I. In particular such "$CAAX^F$" motifs include (the corresponding human protein is in parentheses): CVLS (H-ras) (SEQ.ID.NO.: 11), CVIM (K4B-Ras) (SEQ.ID.NO.: 1) and CVVM (N-Ras) (SEQ.ID.NO.: 3).

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, src, abl, lck, fyn) or by other mechanisms.

The compounds of the instant invention inhibit prenyl-protein transferase and the prenylation of the oncogene protein Ras. The instant compounds may also inhibit tumor angiogenesis, thereby affecting the growth of tumors (J. Rak et al. Cancer Research, 55: 4575–4580 (1995)). Such anti-angiogenesis properties of the instant compounds may also be useful in the treatment of certain forms of vision deficit related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. Science, 256:1331–1333 (1992).

The compounds of the instant invention are also useful in the prevention of restenosis after percutaneous transluminal coronary angioplasty by inhibiting neointimal formation (C. Indolfi et al. Nature medicine, 1:541–545(1995).

The instant compounds may also be useful in the treatment and prevention of polycystic kidney disease (D. L. Schaffner et al. American Journal of Pathology, 142:1051–1060 (1993) and B. Cowley, Jr. et al.FASEB Journal, 2: A3160 (1988)).

The instant compounds may also be useful for the treatment of fungal infections.

The instant compounds may also be useful as inhibitors of proliferation of vascular smooth muscle cells and therefore useful in the prevention and therapy of arteriosclerosis and diabetic vascular pathologies.

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethylcellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention may also be co-administered with other well known therapeutic agents that are selected for their particular usefulness against the condition that is being treated. For example, the compounds of the instant invention may also be co-administered with other well known cancer therapeutic agents that are selected for their particular usefulness against the condition that is being treated. Included in such combinations of therapeutic agents are combinations of the instant farnesyl-protein transferase inhibitors and an antineoplastic agent. It is also understood that such a combination of antineoplastic agent and inhibitor of farnesyl-protein transferase may be used in conjunction with other methods of treating cancer and/or tumors, including radiation therapy and surgery.

Examples of an antineoplastic agent include, in general, microtubule-stabilizing agents (such as paclitaxel (also known as Taxol®), docetaxel (also known as Taxotere®), epothilone A, epothilone B, desoxyepothilone A, desoxyepothilone B or their derivatives); microtubule-disruptor agents; alkylating agents, antimetabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

The preferred class of antineoplastic agents is the taxanes and the preferred antineoplastic agent is paclitaxel.

Radiation therapy, including x-rays or gamma rays which are delivered from either an externally applied beam or by implantation of tiny radioactive sources, may also be used in combination with the instant inhibitor of farnesyl-protein transferase alone to treat cancer.

Additionally, compounds of the instant invention may also be useful as radiation sensitizers, as described in WO 97/38697, published on Oct. 23, 1997, and herein incorporated by reference.

The instant compounds may also be useful in combination with other inhibitors of parts of the signaling pathway that links cell surface growth factor receptors to nuclear signals initiating cellular proliferation. Thus, the instant compounds may be utilized in combination with farnesyl pyrophosphate competitive inhibitors of the activity of farnesyl-protein transferase or in combination with a compound which has Raf antagonist activity. The instant compounds may also be co-administered with compounds that are selective inhibitors of geranylgeranyl protein transferase or farnesyl-protein transferase.

In particular, the compounds disclosed in the following patents and publications may be useful as farnesyl pyrophosphate-competitive inhibitor component of the instant composition: U.S. Ser. Nos. 08/254,228 and 08/435,047. Those patents and publications are incorporated herein by reference.

In practicing methods of this invention, which comprise administering, simultaneously or sequentially or in any order, two or more of a protein substrate-competitive inhibitor and a farnesyl pyrophosphate-competitive inhibitor, such administration can be orally or parenterally, including intravenous, intramuscular, intraperitoneal, subcutaneous, rectal and topical routes of administration. It is preferred that such administration be orally. It is more preferred that such administration be orally and simultaneously. When the protein substrate-competitive inhibitor and farnesyl pyrophosphate-competitive inhibitor are administered sequentially, the administration of each can be by the same method or by different methods.

The instant compounds may also be useful in combination with an integrin antagonist for the treatment of cancer, as described in U.S. Ser. No. 09/055,487, filed Apr. 6, 1998, which is incorporated herein by reference.

As used herein the term an integrin antagonist refers to compounds which selectively antagonize, inhibit or counteract binding of a physiological ligand to an integrin(s) that is involved in the regulation of angiogenisis, or in the growth and invasiveness of tumor cells. In particular, the term refers to compounds which selectively antagonize, inhibit or counteract binding of a physiological ligand to the αvβ3 integrin, which selectively antagonize, inhibit or counteract binding of a physiological ligand to the αvβ5 integrin, which antagonize, inhibit or counteract binding of a physiological ligand to both the αvβ3 integrin and the αvβ5 integrin, or which antagonize, inhibit or counteract the activity of the particular integrin(s) expressed on capillary endothelial cells. The term also refers to antagonists of the αvβ6, αvβ8, α1β1, α2β1, α5β1, α6β1 and α6β4 integrins. The term also refers to antagonists of any combination of αvβ3, αvβ5, αvβ6, αvβ8, α1β1, α2β1, α5β1, α6β1 and α6β4 integrins. The instant compounds may also be useful with other agents that inhibit angiogenisis and thereby inhibit the growth and invasiveness of tumor cells, including, but not limited to angiostatin and endostatin.

Similarly, the instant compounds may be useful in combination with agents that are effective in the treatment and prevention of NF-1, restenosis, polycystic kidney disease, infections of hepatitis delta and related viruses and fungal infections.

If formulated as a fixed dose, such combination products employ the combinations of this invention within the dosage range described below and the other pharmaceutically active agent(s) within its approved dosage range. Combinations of the instant invention may alternatively be used sequentially with known pharmaceutically acceptable agent(s) when a multiple combination formulation is inappropriate.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

5-(4'-Cyanobenzyl)-1-[2-(3"-methylphenylthio) pyrid-5-ylmethyl)imidazole

Step 1: 1-Trityl-4-(4-cyanobenzyl)imidazole

To an oven dried 500 ml flask was added Zn (92 mmol, 5.96 g) and then 45 mL of distilled THF via syringe. To this well stirred mixture was added 1,2-dibromoethane (9.2 mmol, 1.72 g) via pipet. This mixture was stirred at ambient temperature for 3 hr and then a solution of p-cyanobenzylbromide (59.5 mmol, 11.68 g) in THF (50 mL) was added via addition funnel over 20 minutes. The resulting mixture was stirred at ambient temperature for 6 hr. Then a mixture of 1-trityl-4-iodoimidazole (45.8 mmol, 20 g) and bis-triphenylphosphinedichloronickel (4.6 mmol, 3.0 g) was added. This was stirred at ambient temperature for 36 hr. A saturated ammonium chloride solution (125 mL) was added. Stirring was continued for 3 hr and then 1 L of chloroform was added to this mixture. The chloroform layer was drawn off, washed with dilute sodium bicarbonate then saturated sodium chloride. Dried with sodium sulfate and evaporated to a thick oil. Purified on a silica gel column eluted with chloroform to provide the title compound. $^1$H-NMR (CDCl$_3$): 4.0 ppm (s, 2H); 7.1–7.6 ppm (20H); 6.6 ppm(s, 1H).

Step 2: 2-bromo-5-bromomethyl pyridine

To a flask was charged 2-bromo-5-methylpyridine (34.9 mmol, 6.0 g), N-bromosuccinimide (38.4 mmol, 6.83 g), benzoyl peroxide (3.49 mmol, 0.85 g) and carbon tetrachloride (60 mL). This solution was refluxed for 6 hr, cooled to ambient temperature and purified on a silica gel column. Eluted with ethyl acetate: hexane (1:9) to provide the title compound. FAB MS: calc: 250.9 found: 251.9. $^1$H-NMR (CDCl$_3$): 4.4 ppm (s, 2H); 7.5 ppm (d, 1H); 7.6 ppm (d, 1H); 8.4 ppm (s, 1H).

Step 3: 5-(4-Cyanobenzyl)-1-(2-bromopyrid-5-ylmethyl) imidazole

To a flask was charged 1-trityl -4-p-cyanobenzyl imidazole (2.77 mmol, 1.18 g) from Step 1 and 2-bromo-5-bromomethyl pyridine (2.77 mmol, 0.67 g) from Step 2 in DMF (10 mL) and the mixture heated at 100° C. for 6 hr. The DMF was then removed in vacuo and the residue was triturated with ethyl ether. The ethyl ether was then decanted off and replaced with methanol (20 mL). This solution was then refluxed for 4 hr, cooled to ambient temperature and purified on a C$_{18}$ preperative hplc column to provide the title compound. High resolution FAB-MS: calc; 353.040183 found; 353.040183. $^1$H-NMR (CD$_3$OD): 4.2 ppm (s, 2H); 5.4 ppm (s, 2H); 7.2 and 7.6 ppm (d, 2H); 8.1 ppm (s, 1H); 9.1 ppm (s, 1H).

Step 4: 5-(4'-cyanobenzyl)-1-[2-(3"methylphenylthio)pyrid-5-ylmethyl)imidazole

The compound from Step 3 (0.28 mmol, 0.164 g), 3-methyl thiophenol (0.85 mmol, 0.106 g) and triethylamine (3.59 mmol, 0.36 g) were placed in an $N_2$ purged sealed tube. This was heated at 105° C. for 15 hr. The residue was dissolved in methanol and purified on a $C_{18}$ preperative hplc column. Lyophilized from dioxane/HCl to provide the title compound. FAB-MS: calc: 396.4 found: 397.2 $^1$H-NMR ($CD_3OD$): 2.4 ppm (s, 3H); 4.2 ppm (s, 2H); 5.4 ppm (s, 2H); 7.2–7.6 ppm (1OH); 8.1 ppm (s, 1H); 9.1 ppm (s, 1H).

Example 2

5-(4'-Cyanobenzyl)-1-[2-(3"-methylphenylphenoxy)-pyrid-5-ylmethyl)imidazole

The compound from Example 1 Step 3 (0.11 g 0.20 mmol), m-cresol (0.064 g, 0.59 mmol) and sodium hydride (60% dispersion in oil, 4.0 equiv, 0.032 g) were suspended in DMF (0.5 mL) in an $N_2$ purged sealed tube and heated at 110° C. for 24 hr. The residue was dissolved in methanol and purified on a $C_{18}$ preperative hplc column. Lyophilized from dioxane/HCl to provide the title compound. FAB-MS: calc: 380.4 found: 381.0. 2 $^1$H-NMR ($CD_3OD$): 2.4 ppm (s, 3H); 4.2 ppm (s, 2H); 5.4 ppm (s, 2H); 6.8–7.6 ppm (11H); 7.9 ppm (s, 1H); 9.1 ppm (s,1H).

Example 3

5-(4'-Cyanobenzyl)-1-[2-(3"-chlorophenylthio)pyrid-5-ylmethyl)]imidazole

The compound from Example 1 Step 3 (0.26 mmol, 0.090 g), 3-chloro phenol (0.76 mmol, 0.11 g) and triethylamine (0.726 g) were placed in an $N_2$ purged sealed tube. This was heated at 105° C. for 4 hr. The residue was dissolved in methanol and purified on a $C_{18}$ preperative hplc column. Lyophilized from dioxane/HCl to provide the title compound. FAB-MS: calc: 416.9 found:417.1. 2 $^1$H-NMR ($CD_3OD$): 4.2 ppm (s, 2H); 5.4 ppm (s, 2H); 6.9 ppm (d, 1H); 7.2–7.6 ppm (m, 10H); 8.1 ppm (s, 1H); 9.1 ppm (s, 1H).

Example 4

5-(4'-cyanobenzyl)-1-[2-(cyclohexylthio)pyrid-5-ylmethyl]imidazole

The compound from Example 1, Step 3 (0.16 g 0.45 mmol), cyclohexyl mercaptan (0.16 g, 1.35. mmol) and sodium hydride (60% dispersion in oil, 4.0 equiv, 0.032 g) were suspended in DMF (0.5 mL) in an $N_2$ purged sealed tube and heated at 110° C. for 4hr. The residue was dissolved in methanol and purified on a $C_{18}$ preperative hplc column. Lyophilized from dioxane/HCl to provide the title compound. FAB-MS: calc: 389 found: 389. $^1$H-NMR ($CD_3OD$): 1.4–2.1 ppm (10H); 3.8 ppm (1H); 4.2 ppm (2H); 5.45 ppm (2H); 7.2–7.6 ppm (7H); 8.2 ppm (1H); 9.1 ppm (1H).

Example 5

5-(4'-Cyanobenzyl)-1-[2-(3"-methylphenylthio) pyrid-4-ylmethyl)]imidazole

Step 1: 2-Bromo-4-bromomethyl pyridine

Following the procedure of Adams et.al. (J. Am. Chem. Soc., 76, 3168 (1954)) 2-bromo-4-methylpyridine was obtained from 2-amino-4-methylpyridine. $^1$H-NMR ($CDCl_3$): 2.3 ppm (s, 3H); 7.05 ppm (d, 1H); 7.3 ppm (s, 1H); 8.2 ppm (s, 1H).

Step 2: 5-(4'-Cyanobenzyl)-1-(2-bromo-4-pyridylmethyl) imidazole

Following the procedure in Example 1, Step 2 the product was obtained from 2-bromo-4-methylpyridine. FAB-MS: calc: 249 found: 250. $^1$H-NMR ($CDCl_3$): 4.4 ppm (s, 2H); 7.2 ppm (d, 1H); 7.5 ppm (s, 1H); 8.4 ppm (d, 1H).

Step 3: 5-(4'-cyanobenzyl)-1-[2-bromopyrid-4-ylmethyl)] imidazole

Following the procedure in Example 1, Step 3 1-trityl-4-p-cyanobenzyl imidazole and 2-bromo-4-bromomethyl pyridine were reacted to give the product as a free base solid after washing the preparative hplc purified material with $Na_2CO_3$. FAB-MS: calc: 353 found:353. $^1$H-NMR ($CDCl_3$): 3.8 ppm (s, 2H); 4.9 ppm (s, 2H); 6.8 ppm (d, 1H); 6.9–7.6 (7H); 8.3 ppm (d, 1H).

Step 4: 5-(4'-cyanobenzyl)-1-[2-(3"methylphenylthio)4-pyridylmethyl)]imidazole

Following the procedure in Example 1, Step 4, 5-(4'-cyanophenyl)-1-[2-bromopyrid-4-ylmethyl)]imidazole and 3-methyl thiophenol were reacted and the product was obtained. FAB-MS: calc: 396.5 found: 397.1. $^1$H-NMR ($CD_3OD$): 2.4 ppm (s, 3H); 4.05 ppm(s, 2H); 5.5 ppm (s, 2H); 6.3 ppm (s, 1H); 7.0 ppm (d,1H); 7.2–7.6 ppm (9H); 8.35 ppm (d, 1H); 9.02 ppm (s, 1H).

Example 6

5-(4'-Cyanobenzyl)-1-[2-(cyclohexylamino)pyrid-5-ylmethyl)]imidazole hydrochloride Step 1: 2- cyclohexylamino-5-pyridine carboxylic acid 2-Chloro-5-pyridinecarboxylicacid ethylester (g,,5.0 mMol) was treated with 10 mMol cyclohexylamine and the mixture heated for 6 hours at 100° in a sealed tube. Preparative HPLC of the crude product gave the title compound along with equal amounts of the N-cyclohexylamide of the starting ester.

Step 2: (2- cyclohexylamino-5-pyridyl)methanol

The product from Step 1 was reduced with 3 equivalents of $LiAlH_4$ in THF for 4 hours at room temperature. Lithium salts were precipitated with water and aqueous NaOH. The THF layer was filtered through FILTER -AID and the filtrate conc in vac to give 2-cyclohexylamino-5-pyridine methanol.

Step 3: 5-(4'-cyanobenzyl)-1-[2-(cyclohexylamino)pyrid-5-ylmethyl)]imidazole hydrochloride The product from Step 2 was treated with 1.1 equivalent of triphenylphosphine in refluxing CBr. The crude 2-cyclohexylamino-5-dissolved pyridylmethyl bromide was purified by silica gel chromatography and reacted with 1-trityl-4-(4-cyanobenzyl)imidazole from Example 1, Step 1 for 12 hours at 60° in dry acetonitrile. The mixture was concentrated and the residue boiled 12 hours in methanol The methanol was concentrated andthe residue purified by preparative HPLC to give the trifluoroacetic salt of the title compound, This was converted to the HCl salt by lyophilization: from dioxane containing 1 equivalent of HCl.

Example 7

5-(4'-Cyanobenzyl) 1-[2-(3"-chlorophenylthio)pyrid-5-ylmethyl]imidazole -S-oxide hydrochloride.

The product of Example 1 was oxidized with 1.1 equivalent of 3-chloroperbenzoic acid in THF at -60° to room temperature. Preparative HPLC followed by lyophilization from dioxane HCl gave pure title compound.

Example 8

Preparation of 2-[N-(1-(4'-Cyanobenzyl)-1H-imidazol-5-ylethyl)carbamoyl]-6-(3-trifluoromethylphenoxy)pyridine Step A: 4-Cyanobenzyl histamine $N^\tau$-Pivaloyloxymethyl-$N^\alpha$-phthaloylhistamine (4.55 g, 12.8 mmol) prepared as previously described (J. C. Emmett, F. H. Holloway, and J. L. Turner, *J. Chem. Soc., Perkin Trans. 1*, 1341, (1979)) and α-Bromo-p-tolunitrile (3.77 g, 19.2 mmol) were dissolved in acetonitrile (70 mL) and heated at 55° C. for 4 h, cooled to room temperature, and filtered to remove the white solid. The acetonitrile (30 mL) was concentrated to ½ its volume under reduced pressure and the solution was heated at 55° C. overnight. The solution was cooled and filtered to give a white solid. The solids were combined, dried, and used without further purification.

1-Pivaloyloxymethyl-3-(4-cyanobenzyl)-4-(2-phthalimidoethyl) imidazolium bromide (1.00 g, 1.81 mmol) was dissolved in ethanol (50 mL), treated with hydrazine (0.287 mL, 9.06 mmol), and heated at reflux for 16 h. Dimethyl phthalate (2.22 mL, 13.57 mmol) was added and reflux was continued for 6 h. The reaction mixture was cooled in an ice-$H_2O$ bath, the solid precipitate filtered off, the filtrate concentrated to dryness, and the residue chromatographed ($SiO_2$, $CH_2Cl_2(NH_4OH)$: 3–8% $CH_3OH$) to give the title compound. $^1H$ NMR ($CD_3OD$) δ 7.76 (s, 1H), 7.74 (d, 2H, J=8 Hz), 7.27 (d, 2H, J=8 Hz), 6.88 (s, 1H), 5.35 (s, 2H), 2.76 (t, 2H, J=6 Hz), 2.60 (t, 2 H, J=6 Hz).

Step B: 2-[N-(1-(4'-Cyanobenzyl)-1H-imidazol-5-ylethyl)carbamoyl]-6-(3-trifluoromethylphenoxy)pyridine 6-(3-Trifluoromethylphenoxy)pyridine-2-carboxylic acid (0.05 g, 0.146 mmol) was dissolved in DMF (2 mL) and treated with EDC (0.0338 g, 0.176 mmol), HOBT (0.0238 g, 0.176 mmol), 4-cyanobenzyl histamine (0.0399 g, 0.176 mmol) and N-methylmorpholine (0.048 mL, 0.438 mmol) and stirred at ambient temperature for 18 hr. Purification of the crude reaction by preparative RP HPLC on a Vydac column gave the title compound.

Anal. calcd for $C_{26}H_{20}N_5O_2F_3$•1.35 $CF_3CO_2H$•0.5 $H_2O$: C, 52.67; H, 3.44; N, 10.70; Found: C, 52.67; H, 3.42; N, 10.76. FAB MS 492 (M+1).

Using the procedure described above, but substituting the requisite acids in Step B, the following compounds were prepared: 3-[N-(1-(4'-Cyanobenzyl)-1H-imidazol-5-ylethyl)carbamoyl]-6-(3-trifluoromethylphenoxy)pyridine Anal. calcd for $C_{26}H_{20}N_5O_2F_3$•0.3 $H_2O$: C, 62.84; H, 4.18; N, 14.10; Found: C, 62.80; H, 4.09; N, 13.97. FAB MS 492 (M+1).

3-[N-(1-(4'-Cyanobenzyl)-1H-imidazol-5-ylethyl)carbamoyl]-5-(3-trifluoromethylphenoxy)pyridine Anal. calcd for $C_{26}H_{20}N_5O_2F_3$•0.15 $CH_2Cl_2$: C, 62.29; H, 4.06; N, 13.89; Found: C, 62.68; H, 4.44; N, 13.51. FAB MS 492 (M+1).

3-[N-(1-(4'-Cyanobenzyl)-1H-imidazol-5-ylethyl)carbamoyl]-5-(3-trifluoromethylbenzyloxy)pyridine Anal. calcd for $C_{27}H_{22}N_5O_2F_3$•0.20 $H_2O$: C, 63.69; H, 4.44; N, 13.76; Found: C, 63.70; H, 4.48; N, 13.67. FAB MS 506 (M+1).

Example 9

Preparation of 5-chloro-1-(3-chlorobenzyl)-2-oxo-1,2-dihydro-pyridine-3-carboxylic acid {2-[3-(4-cyanobenzyl)-3H-imidazol-4-yl]ethyl }-amide 5-Chloro-1-(3-chlorobenzyl)-2-oxo-1,2-dihydropyridine-3-carboxylic acid (0.10 g, 0.335 mmol) was dissolved in DMF (10 mL) and treated with EDC (0.077 g, 0.402 mmol), HOBT (0.054 g, 0.402 mmol), 4-cyanobenzyl histamine (0.079 g, 0.352 mmol) and NMM (0.11 mL, 1.00 mmol) and stirred at ambient temperature for 18 hr. The reaction mixture was concentrated to remove the DMF, then partitioned between EtOAc and aq saturated $NaHCO_3$ solution, the organic layer separated, washed with brine and dried ($MgSO_4$). The title compound was obtained upon purification by RP HPLC on a PrepPak column eluting with an acetonitrile/$H_2O$/TFA gradient followed by neutralization with $NaHCO_3$ and extraction.

Anal. calcd for $C_{26}H_{21}N_5O_2Cl_2$•0.20 $H_2O$: C, 61.23; H, 4.23; N, 13.73; Found: C, 61.19; H, 4.20; N, 13.59. FAB MS 506 (M+1).

Using the procedure described above, but substituting the requisite acids, the following compounds were prepared: 1-(3-Chlorobenzyl)-2-oxo-1,2-dihydro-pyridine-3-carboxylic acid {2-[3-(4-cyanobenzyl)-3H-imidazol-4-yl]-ethyl }-amide Anal. calcd for $C_{26}H_{22}N_5O_2Cl$•0.45 $H_2O$: C, 65.05; H, 4.81; N, 14.59; Found: C, 65.12; H, 4.84; N, 14.35. FAB MS 472 (M+1).

1-(3-Trifluoromethylbenzyl)-2-oxo-1,2-dihydro-pyridine-5-carboxylic acid {2-[3-(4-cyanobenzyl)-3H-imidazol-4-yl]-ethyl }-amide Anal. calcd for $C_{27}H_{22}N_5O_2F_3$•0.40 $H_2O$: C, 63.25; H, 4.48; N, 13.66; Found: C, 63.30; H, 4.26; N, 13.32. FAB MS 506 (M+1).

1-(3-Chlorobenzyl)-2-oxo-1,2-dihydro-pyridine-5-carboxylic acid {2-[3-(4-cyanobenzyl)-3H-imidazol-4-yl]-ethyl }-amide Anal. calcd for $C_{26}H_{22}N_5O_2Cl$•0.30$H_2O$: C, 65.41; H, 4.77; N, 14.67; Found: C, 65.42; H, 4.64; N, 14.42. FAB MS 472 (M+1).

5-Chloro-1-(3-chlorobenzyl)-2-oxo-1,2-dihydro-pyridine-5-carboxylic acid {2-[3-(4-cyanobenzyl)-3H-imidazol-4-yl]-ethyl }-amide Anal. calcd for $C_{26}H_{21}N_5O_2Cl_2$•0.75 $H_2O$: C, 60.06; H, 4.36; N, 13.47; Found: C, 60.08; H, 4.11; N, 13.32. FAB MS 506 (M+1).

Example 10

Preparation of 6-[N-(3-Chlorobenzyl) carbamoyl]-4-ethoxy-pyridine-2-carboxylic acid {2-[3-(4-cyanobenzyl)-3H-imidazol-4-yl]-ethyl }-amide Step A: Diethyl 4-hydroxy-2,6-pyridine dicarboxylate Chelidamic acid (15.1 g, 0.825 mol), abs EtOH (48 mL) and concd $H_2SO_4$ (0.9 mL) were combined and heated at reflux for 8 hr. The reaction mixture was concentrated to remove the EtOH, and partitioned between EtOAc and $H_2O$. After numerous extractions, concentration of the organic layer, the title compound was obtained after RP HPLC.

Step B: Mono methyl ester of 4-ethoxy-2,6-pyridine dicarboxylate

The diethyl ester (0.300 g, 1.12 mmol) was dissolved in THF (4 mL) and treated with LiOH (0.052 g, 1.23 mmol) in $H_2O$/$CH_3OH$ (24 mL) and stirred overnight at ambient temperature. The title compound was obtained after preparative RP HPLC. FAB MS 226 (M+1).

Step C: 4-Ethoxy-6-methoxycarbonyl-pyridine-2-carboxylic acid {2-[3-(4-cyanobenzyl)-3H-imidazol-4-yl]-ethyl }-amide The mono methyl ester of 4-ethoxy-2,6-pyridine dicarboxylate (0.098 g, 0.435 mmol) was dissolved in DMF (1 mL) and treated with EDC (0.108 g, 0.503 mmol), HOBT (0.062 g, 0.456 mmol), 4-cyanobenzylhistamine (0.098 g, 0.435 mmol) and the pH adjusted to 7.5 with NMM. After stirring overnight at ambient temperature, the reaction mixture was concentrated to remove the DMF, then chromatographed on RP HPLC to give the title compound as the TFA salt. FAB MS 434 (M+1).

Step D: 4-Ethoxy-6-carboxyl-pyridine-2-carboxylic acid {2-[3-(4-cyanobenzyl)-3H-imidazol-4-yl]-ethyl }-amide 4-Ethoxy-6-methoxycarbonyl-pyridine-2-carboxylic acid {2-[3-(4-cyanobenzyl)-3H-imidazol-4-yl]-ethyl}-amide (0.249 g, 0.376 mmol) was dissolved in THF (2 mL) and treated with LiOH (0.052 g, 1.24 mmol) in $CH_3OH$ (4 mL)-$H_2O$ (2 mL) with stirring at ambient temperature for 5 hr. The reaction mixture was concentrated to dryness and used in the next step.

Step E: 6-[N-(3-Chlorobenzyl) carbamoyl]-4-ethoxy-pyridine-2-carboxylic acid {2-[3-(4-cyanobenzyl)-3H-imidazol-4-yl]ethyl }-amide 4-Ethoxy-6-carboxyl-pyridine-2-carboxylic acid {2-[3-(4-cyanobenzyl)-3H-imidazol-4-yl]-ethyl}-amide (0.120 g, 0.185 mmol) was dissolved in DMF (2 mL) and treated with EDC (0.043 g, 0.222 mmol), HOBT (0.024 g, 0.176 mmol), 3-chlorobenzylamine (0.113 mL, 0.925 mmol) and the pH adjusted to 7.5 with NMM. After stirring overnight at ambient temperature, the reaction mixture was concentrated to remove the DMF, the residue partitioned between EtOAc and aq saturated $NaHCO_3$ solution, the organic layer separated, washed with brine and dried ($MgSO_4$). Filtration and concentration gave the crude product which was chromatographed on RP HPLC to give the title compound as the TFA salt.

Anal. calcd for $C_{29}H_{27}N_6O_3Cl$•2.5 $CF_3CO_2H$•1.15 $H_2O$: C, 48.11; H, 3.78; N, 9.90; Found: C, 48.10; H, 3.79; N, 9.69. FAB MS 543 (M+1).

Example 11

Preparation of 6-[N-(3-Chlorophenyl) carbamoyl]-4-ethoxy-pyridine-2-carboxylic acid {2-[3-(4-cyanobenzyl)-3H-imidazol-4-yl]-ethyl }-amide 4-Ethoxy-6-carboxyl-pyridine-2-carboxylic acid {2-[3-(4-cyanobenzyl)-3H-imidazol-4-yl]-ethyl }-amide (0.124 g, 0.191 mmol) was dissolved in DMF (2 mL), treated with Bop reagent (0.093 g, 0.210 mmol) and NMM (0.083 mL, 0.764 mmol) and stirred overnight at ambient temperature. The solvent was removed in vacuo and the residue partitioned between EtOAc and aq saturated $NaHCO_3$ solution. The organic layer was separated, washed with brine and dried ($MgSO_4$). Filtration and concentration gave the title compound after chromatography ($CH_2Cl_2$ with 1% $CH_3OH$ then 4.5% $CH_3OH$/0.5% $NH_4OH$).

Anal. calcd for $C_{28}H_{25}N_6O_3Cl$•0.70 $CF_3CO_2H$•1.15 $H_2O$: C, 56.09; H, 4.48; N, 13.35; Found: C, 56.10; H, 4.52; N, 13.31. FAB MS 529 (M+1).

Example 12

Preparation of 4-(3-Chlorobenzyloxy)-6-methoxycarbonyl-pyridine-2-carboxylic acid {2-[3-(4-cyanobenzyl)-3H-imidazol-4-yl]-ethyl}-amide Step A: 4-(3-Chlorobenzyloxy)-pyridine-2,6-dicarboxylic acid Chelidamic acid (10.0 g, 0.055 mol) was dissolved in $CH_3OH$ (300 mL), treated with concd $H_2SO_4$ (1.8 mL) and heated at reflux for 6 hr, then cooled and concentrated to give an amber oil.

Step B: Dimethyl 4-(3-Chlorobenzyloxy)-pyridine-2,6-dicarboxylate 4-(3-Chlorobenzyloxy)-pyridine-2,6-dicarboxylic acid (2.00 g, 9.47 mmol) was dissolved in DMF (19 mL) and treated with $K_2CO_3$ (3.93 g, 28.4 mmol) and 3-chlorobenzylbromide (1.24 mL, 9.47 mmol). After stirring overnight at ambient temperature, the solvent was removed in vacuo and the residue partitioned between EtOAc and aq saturated $NaHCO_3$ solution. The organic layer was separated, washed with brine and dried ($Na_2SO_4$). Filtration and concentration gave the title compound.

Step C: Mono methyl ester of 4-(3-Chlorobenzyloxy)-pyridine-2,6-dicarboxylic acid The dimethyl ester (3.18 g, 9.46 mmol) was dissolved in THF (10 mL) and treated with LiOH (0.4372 g, 10.41 mmol) in $H_2O/CH_3OH$: 1/3 (200 mL) and stirred overnight at ambient temperature. The title compound was obtained after preparative RP HPLC.

Step D: 4-(3-Chlorobenzyloxy)-6-methoxycarbonyl-pyridine-2-carboxylic acid {2-[3-(4-cyanobenzyl)-3H-imidazol-4-yl]ethyl }-amide The mono methyl ester of 4-(3-chlorobenzyloxy)-pyridine-2,6-dicarboxylic acid (0.236 g, 0.622 mmol) was dissolved in DMF (2 mL) and treated with EDC (0.125 g, 0.653 mmol), HOBT (0.080 g, 0.59 mmol), 4-cyanobenzylhistamine (0.141 g, 0.622 mmol) and the pH adjusted to 7.5 with NMM. After stirring overnight at ambient temperature, the reaction mixture was concentrated to remove the DMF, the residue partitioned between EtOAc and aq saturated $NaHCO_3$ solution, the organic layer separated, washed with brine and dried ($MgSO_4$). Filtration and concentration gave the crude product which was chromatographed on RP HPLC to give the title compound which was isolated as the HCl salt.

Anal. calcd for $C_{28}H_{24}N_5O_4Cl$•HCl•0.55 $H_2O$: C, 58.35; H, 4.56; N, 12.15; Found: C, 58.33; H. 4.73; N, 11.87. FAB MS 530 (M+1).

Example 13

Preparation of 4-(5-{[6-(3-chloro-phenoxy)-pyridin-2-ylamino]methyl}-imidazol-1-ylmethyl)-benzonitrile Step A: 1-Triphenylmethyl-4-(hydroxvmethyl)-imidazole To a solution of 4-(hydroxymethyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B: 1-Triphenylmethyl-4-(acetoxymethyl)-imidazole

Alcohol from Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO3, and brine, then dried ($Na_2SO_4$), filtered, and concentrated in vacuo to provide the crude product. The acetate was isolated as a white powder which was sufficiently pure for use in the next reaction.

Step C: 1-(4-Cyanobenzyl)-5-(acetoxymethyl)-imidazole hydrobromide

A solution of the product from Step B (85.8 g, 225 mmol) and α-bromo-p-tolunitrile (50.1 g, 232 mmol) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid which was used in the next step without further purification.

Step D: 1-(4-Cyanobenzyl)-5-(hydroxymethyl)-imidazole

To a solution of the acetate from Step C (50.4 g, 150 mmol) in 1.5 L of 3:1 THF/water at 0° C. was added lithium hydroxide monohydrate (18.9 g, 450 mmol). After one hour, the reaction was concentrated in vacuo, diluted with EtOAc (3 L), and washed with water, sat. aq. $NaHCO_3$ and brine. The solution was then dried ($Na_2SO_4$), filtered, and concentrated in vacuo to provide the crude product as a pale yellow fluffy solid which was sufficiently pure for use in the next step without further purification.

Step E: 1-(4-Cyanobenzyl)-5-imidazolecarboxaldehyde

To a solution of the alcohol from Step D (21.5 g, 101 mmol) in 500 mL of DMSO at room temperature was added triethylamine (56 mL, 402 mmol), then $SO_3$-pyridine complex (40.5 g, 254 mmol). After 45 minutes, the reaction was poured into 2.5 L of EtOAc, washed with water (4×1 L) and brine, dried (Na2SO$_4$), filtered, and concentrated in vacuo to provide the aldehyde as a white powder which was sufficiently pure for use in the next step without further purification.

Step F: 2-Amino-6-(3-chlorophenoxy)-pyridine

A mixture of 2-acetylamino-6-bromopyridine (200 mg, 0.93 mmol), 3-chlorophenol (240 mg, 1.86 mmol), $CSCO_3$ (606 mg, 1.86 mmol), copper (II) triflate benzene complex (10 mg, 0.02 mmol), 1-naphthoic acid (321 mg, 1.86 mmol), ethyl acetate (5 mg, 00.5 mmol), and freshly activated powdered 4-angstrom mol. sieves (250 mg) in 2 mL dry toluene was heated with stirring at 110° C. in a sealed tube for 72 hours. The mixture was cooled and filtered through a Celite pad, and the filtrate concentrated in vacuo. The crude oil was redissolved in ethyl acetate and was washed twice with 20% aq. NaOH solution. The organic layer was dried over anhydrous $MgSO_4$ and was filtered and concentrated to give a yellow oil. The oil was purified by gravity column chromatography over silica gel with 4:1 hexanes/ethyl acetate. Suspected product fractions were combined and concentrated in vacuo to give the product as a yellow oil. The oil was dissolved in 2 mL of 10% aq. sulfuric acid, and the solution heated at 100° C. for 18 hours. The reaction was cooled and basified to pH 11 with concentrated $NH_4OH$ solution, and extracted twice with ethyl acetate. The combined ethyl acetate extracts were washed with brine, dried over anhydrous $MgSO_4$, filtered and concentrated to give the title product as an oil. 400 Mhz $H^1$ NMR ($CDCl_3$): 4.44(br s, 2H), 6.15(d, 1H), 6.21(d, 1H), 7.02(d, 1H), 7.11(m, 2H), 7.28(m, 1H), 7.42(t, 1H).

Step G: 1-(4-Cyanobenzyl)imidazole-5-[6-(3-chlorophenoxy)pyridin-2-yl]methanamide A mixture of 1-(4-cyanobenzyl)imidazole-5-carboxaldehyde (79 mg, 0.37 mmol) from Step E, 2-amino-6-(3-chlorophenoxy)-pyridine (81 mg, 0.37 mmol) from Step F, and titanium isopropoxide (131 mg, 0.46 mmol) in 0.50 mL of anhydrous THF was stirred vigorously at room temperature in an argon atmosphere for 1 hour. The reaction was diluted with 0.50 mL of anhydrous ethanol and was treated with sodium cyanoborohydride (23 mg, 0.37 mmol). The resulting mixture was stirred at room temperature for 18 hours. The reaction was concentrated in vacuo, and the residue partitioned between ethyl acetate and water. The aqueous layer was reextracted twice with ethyl acetate, and combined extracts washed with brine and dried over anhydrous $MgSO_4$. Filtration and concentration provided the product as a yellow oil. The crude product was purified by reverse phase preparatory LC to give the pure desired product as a tacky white amorphous powder after lyophilization from water. 400 Mhz $H^1$ NMR ($CDCl_3$): 4.37(s, 2H), 5.31(s, 2H), 6.18(d, 1H), 6.25(d, 1H), 6.94(d, 1H), 7.09(s, 1H), 7.18(d, 2H), 7.19(d, 1H), 7.21(s, 1H), 7.30(m, 1H), 7.42(t, 1H), 7.64(d, 2H), 8.46(s, 1H). High res. FAB MS: theo.=416.1273, obs.=416.1286. Elemental analysis for $C_{23}H_{18}N_5OCl$•0.60 water•1.15TFA: C(54.47 calc., 54.44 obs.); H (3.68 calc., 3.72 obs.); N(12.56 calc., 1.54 obs.).

Example 14

Preparation of 4-(5-{[6-(phenylethynyl)-pyridin-2-ylamino]-methyl}imidazol-1-ylmethyl)-benzonitrile Step A: 2-Amino-6-(1-phenylethyn-2-yl)pyridine A solution of 2-amino-6-bromopyridine (200 mg, 1.16 mmol), 1-phenylacetylene (142 mg, 1.39 mmol), bis(triphenylphosphine) palladium (II) chloride (14 mg, 0.02 mmol), and CuI (2 mg, 0.01 mmol) in 2 mL triethylamine was stirred at 60° C. in a sealed tube for 18 hours. The reaction was cooled and concentrated in vacuo to a dark oil. The oil was purified by gravity column chromatography over silica gel with 2% methanol/chloroform to give the desired product as a brown oil. 400 Mhz $H^1$ NMR ($CDCl_3$): 4.57(br s, 2H), 6.49(d, 1H), 6.93(d, 1H), 7.38(m, 3H), 7.41(t, 1H), 7.58(d, 1H).

Step B: 1-(4-Cyanobenzyl)imidazole-5-[6-(1-phenylethyn-2-yl)pyridin-2-yl]methanamine Via a procedure identical to that described above in Example 13, Step G, from 100 mg (0.47 mmol) of aldehyde (from Example 13, Step E) and 92 mg (0.47 mmol) of 2-amino-6-(1-phenylethyn-2-yl)pyridine (from Step A) the desired product was obtained as an amorphous tacky light yellow powder. 400 Mhz $H^1$ NMR ($CDCl_3$): 4.50(s, 2H), 5.61(s, 2H), 6.71(d, 1H), 6.89(d, 1H), 7.23(d, 2H), 7.38–7.48(complex, 4H), 7.62(d, 2H), 7.65–7.73(complex, 4H), 7.78(t, 1H), 8.58(s, 1H), 10.90(br s, 1H). High res. FAB MS: theo=390.3713, obs.=390.1728. Elemental analysis for $C_{25}H_{19}N_5$•1.00 water•2.5TFA: C(calc. 43.36, obs. 43.63); H(calc. 3.42, obs. 3.61); N(calc. 10.11, obs. 9.85).

Example 15

Preparation of 4-(5-{[6-(1,2,3,4-tetrahydronaphth-6-yloxy)-pyridin-2-ylamino]-methyl}-imidazol-1-ylmethyl)-benzonitrile Step A: 2-Amino-6-(1,2,3,4-tetrahydronaphthyloxy-6-yl)pyridine Via an identical procedure to that described in Example 13, Step F, from 200 mg (0.93 mmol) of 2-acetylamino-6-bromopyridine and 276 mg (1.86 mmol) of 6-hydroxy-(1, 2,3,4-tetrahydro)naphthylene was obtained the title compound as an oil. 400 Mhz H$^1$ NMR (CDCl$_3$): 1.79(d, 4H), 2.77(d, 4H), 6.56(d, 1H), 6.81(d, 1H), 7.04(d, 1H), 7.65(t, 1H), 7.84(d, 1H), 8.12(s, 1H).

Step B: 1-(4-Cyanobenzyl)imidazole-5-[6-(1,2,3,4-tetrahydronaphthyloxy-6-yl)pyridin-2-yl]methanamine Via a procedure identical to that described in Example 13, Step G from 132 mg (0.62 mmol) of aldehyde (from Example 13, Step E) and 148 mg (0.62 mmol) of 2-amino-6-(1,2,3,4-tetrahydronaphthyloxy-6-yl)pyridine (from Step A) was obtained the desired product as a clear oil. 400 Mhz H$^1$ NMR (CDCl$_3$): 1.81(m, 4H), 2.77(m, 4H), 4.43(s, 2H), 5.53(s, 2H), 6.03(d, 1H), 6.18(m, 1H), 6.85(s, 1H), 7.14(d, 1H), 7.25(d, 2H), 7.46(s, 1H), 7.56(t, 1H), 7.66(d, 2H), 8.61(s, 1H). High res. FAB MS: theo.=436.2132, obs.=436.2143.

Example 16

Preparation of 4-(5-{[6-(2-phenylethyl)-pyridin-2-ylamino]-methyl}-imidazol-1-ylmethyl)-benzonitrile A solution of 1-(4-cyanobenzyl)imidazole-5-[6-(1-phenylethyn-2-yl)-2-pyridyl]methanamine•2.5TFA (85 mg, 0.13 mmol) from Example 14, Step B in 10 mL of absolute EtOH over 10% Pd on C catalyst (20 mg) was hydrogenated for 18 hours at atmospheric pressure (balloon). The catalyst was removed by filtration, and the filtrate was concentrated in vacuo to give an oil. The crude oil was purified via reversed phase preparatory LC to give the desired product as an oil/foam. 400 Mhz H$^1$ NMR (CDCl$_3$): 2.98(dd, 2H), 3.02(dd, 2H), 4.38(d, 2H), 5.49(d, 2H), 6.59(d, 2H), 7.16–7.37(complex, 7H), 7.62(complex, 3H), 7.76(t, 1H), 8.52(s, 1H). FAB MS: M+=390.

Example 17
In vitro Inhibition of Ras Farnesyl Transferase

Assays of farnesyl-protein transferase. Partially purified bovine FPTase and Ras peptides (Ras-CVLS (SEQ.ID.NO.: 11), Ras-CVIM (SEQ.ID.NO.: 1) and Ras-CAIL (SEQ.ID.NO.: 12)) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0 M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM ZnCl$_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention described in the above Examples 1–16 were tested for inhibitory activity against human FPTase by the assay described above and were found to have IC$_{50}$ of <50 μM.

Example 18
In vivo Ras Farnesylation Assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 19
Modified in vitro GGTase Inhibition Asssay

The modified geranylgeranyl-protein transferase inhibition assay is carried out at room temperature. A typical reaction contains (in a final volume of 50 μL): [$^3$H] geranylgeranyl diphosphate, biotinylated Ras peptide, 50 mM HEPES, pH 7.5, a modulating anion (for example 10 mM glycerophosphate or 5 mM ATP), 5 mM MgCl$_2$, 10 μM ZnCl$_2$, 0.1% PEG (15–20,000), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ.ID.NO.: 13). Reactions are initiated by the addition of GGTase and stopped at timed intervals (typically 15 min) by the addition of 200 μL of a 3 mg/mL suspension of streptavidin SPA beads (Scintillation Proximity Assay beads, Amersham) in 0.2 M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25-fold into the enzyme assay mixture. IC$_{50}$ values are determined with Ras peptide near $K_M$ concentrations. Enzyme and nonsaturating substrate conditions for inhibitor $IC_{50}$ determinations are as follows: 75 pM GGTase-I, 1.6 μM Ras peptide, 100 nM geranylgeranyl diphosphate.

Example 20
Cell-based in vitro Growth Inhibition Assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of $1\times10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

Example 21
Construction of SEAP Reporter Plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI was constructed by Deborah Jones (Merck) and contains 5 sequential copies of the 'dyad symmetry response element' cloned upstream of a 'CAT-TATA' sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoRI and HpaI. The ends of the linear DNA fragments were filled in with the Klenow fragment of E. coli DNA Polymerase I. The 'blunt ended' DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Klenow DNA Polymerase I. The SEAP DNA fragment was blunt end ligated into the pCMV-RE-AKI vector and the ligation products were transformed into DH5-alpha E. coli cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Cloning of a Myristylated Viral-H-ras Expression Plasmid

A DNA fragment containing viral-H-ras can be PCRed from plasmid "H-1" (Ellis R. et al. J. Virol. 36, 408, 1980) using the following oligos.
Sense Strand:
5'TCTCCTCGAGGCCACCATGGGGAGTAG-CAAGAGCAAGCCTAA GGACCCCAGCCAGCGC-CGGATGACAGAATACAAGCTTGTGGTG G 3'. (SEQ.ID.NO.: 14)

Antisense:
5'CACATCTAGATCAGGACAGCACAGACTTGCAGC 3'. (SEQ.ID.NO.: 15)

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site. To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3'end. The XhoI-XbaI fragment can be ligated into the mammalian expression plasmid pCI (Promega) cut with XhoI and XbaI. This results in a plasmid in which the recombinant myr-viral-H-ras gene is constitutively transcribed from the CMV promoter of the pCI vector.

Cloning of a Viral-H-ras-CVLL Expression Plasmid

A viral-H-ras clone with a C-terminal sequence encoding the amino acids CVLL can be cloned from the plasmid "H-1" (Ellis R. et al. J. Virol. 36, 408, 1980) by PCR using the following oligos.
Sense Strand:
5'TCTCCTCGAGGCCACCATGACAGAATACAAGC-TTGTGGTGG-3' (SEQ.ID.NO.: 16)
Antisense Strand:
5'CACTCTAGACTGGTGTCAGAGCAGCACACACTT-GCAGC-3' (SEQ.ID.NO.: 17)

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid in which the mutated viral-H-ras-CVLL gene is constitutively transcribed from the CMV promoter of the pCI vector.

Cloning of c-H-ras-Leu61 Expression Plasmid

The human c-H-ras gene can be PCRed from a human cerebral cortex cDNA library (Clontech) using the following oligonucleotide primers.
Sense strand:
5'-GAGAGAATTCGCCACCATGACGGAATATAAGCT-GGTGG-3' (SEQ.ID.NO.: 18)
Antisense Strand:
5'-GAGAGTCGACGCGTCAGGAGAGCACACACTT-GC-3' (SEQ.ID.NO.: 19)

The primers will amplify a c-H-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-H-ras fragment can be ligated ligated into an EcoRI -Sal I cut mutagenesis vector pAlter-1 (Promega). Mutation of glutamine-61 to a leucine can be accomplished using the manufacturer's protocols and the following oligonucleotide:
5'-CCGCCGGCCTGGAGGAGTACAG-3' (SEQ.ID.NO.: 20)

After selection and sequencing for the correct nucleotide substitution, the mutated c-H-ras-Leu61 can be excised from the pAlter-1 vector, using EcoRI and Sal I, and be directly ligated into the vector pCI (Promega) which has been digested with EcoRI and Sal I. The new recombinant plasmid will constitutively transcribe c-H-ras-Leu61from the CMV promoter of the pCI vector.

Cloning of a c-N-ras-Val-12 Expression Plasmid

The human c-N-ras gene can be PCRed from a human cerebral cortex cDNA library (Clontech) using the following oligonucleotide primers.

Sense Strand:
5'-GAGAGAATTCGCCACCATGACTGAGTACAAAC-GGTGG-3' (SEQ.ID.NO.: 21)
Antisense Strand:
5'-GAGAGTCGACTTGTTACATCACCACACATGGC-3' (SEQ.ID.NO.: 22)

The primers will amplify a c-N-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-N-ras fragment can be ligated into an EcoRI -Sal I cut mutagenesis vector pAlter-1 (Promega). Mutation of glycine-12 to a valine can be accomplished using the manufacturer's protocols and the following oligonucleotide:
5'-GTTGGAGCAGTTGGTGTTGGG-3' (SEQ.ID.NO.: 23)

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid will constitutively transcribe c-N-ras-Val-12 from the CMV promoter of the pCI vector Cloning of a c-K-ras-Val-12 Expression Plasmid The human c-K-ras gene can be PCRed from a human cerebral cortex cDNA library (Clontech) using the following oligonucleotide primers.
Sense Strand:
5'-GAGAGGTACCGCCACCATGACTGAATATAAAC-TTGTGG-3' (SEQ.ID.NO.: 24)
Antisense Strand:
5'-CTCTGTCGACGTATTTACATAATTACACACTTT-GTC-3' (SEQ.ID.NO.: 25)

The primers will amplify a c-K-ras encoding DNA fragment with the primers contributing an optimized 'Kozak' translation start sequence, a KpnI site at the N-terminus and a Sal I stite at the C-terminal end. After trimming the ends of the PCR product with Kpn I and Sal I, the c-K-ras fragment can be ligated into a KpnI -Sal I cut mutagenesis vector pAlter-1 (Promega). Mutation of cysteine-12 to a valine can be accomplished using the manufacturer's protocols and the following oligonucleotide:
5'-GTAGTTGGAGCTGTTGGCGTAGGC-3' (SEQ.ID. NO.: 26)

After selection and sequencing for the correct nucleotide substitution, the mutated c-K-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K-ras-Val-12 from the CMV promoter of the pCI vector.

SEAP Assay

Human C33A cells (human epitheial carcenoma—ATTC collection) are seeded in 10cm tissue culture plates in DMEM+10% fetal calf serum+1xPen/Strep+1xglutamine+1xNEAA. Cells are grown at 37° C. in a 5% $CO_2$ atmosphere until they reach 50 –80% of conflunecy.

The transient transfection is performed by the $CaPO_4$ method (Sambrook et al., 1989). Thus, expression plasmids for H-ras, N-ras, K-ras, Myr-ras or H-ras-CVLL are co-precipitated with the DSE-SEAP reporter construct. For 10 cm plates 600 µl of $CaCl_2$-DNA solution is added dropwise while vortexing to 600 µl of 2xHBS buffer to give 1.2 ml of precipitate solution (see recipes below). This is allowed to sit at room temperature for 20 to 30 minutes. While the precipitate is forming, the media on the C33A cells is replaced with DMEM (minus phenol red; Gibco cat. #31053-028)+0.5% charcoal stripped calf serum+1Xx(Pen/Strep, Glutamine and nonessential aminoacids). The $CaPO_4$-DNA precipitate is added dropwise to the cells and the plate rocked gently to distribute. DNA uptake is allowed to proceed for 5–6 hrs at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum+1x(Pen/Strep, Glutamine and NEAA). Transfected cells are plated in a 96 well microtiter plate (100 µl/well) to which drug, diluted in media, has already been added in a volume of 100 µl. The final volume per well is 200 µl with each drug concentration repeated in triplicate over a range of half-log steps.

Incubation of cells and drugs is for 36 hrs at 37° under $CO_2$. At the end of the incubation period, cells are examined microscopically for evidence of cell distress. Next, 100 µl of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 µl media is combinRased with 200 µl of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

| DNA-$CaPO_4$ precipitate for 10 cm. plate of cells | |
| --- | --- |
| Ras expression plasmid (1 µg/µl) | 10 µl |
| DSE-SEAP Plasmid (1 µg/µl) | 2 µl |
| Sheared Calf Thymus DNA (1 µg/µl) | 8 µl |
| 2M $CaCl_2$ | 74 µl |
| $dH_2O$ | 506 µl |
| 2X HBS Buffer | |
| 280 mM NaCl | |
| 10 mM KCl | |
| 1.5 mM $Na_2HPO_4$ $2H_2O$ | |
| 12 mM dextrose | |
| 50 mM HEPES | |
| Final pH = 7.05 | |
| Luminesence Buffer (26 ml) | |
| Assay Buffer | 20 ml |
| Emerald Reagent ™ (Tropix) | 2.5 ml |
| 100 mM homoarginine | 2.5 ml |
| CSPD Reagent ® (Tropix) | 1.0 ml |

Assay Buffer
Add 0.05M $Na_2CO_3$ to 0.05M $NaHCO_3$ to obtain pH 9.5. Make 1 mM in $MgCl_2$ Example 22
In vivo growth inhibition assay To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of $1 \times 10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound of the formula $A^1$:

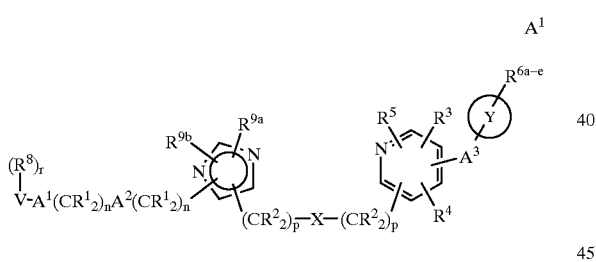

$A^1$ wherein:

Y is a 5, 6 or 7 membered carbocyclic ring;

$R^1$ and $R^2$ are independently selected from:
   a) hydrogen,
   b) aryl, $C_3-C_{10}$ cycloalkyl, $C_2-C_6$ alkenyl, $C_2-C_6$ alkynyl, $R^{10}O-$, $R^{11}S(O)_m-$, $R^{10}C(O)NR^{10}-$, $R^{11}C(O)O-$, $(R^{10})_2NC(O)-$, $R^{10}{}_2N-C(NR^{10})-$, CN, $NO_2$, $R^{10}C(O)-$, $N_3$, $-N(R^{10})_2$, or $R^{11}OC(O)NR^{10}-$,
   c) unsubstituted or substituted $C_1-C_6$ alkyl wherein the substituent on the substituted $C_1-C_6$ alkyl is selected from unsubstituted or substituted aryl, $C_3-C_{10}$ cycloalkyl, $C_2-C_6$ alkenyl, $C_2-C_6$ alkynyl, $R^{10}O-$, $R^{11}S(O)_m-$, $R^{10}C(O)NR^{10}-$, $(R^{10})_2NC(O)-$, $R^{10}{}_2N-C(NR^{10})-$, CN, $R^{10}C(O)-$, $N_3$, $-N(R^{10})_2$, and $R^{11}OC(O)-NR^{10}-$;

$R^3$, $R^4$ and $R^5$ are independently selected from:
   a) hydrogen,
   b) unsubstituted or substituted aryl, $C_3-C_{10}$ cycloalkyl, $C_2-C_6$ alkenyl, $C_2-C_6$ alkynyl, halogen, $C_1-C_6$ perfluoroalkyl, $R^{12}O-$, $R^{11}S(O)_m-$, $R^{10}C(O)NR^{10}-$, $(R^{10})_2NC(O)-$, $R^{11}C(O)O-$, $R^{10}{}_2N-C(NR^{10})-$, CN, $NO_2$, $R^{10}C(O)-$, $N_3$, $-N(R^{10})_2$, or $R^{11}OC(O)NR^{10}-$,
   c) unsubstituted $C_1-C_6$ alkyl,
   d) substituted $C_1-C_6$ alkyl wherein the substituent on the substituted $C_1-C_6$ alkyl is selected from unsubstituted or substituted aryl, $C_3-C_{10}$ cycloalkyl, $C_2-C_6$ alkenyl, $C_2-C_6$ alkynyl, $R^{12}O-$, $R^{11}S(O)_m-$, $R^{10}C(O)NR^{10}-$, $(R^{10})_2NC(O)-$, $R^{10}{}_2N-C(NR^{10})-$, CN, $R^{10}C(O)-$, $N_3$, $-N(R^{10})_2$, and $R^{11}OC(O)-NR^{10}-$;

$R^{6a}$, $R^{6b}$, $R^{6c}$, $R^{6d}$ and $R^{6e}$ are independently selected from:
   a) hydrogen,
   b) unsubstituted or substituted aryl, $C_3-C_{10}$ cycloalkyl, $C_2-C_6$ alkenyl, $C_2-C_6$ alkynyl, halogen, $C_1-C_6$ perfluoroalkyl, $R^{12}O-$, $R^{11}S(O)_m-$, $R^{10}C(O)NR^{10}-$, $(R^{10})_2NC(O)-$, $R^{11}C(O)O-$, $R^{10}{}_2N-C(NR^{10})-$, CN, $NO_2$, $R^{10}C(O)-$, $(R^{10})_2NS(O)_2-$, $R^{11}S(O)_mNR^{10}-$, $N_3$, $-N(R^{10})_2$, or $R^{11}OC(O)NR^{10}-$,
   c) unsubstituted $C_1-C_6$ alkyl,
   d) substituted $C_1-C_6$ alkyl wherein the substituent on the substituted $C_1-C_6$ alkyl is selected from unsubstituted or substituted aryl, $C_3-C_{10}$ cycloalkyl, $C_2-C_6$ alkenyl, $C_2-C_6$ alkynyl, $R^{12}O-$, $R^{11}S(O)_m-$, $R^{10}C(O)NR^{10}-$, $(R^{10})_2NC(O)-$, $(R^{10})_2NS(O)_2-$, $R^{11}S(O)_mNR^{10}-$, $R^{10}{}_2N-C(NR^{10})-$, CN, $R^{10}C(O)-$, $N_3$, $-N(R^{10})_2$, and $R^{11}OC(O)-NR^{10}-$; or any two of, $R^{6a}$, $R^{6b}$, $R^{6c}$, $R^{6d}$ and $R^{6e}$ on adjacent carbon atoms are combined to form a diradical selected from $-CH=CH-CH=CH-$, $-CH=CH-CH_2-$, $-(CH_2)_4-$ and $-(CH_2)_3-$;

$R^7$ is selected from: H; $C_{1-4}$ alkyl, $C_{3-6}$ cycloalkyl, aryl, aroyl, arylsulfonyl, unsubstituted or substituted with:

a) $C_{1-4}$ alkoxy,
b) aryl c)

(acetyl group with $R^{11}$)

d) —$SO_2R^{11}$
e) $N(R^{10})_2$ or
f) $C_{1-4}$ perfluoroalkyl;

$R^8$ is independently selected from:
  a) hydrogen,
  b) aryl, substituted aryl, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $(R^{10})_2NS(O)_2$—, $R^{11}S(O)_mNR^{10}$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—, and
  c) $C_1$–$C_6$ alkyl unsubstituted or substituted by aryl, cyanophenyl, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, $(R^{10})_2NC(O)$—, $(R^{10})_2NS(O)_2$—, $R^{11}S(O)_mNR^{10}$—, $R^{10}{}_2N$—$C(NR^{10})$—, CN, $R^{10}C(O)$—, $N_3$, —$N(R^{10})_2$, or $R^{10}OC(O)NH$—;

$R^9$ is independently selected from:
  a) hydrogen,
  b) alkenyl, alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—, and
  c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, or $R^{11}OC(O)NR^{10}$—;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, aryl, substituted aryl, $C_1$–$C_6$ perfluoroalkyl, 2-aminoethyl and 2,2,2-trifluoroethyl;

$R^{13}$ is selected from hydrogen, $C_1$–$C_6$ alkyl, cyano, $C_1$–$C_6$ alkylsulfonyl and $C_1$–$C_6$ acyl;

$A^1$ and $A^2$ are independently selected from: a bond, —CH=CH—, —C≡C—, —C(O)—, —C(O)$NR^{10}$—, —$NR^{10}C(O)$—, O, —$N(R^{10})$—, —$S(O)_2N(R^{10})$—, —$N(R^{10})S(O)_2$—, or $S(O)_m$;

$A^3$ is selected from: —$CH_2$—, —$CH_2CH_2$—, —C≡C—, O, —$N(R^{10})$—, $S(O)_m$, —$C(O)NR^{10}$—, —$NR^{10}C(O)$—, —$CH_2C(O)NR^{10}$—, —$CH_2NR^{10}C(O)$—, —$C(O)NR^{10}CH_2$—, —$NR^{10}C(O)CH_2$—, —$CH_2O$—, —$CH_2N(R^{10})$—, —$CH_2S(O)_m$—, —$OCH_2$—, —$N(R^{10})CH_2$— and —$S(O)_mCH_2$—;

V is selected from: aryl,

X is a bond, —CH=C—, O, —C(=O)—, —C(O)$NR^7$—, —$NR^7C(O)$—, —C(O)O—, —OC(O)—, —C(O)$NR^7C(O)$—, —$NR^7$—, —$S(O)_2N(R^{10})$—, —$N(R^{10})S(O))_2$— or —S(=O)$_m$—;

m is 0, 1 or 2;
n is independently 0, 1, 2, 3 or 4;
p is independently 0, 1, 2, 3 or 4;
q is 0, 1, 2 or 3;
r is 0 to 5, or a pharmaceutically acceptable salt thereof.

2. The compound according to claim 1 having the formula $B^1$:

$B^1$ wherein:
Y is selected from: phenyl and cyclohexyl;

$R^1$ is selected from: hydrogen, $C_3$–$C_{10}$ cycloalkyl, $R^{10}O$—, —$N(R^{10})_2$, F or $C_1$–$C_6$ alkyl;

$R^2$ is independently selected from:
  a) hydrogen,
  b) aryl, $C_3$–$C_{10}$ cycloalkyl, $R^{10}O$—, —$N(R^{10})_2$, F or $C_2$–$C_6$ alkenyl,
  c) unsubstituted or substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $R^{10}O$— and —$N(R^{10})_2$;

$R^3$ and $R^4$ are independently selected from:
  a) hydrogen,
  b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^{6a}$, $R^{6b}$, $R^{6c}$, $R^{6d}$ and $R^{6e}$ are independently selected from:
  a) hydrogen,
  b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $(R^{10})_2NS(O)_2$—, $R^{11}S(O)_mNR^{10}$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $(R^{10})_2NS(O)_2$—, $R^{11}S(O)_mNR^{10}$—, $R^{10}{}_2N$—$C(NR^{10})$—, CN, $R^{10}C(O)$—, $N_3$, —$N(R^{10})_2$, and $R^{11}OC(O)$—$NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

$R^8$ is independently selected from:

a) hydrogen,
b) aryl, substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, $(R^{10})_2NC(O)$—, $(R^{10})_2NS(O)_2$—, $R^{11}S(O)_mNR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $(R^{10})_2NS(O)_2$—, $R^{11}S(O)_mNR^{10}$—, $R^{10}C(O)$—, —$N(R^{10})_2$, or $R^{11}OC(O)NR^{10}$—;

$R^{9a}$ and $R^{9b}$ are independently hydrogen, $C_1$–$C_6$ alkyl, trifluoromethyl and halogen;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, aryl, substituted aryl, $C_1$–$C_6$ perfluoroalkyl, 2-aminoethyl and 2,2,2-trifluoroethyl;

$A^1$ is selected from: a bond, —CH=CH—, —C≡C—, C(O)—, —C(O)NR$^{10}$—, O, —N(R$^{10}$)—, or S(O)$_m$;

$A^3$ is selected from: —CH$_2$—, O, —N(R$^{10}$)—, —C(O)NR$^{10}$—, —C(O)NR$^{10}$CH$_2$—, —CH$_2$C(O)NR$^{10}$—, —CH$_2$O—, —OCH$_2$— or S(O)$_m$;

X is a bond, —CH=CH—, —C(O)NR$^{10}$—, —NR$^{10}$C(O)—, —NR$^{10}$—, O or —C(=O)—;

m is 0, 1 or 2;

n is independently 0, 1, 2, 3 or 4;

p is 0, 1, 2, 3 or 4; and

3. The compound according to claim 1 having the formula $C^1$:

wherein:

Y is selected from: phenyl and cyclohexyl;

$R^1$ is selected from: hydrogen, $C_3$–$C_{10}$ cycloalkyl, $R^{10}O$—, —$N(R^{10})_2$, F or $C_1$–$C_6$ alkyl;

$R^2$ is independently selected from:
a) hydrogen,
b) aryl, $C_3$–$C_{10}$ cycloalkyl, $R^{10}O$—, —$N(R^{10})_2$, F or $C_2$–$C_6$ alkenyl,
c) unsubstituted or substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $R^{10}O$— and —$N(R^{10})_2$;

$R^3$ and $R^4$ are independently selected from:
a) hydrogen,
b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsub-
stituted or substituted aryl, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)$—$NR^{10}$—;

$R^{6a}$, $R^{6b}$, $R^{6c}$, $R^{6d}$ and $R^{6e}$ are independently selected from:
a) hydrogen,
b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $(R^{10})_2NS(O)_2$—, $R^{11}S(O)_mNR^{10}$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $(R^{10})_2NS(O)_2$—, $R^{11}S(O)_mNR^{10}$—, $R^{10}_2N$—$C(NR^{10})$—, CN, $R^{10}C(O)$—, $N_3$, —$N(R^{10})_2$, and $R^{11}OC(O)$—$NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

$R^8$ is independently selected from:
a) hydrogen,
b) aryl, substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, $(R^{10})_2NC(O)$—, $(R^{10})_2NS(O)_2$—, $R^{11}S(O)_mNR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $(R^{10})_2NS(O)_2$—, $R^{11}S(O)_mNR^{10}$—, $R^{10}C(O)$—, —$N(R^{10})_2$, or $R^{11}OC(O)NR^{10}$—;

$R^{9a}$ and $R^{9b}$ are independently hydrogen, $C_1$–$C_6$ alkyl, trifluoromethyl and halogen;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, aryl, substituted aryl, $C_1$–$C_6$ perfluoroalkyl, 2-aminoethyl and 2,2,2-trifluoroethyl;

$A^1$ is selected from: a bond, —CH=CH—, —C≡C—, —C(O)—, —C(O)NR$^{10}$—, O, —N(R$^{10}$)—, or S(O)$_m$;

$A^3$ is selected from: —CH$_2$—, O, —N(R$^{10}$)—, —C(O)NR$^{10}$—, —C(O)NR$^{10}$CH$_2$—, —CH$_2$C(O)NR$^{10}$—, —CH$_2$O—, —OCH$_2$— or S(O)$_m$;

X is a bond, —CH=CH—, —C(O)NR$^{10}$—, —NR$^{10}$C(O)—, —NR$^{10}$—, O or —C(=O)—;

m is 0, 1 or 2;

n is independently 0, 1, 2, 3 or 4;

p is 0, 1, 2, 3 or 4; and r is 0 to 5;

or a pharmaceutically acceptable salt thereof.

4. The compound according to claim 2 having the formula $D^1$:

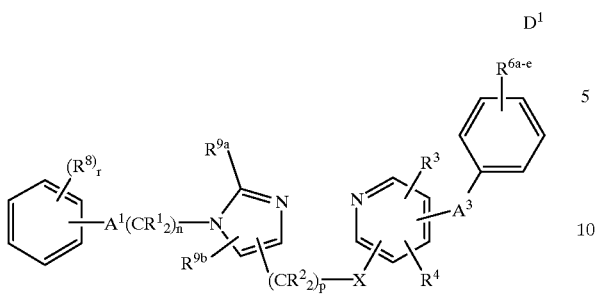

wherein:

$R^1$ is selected from: hydrogen, $C_3-C_{10}$ cycloalkyl or $C_1-C_6$ alkyl;

$R^2$ is independently selected from:
a) hydrogen,
b) aryl, $C_3-C_{10}$ cycloalkyl, $R^{10}O-$, $-N(R^{10})_2$, F or $C_2-C_6$ alkenyl,
c) $C_1-C_6$ alkyl unsubstituted or substituted by aryl, $C_3-C_{10}$ cycloalkyl, $C_2-C_6$ alkenyl, $R^{10}O-$, or $-N(R^{10})_2$;

$R^3$ is selected from:
a) hydrogen,
b) unsubstituted or substituted aryl, $C_3-C_{10}$ cycloalkyl, $C_2-C_6$ alkenyl, $C_2-C_6$ alkynyl, halogen, $C_1-C_6$ perfluoroalkyl, $R^{12}O-$, $R^{11}S(O)_m-$, $R^{10}C(O)NR^{10}-$, $(R^{10})_2NC(O)-$, $R^{10}{}_2N-C(NR^{10})-$, CN, $NO_2$, $R^{10}C(O)-$, $N_3$, $-N(R^{10})_2$, or $R^{11}OC(O)NR^{10}-$,
c) unsubstituted $C_1-C_6$ alkyl,
d) substituted $C_1-C_6$ alkyl wherein the substituent on the substituted $C_1-C_6$ alkyl is selected from unsubstituted or substituted aryl, $C_3-C_{10}$ cycloalkyl, $C_2-C_6$ alkenyl, $C_2-C_6$ alkynyl, $R^{12}O-$, $R^{11}S(O)_m-$, $R^{10}C(O)NR^{10}-$, $(R^{10})_2NC(O)-$, $R^{10}{}_2N-C(NR^{10})-$, CN, $R^{10}C(O)-$, $N_3$, $-N(R^{10})_2$, and $R^{11}OC(O)-NR^{10}-$;

$R^4$ is selected from H, halogen, $C_1-C_6$ alkyl and $CF_3$;

$R^{6a}$, $R^{6b}$, $R^{6c}$, $R^{6d}$ and $R^{6e}$ are independently selected from:
a) hydrogen,
b) unsubstituted or substituted aryl, $C_3-C_{10}$ cycloalkyl, $C_2-C_6$ alkenyl, $C_2-C_6$ alkynyl, halogen, $C_1-C_6$ perfluoroalkyl, $R^{12}O-$, $R^{11}S(O)_m-$, $R^{10}C(O)NR^{10}-$, $(R^{10})_2NC(O)-$, $R^{10}{}_2N-C(NR^{10})-$, CN, $NO_2$, $R^{10}C(O)-$, $N_3$, $-N(R^{10})_2$, or $R^{11}OC(O)NR^{10}-$,
c) unsubstituted $C_1-C_6$ alkyl,
d) substituted $C_1-C_6$ alkyl wherein the substituent on the substituted $C_1-C_6$ alkyl is selected from unsubstituted or substituted aryl, $C_3-C_{10}$ cycloalkyl, $C_2-C_6$ alkenyl, $C_2-C_6$ alkynyl, $R^{12}O-$, $R^{11}S(O)_m-$, $R^{10}C(O)NR^{10}-$, $(R^{10})_2NC(O)-$, $R^{10}{}_2N-C(NR^{10})-$, CN, $R^{10}C(O)-$, $N_3$, $-N(R^{10})_2$, and $R^{11}OC(O)-NR^{10}-$; or any two of $R^{6a}$, $R^{6b}$, $R^{6c}$, $R^{6d}$ and $R^{6e}$ on adjacent carbon atoms are combined to form a diradical selected from $-CH=CH-CH=CH-$, $-CH=CH-CH_2-$, $-(CH_2)_4-$ and $-(CH_2)_3-$;

$R^8$ is independently selected from:
a) hydrogen,
b) aryl, substituted aryl, $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, $(R^{10})_2NC(O)-$, CN, $NO_2$, $(R^{10})_2N-C(NR_{10})-$, $R^{10}C(O)-$, $-N(R^{10})_2$, or $R^{11}OC(O)NR^{10}-$, and
c) $C_1-C_6$ alkyl substituted by $C_1-C_6$ perfluoroalkyl, $R^{10}O-$, $R^{10}C(O)NR^{10}-$, $(R^{10})_2NC(O)-$, $(R^{10})_2N-C(NR^{10})-$, $R^{10}C(O)-$, $-N(R^{10})_2$, or $R^{11}OC(O)NR^{10}-$;

$R^{9a}$ and $R^{9b}$ are independently hydrogen, ethyl, cyclopropyl or methyl;

$R^{10}$ is independently selected from hydrogen, $C_1-C_6$ alkyl, benzyl, 2,2,2-trifluoroethyl and aryl;

$R^{11}$ is independently selected from $C_1-C_6$ alkyl and aryl;

$R^{12}$ is independently selected from hydrogen, $C_1-C_6$ alkyl, $C_1-C_6$ aralkyl, $C_1-C_6$ substituted aralkyl, aryl, substituted aryl, $C_1-C_6$ perfluoroalkyl, 2-aminoethyl and 2,2,2-trifluoroethyl;

$A^1$ is selected from: a bond, $-C(O)-$, O, $-N(R^{10})-$, or $S(O)_m$;

$A^3$ is selected from: $-CH_2-$, O, $-N(R^{10})-$ or $S(O)_m$;

X is a bond, $-CH=CH-$, $-C(O)NR^{10}-$, $-NR^{10}C(O)-$, $-NR^{10}-$, O or $-C(=O)-$, n is 0 or 1; provided that n is not 0 if $A^1$ is a bond, O, $-N(R^{10})-$ or $S(O)_m$;

m is 0, 1 or 2;

p is 0, 1, 2, 3 or 4; and r is 0, 1 or 2;

or a pharmaceutically acceptable salt thereof.

5. The compound according to claim 3 having the formula $E^1$:

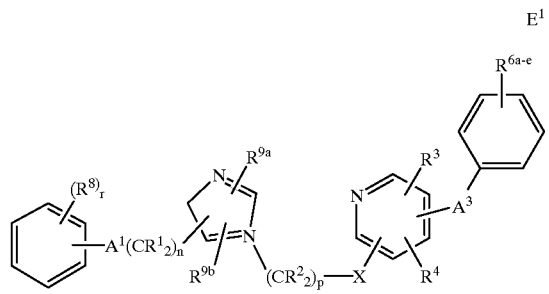

wherein:

$R^1$ is selected from: hydrogen, $C_3-C_{10}$ cycloalkyl or $C_1-C_6$ alkyl;

$R^2$ is independently selected from:
a) hydrogen,
b) aryl, $C_3-C_{10}$ cycloalkyl, $R^{10}O-$, $-N(R^{10})_2$, F or $C_2-C_6$ alkenyl,
c) $C_1-C_6$ alkyl unsubstituted or substituted by aryl, $C_3-C_{10}$ cycloalkyl, $C_2-C_6$ alkenyl, $R^{10}O-$, or $-N(R^{10})_2$;

$R^3$ is selected from:
a) hydrogen,
b) unsubstituted or substituted aryl, $C_3-C_{10}$ cycloalkyl, $C_2-C_6$ alkenyl, $C_2-C_6$ alkynyl, halogen, $C_1-C_6$ perfluoroalkyl, $R^{12}O-$, $R^{11}S(O)_m-$, $R^{10}C(O)NR^{10}-$, $(R^{10})_2NC(O)-$, $R^{10}{}_2N-C(NR^{10})-$, CN, $NO_2$, $R^{10}C(O)-$, $N_3$, $-N(R^{10})_2$, or $R^{11}OC(O)NR^{10}-$,
c) unsubstituted $C_1-C_6$ alkyl,
d) substituted $C_1-C_6$ alkyl wherein the substituent on the substituted $C_1-C_6$ alkyl is selected from unsubstituted or substituted aryl, $C_3-C_{10}$ cycloalkyl, $C_2-C_6$ alkenyl, $C_2-C_6$ alkynyl, $R^{12}O-$, $R^{11}$ $S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^4$ is selected from H, halogen, $C_1$–$C_6$ alkyl and $CF_3$;

$R^{6a}$, $R^{6b}$, $R^{6c}$, $R^{6d}$ and $R^{6e}$ are independently selected from:
a) hydrogen,
b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

$R^8$ is independently selected from:
a) hydrogen,
b) aryl, substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, $(R^{10})_2NC(O)$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2NC(O)$—, $(R^{10})_2N$—$C(NR^{10})$, $R^{10}C(O)$—, —$N(R^{10})_2$, or $R^{11}OC(O)NR^{10}$—;

$R^{9a}$ and $R^{9b}$ are independently hydrogen, ethyl, cyclopropyl or methyl;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, aryl, substituted aryl, $C_1$–$C_6$ perfluoroalkyl, 2-aminoethyl and 2,2,2-trifluoroethyl;

$A^1$ is selected from: a bond, —C(O)—, O, —N($R^{10}$)—, or $S(O)_m$;

$A^3$ is selected from: —CH$_2$—, O, —N($R^{10}$)— or $S(O)_m$;

X is a bond, —CH=CH—, —C(O)NR$^{10}$—, —NR$^{10}$C(O)—, —NR$^{10}$—, O or —C(=O)—, n is 0 or 1; provided that n is not 0 if $A^1$ is a bond, O, —N($R^{10}$)— or $S(O)_m$;

m is 0, 1 or 2;

p is 0, 1, 2, 3 or 4; and r is 0, 1 or 2;

or a pharmaceutically acceptable salt thereof.

6. A compound which is selected from:

5-(4'-Cyanobenzyl)-1-[2-(3''-methylphenylthio)pyrid-5-ylmethyl)-imidazole;

5-(4'-Cyanobenzyl)-1-[2-(3''-methylphenylphenoxy)pyrid-5-ylmethyl)imidazole;

5-(4'-Cyanobenzyl)-1-[2-(3''-chlorophenylthio) pyrid-5-ylmethyl)]-imidazole;

5-(4'-Cyanobenzyl)-1-[2-(cyclohexylthio)pyrid-5-ylmethyl]imidazole;

5-(4'-Cyanobenzyl)-1-[2-(3''-methylphenylthio)pyrid-4-ylmethyl)]-imidazole;

5-(4'-Cyanobenzyl)-1-[2-(cyclohexylamino)pyrid-5-ylmethyl)]imidazole;

5-(4'-Cyanobenzyl)1-[2-(3''-chlorophenylthio)pyrid-5-ylmethyl]-imidazole-S-oxide;

2-[N-(1-(4'-Cyanobenzyl)-1H-imidazol-5-ylethyl) carbamoyl]-6-(3-trifluoromethylphenoxy)pyridine;

3-[N-(1-(4'-Cyanobenzyl)-1H-imidazol-5-ylethyl) carbamoyl]-6-(3-trifluoromethylphenoxy)pyridine;

3-[N-(1-(4'-Cyanobenzyl)-1H-imidazol-5-ylethyl) carbamoyl]-5-(3-trifluoromethylphenoxy)pyridine;

3-[N-(1-(4'-Cyanobenzyl)-1H-imidazol-5-ylethyl) carbamoyl]-5-(3-trifluoromethylbenzyloxy)pyridine;

6-[N-(3-Chlorobenzyl) carbamoyl]-4-ethoxy-pyridine-2-carboxylic acid {2-[3-(4-cyanobenzyl)-3H-imidazol-4-yl]-ethyl}-amide;

6-[N-(3-Chlorophenyl) carbamoyl]-4-ethoxy-pyridine-2-carboxylic acid {2-[3-(4-cyanobenzyl)-3H-imidazol-4-yl]-ethyl }-amide;

4-(3-Chlorobenzyloxy)-6-methoxycarbonyl- pyridine-2-carboxylic acid {2-[3-(4-cyanobenzyl)-3H-imidazol-4-yl]-ethyl}-amide;

4-(5-{[6-(3-chloro-phenoxy)-pyridin-2-ylamino]-methyl}-imidazol-1-ylmethyl)-benzonitrile;

4-(5-{[6-(phenylethynyl)-pyridin-2-ylamino]-methyl}-imidazol-1-ylmethyl)-benzonitrile;

4-(5-{[6-(2,3,4-tetrahydronaphth-6-yloxy)-pyridin-2-ylamino]-metlhyl}-imidazol-1-ylmethyl)-benzotitrile; and 4-(5-{[6-(2-phenylethyl)-pyridin-2-ylamino]-methyl}imidazol-1-ylmethyl)-benzonitrile or pharmaceutically acceptable salts thereof.

7. The compound according to claim 6 which is:

5-(4'-Cyanobenzyl)-1-[2-(3''-chlorophenylthio) pyrid-5-ylmethyl)]imidazole

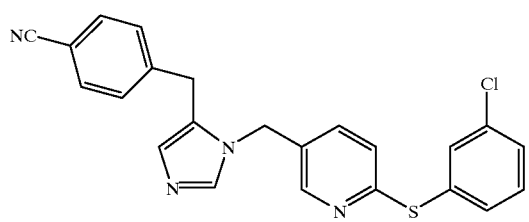

or a pharmaceutically acceptable salt thereof.

8. The compound according to claim 6 which is:

5-(4'-Cyanobenzyl)-1-[2-(3''-methylphenylphenoxy) pyrid-5-ylmethyl)imidazole

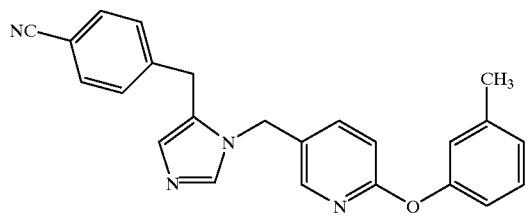

or a pharmaceutically acceptable salt thereof.

9. A pharmaceutical composition comprising a pharmaceutical carrier, and dispersed therein, a therapeutically effective amount of a compound of claim 1.

10. A pharmaceutical composition comprising a pharmaceutical carrier, and dispersed therein, a therapeutically effective amount of a compound of claim 4.

11. A pharmaceutical composition comprising a pharmaceutical carrier, and dispersed therein, a therapeutically effective amount of a compound of claim 5.

12. A pharmaceutical composition comprising a pharmaceutical carrier, and dispersed therein, a therapeutically effective amount of a compound of claim 6.

13. A pharmaceutical composition made by combining the compound of claim 1 and a pharmaceutically acceptable carrier.

14. A process for making a pharmaceutical composition comprising combining a compound of claim 1 and a pharmaceutically acceptable carrier.

r is 0 to 5;
or a pharmaceutically acceptable salt thereof.

15. A method for treating cancer by inhibiting farnesyl-protein transferase which comprises administering to a mammal in need thereof a therapeutically effective amount of a composition of claim 9.

16. A method for treating cancer by inhibiting farnesyl-protein transferase which comprises administering to a mammal in need thereof a therapeutically effective amount of a composition of claim 10.

17. A method for treating cancer by inhibiting farnesyl-protein transferase in treating cancer which comprises administering to a mammal in need thereof a therapeutically effective amount of a composition of claim 11.

18. A method for treating cancer by inhibiting farnesyl-protein transferase in treating cancer which comprises administering to a mammal in need thereof a therapeutically effective amount of a composition of claim 12.

* * * * *

SEQUENCE LISTING

```
<160> NUMBER OF SEQ ID NOS: 26

<210> SEQ ID NO 1
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 1

Cys Val Ile Met
1

<210> SEQ ID NO 2
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 2

Cys Val Leu Leu
1

<210> SEQ ID NO 3
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 3

Cys Val Val Met
1

<210> SEQ ID NO 4
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 4

Cys Ile Ile Met
1

<210> SEQ ID NO 5
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 5

Cys Leu Leu Leu
```

1

<210> SEQ ID NO 6
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 6

Cys Gln Leu Leu
 1

<210> SEQ ID NO 7
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 7

Cys Ser Ile Met
 1

<210> SEQ ID NO 8
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 8

Cys Ala Ile Met
 1

<210> SEQ ID NO 9
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 9

Cys Lys Val Leu
 1

<210> SEQ ID NO 10
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 10

Cys Leu Ile Met
 1

<210> SEQ ID NO 11
<211> LENGTH: 4
<212> TYPE: PRT
<213> ORGANISM: Artificial Sequence
<220> FEATURE:
<223> OTHER INFORMATION: C-terminus CAAX sequence of prenyl-protein transferase substrate

<400> SEQUENCE: 11

Cys Val Leu Ser
 1

<210> SEQ ID NO 12
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 12

Cys Ala Ile Leu
 1

<210> SEQ ID NO 13
<211> LENGTH: 15
<212> TYPE: PRT
<213> ORGANISM: Artificial Sequence
<220> FEATURE:
<223> OTHER INFORMATION: synthesized peptide substrate for
      geranylgeranyl-protein transferase type I

<400> SEQUENCE: 13

Gly Lys Lys Lys Lys Lys Ser Lys Thr Lys Cys Val Ile Met
 1               5                  10                  15

<210> SEQ ID NO 14
<211> LENGTH: 86
<212> TYPE: DNA
<213> ORGANISM: Artificial Sequence
<220> FEATURE:
<223> OTHER INFORMATION: completely synthesized nucleotide sequence

<400> SEQUENCE: 14
tctcctcgag gccaccatgg ggagtagcaa gagcaagcct aaggacccca gccagcgccg      60
gatgacagaa tacaagcttg tggtgg                                          86

<210> SEQ ID NO 15
<211> LENGTH: 33
<212> TYPE: DNA
<213> ORGANISM: Artificial Sequence
<220> FEATURE:
<223> OTHER INFORMATION: completely synthesized nucleotide sequence

<400> SEQUENCE: 15
cacatctaga tcaggacagc acagacttgc agc                                  33

<210> SEQ ID NO 16
<211> LENGTH: 41
<212> TYPE: DNA
<213> ORGANISM: Artificial Sequence
<220> FEATURE:
<223> OTHER INFORMATION: completely synthesized nucleotide sequence

<400> SEQUENCE: 16
tctcctcgag gccaccatga cagaatacaa gcttgtggtg g                         41

<210> SEQ ID NO 17
<211> LENGTH: 38
<212> TYPE: DNA
<213> ORGANISM: Artificial Sequence
<220> FEATURE:

<223> OTHER INFORMATION: completely synthesized nucleotide sequence

<400> SEQUENCE: 17
cactctagac tggtgtcaga gcagcacaca cttgcagc        38

<210> SEQ ID NO 18
<211> LENGTH: 38
<212> TYPE: DNA
<213> ORGANISM: Artificial Sequence
<220> FEATURE:
<223> OTHER INFORMATION: completely synthesized nucleotide sequence

<400> SEQUENCE: 18
gagagaattc gccaccatga cggaatataa gctggtgg        38

<210> SEQ ID NO 19
<211> LENGTH: 33
<212> TYPE: DNA
<213> ORGANISM: Artificial Sequence
<220> FEATURE:
<223> OTHER INFORMATION: completely synthesized nucleotide sequence

<400> SEQUENCE: 19
gagagtcgac gcgtcaggag agcacacact tgc        33

<210> SEQ ID NO 20
<211> LENGTH: 22
<212> TYPE: DNA
<213> ORGANISM: Artificial Sequence
<220> FEATURE:
<223> OTHER INFORMATION: completely synthesized nucleotide sequence

<400> SEQUENCE: 20
ccgccggcct ggaggagtac ag        22

<210> SEQ ID NO 21
<211> LENGTH: 38
<212> TYPE: DNA
<213> ORGANISM: Artificial Sequence
<220> FEATURE:
<223> OTHER INFORMATION: completely synthesized nucleotide sequence

<400> SEQUENCE: 21
gagagaattc gccaccatga ctgagtacaa actggtgg        38

<210> SEQ ID NO 22
<211> LENGTH: 32
<212> TYPE: DNA
<213> ORGANISM: Artificial Sequence
<220> FEATURE:
<223> OTHER INFORMATION: completely synthesized nucleotide sequence

<400> SEQUENCE: 22
gagagtcgac ttgttacatc accacacatg gc        32

<210> SEQ ID NO 23
<211> LENGTH: 21
<212> TYPE: DNA
<213> ORGANISM: Artificial Sequence
<220> FEATURE:
<223> OTHER INFORMATION: completely synthesized nucleotide sequence

<400> SEQUENCE: 23
gttggagcag ttggtgttgg g        21

-continued

```
<210> SEQ ID NO 24
<211> LENGTH: 38
<212> TYPE: DNA
<213> ORGANISM: Artificial Sequence
<220> FEATURE:
<223> OTHER INFORMATION: completely synthesized nucleotide sequence

<400> SEQUENCE: 24
gagaggtacc gccaccatga ctgaatataa acttgtgg                            38

<210> SEQ ID NO 25
<211> LENGTH: 36
<212> TYPE: DNA
<213> ORGANISM: Artificial Sequence
<220> FEATURE:
<223> OTHER INFORMATION: completely synthesized nucleotide sequence

<400> SEQUENCE: 25
ctctgtcgac gtatttacat aattacacac tttgtc                              36

<210> SEQ ID NO 26
<211> LENGTH: 24
<212> TYPE: DNA
<213> ORGANISM: Artificial Sequence
<220> FEATURE:
<223> OTHER INFORMATION: completely synthesized nucleotide sequence

<400> SEQUENCE: 26
gtagttggag ctgttggcgt aggc                                           24
```